US011471099B2

(12) United States Patent
Burnes et al.

(10) Patent No.: US 11,471,099 B2
(45) Date of Patent: Oct. 18, 2022

(54) PRECISION DIALYSIS MONITORING AND SYNCHRONIZATION SYSTEM

(71) Applicant: Medtronic, Inc., Minneapolis, MN (US)

(72) Inventors: John Burnes, Coon Rapids, MN (US); VenKatesh Manda, Stillwater, MN (US); Tico Blumenthal, Minneapolis, MN (US); Orhan Soykan, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 415 days.

(21) Appl. No.: 16/805,054

(22) Filed: Feb. 28, 2020

(65) Prior Publication Data

US 2020/0289056 A1    Sep. 17, 2020

Related U.S. Application Data

(62) Division of application No. 14/555,065, filed on Nov. 26, 2014, now Pat. No. 10,617,349.

(Continued)

(51) Int. Cl.
*A61B 5/00* (2006.01)
*A61B 5/0205* (2006.01)
(Continued)

(52) U.S. Cl.
CPC .......... *A61B 5/4848* (2013.01); *A61B 5/0022* (2013.01); *A61B 5/021* (2013.01);
(Continued)

(58) Field of Classification Search
CPC ... A61B 5/4848; A61B 5/0022; A61B 5/0205; A61B 5/021; A61B 5/145; A61B 5/349;
(Continued)

(56) References Cited

U.S. PATENT DOCUMENTS 3,602,222 A    8/1971    Herndon
3,608,729 A    9/1971    Haselden
(Continued)

FOREIGN PATENT DOCUMENTS

CN    101193667         6/2008
EP     0266795 A2      11/1987
(Continued)

OTHER PUBLICATIONS

Australian Office Action for App. No. 2016349521, dated Aug. 31, 2020.

(Continued)

*Primary Examiner* — Eugene T Wu
(74) *Attorney, Agent, or Firm* — Roger Hahn; Hahn & Associates

(57) ABSTRACT

A system and method for synchronizing patient medical parameters and dialysis parameters. The system and related method allow for the determination of the effect of dialysis on patient health. The invention also allows for the determination of whether observed patient health effects are due to specific dialysis parameters and for making necessary changes to the dialysis parameters in order to improve patient health.

20 Claims, 28 Drawing Sheets

Related U.S. Application Data

(60) Provisional application No. 62/078,946, filed on Nov. 12, 2014, provisional application No. 61/909,394, filed on Nov. 27, 2013.

(51) Int. Cl.
| | |
|---|---|
| *A61B 5/021* | (2006.01) |
| *A61B 5/145* | (2006.01) |
| *G16H 50/30* | (2018.01) |
| *G16H 20/17* | (2018.01) |
| *G16H 20/40* | (2018.01) |
| *G16H 40/67* | (2018.01) |
| *A61B 5/349* | (2021.01) |
| *A61B 5/361* | (2021.01) |
| *A61B 5/363* | (2021.01) |
| *A61B 5/024* | (2006.01) |

(52) U.S. Cl.
CPC ............ *A61B 5/0205* (2013.01); *A61B 5/145* (2013.01); *A61B 5/349* (2021.01); *A61B 5/361* (2021.01); *A61B 5/363* (2021.01); *A61B 5/7275* (2013.01); *G16H 20/17* (2018.01); *G16H 20/40* (2018.01); *G16H 40/67* (2018.01); *G16H 50/30* (2018.01); *A61B 5/024* (2013.01)

(58) Field of Classification Search
CPC ....... A61B 5/361; A61B 5/363; A61B 5/7275; A61B 5/024
See application file for complete search history.

(56) References Cited

U.S. PATENT DOCUMENTS

| | | |
|---|---|---|
| 3,669,878 A | 6/1972 | Marantz |
| 3,669,880 A | 6/1972 | Marantz |
| 3,850,835 A | 11/1974 | Marantz |
| 3,884,808 A | 5/1975 | Scott |
| 3,989,622 A | 11/1976 | Marantz |
| 4,060,485 A | 11/1977 | Eaton |
| 4,371,385 A | 2/1983 | Johnson |
| 4,374,382 A | 2/1983 | Markowitz |
| 4,381,999 A | 5/1983 | Boucher |
| 4,460,555 A | 7/1984 | Thompson |
| 4,556,063 A | 12/1985 | Thompson |
| 4,562,751 A | 1/1986 | Nason |
| 4,581,141 A | 4/1986 | Ash |
| 4,650,587 A | 3/1987 | Polak |
| 4,678,408 A | 7/1987 | Mason |
| 4,685,903 A | 8/1987 | Cable |
| 4,750,494 A | 6/1988 | King |
| 4,799,493 A | 1/1989 | DuFault |
| 4,826,663 A | 5/1989 | Alberti |
| 4,828,693 A | 5/1989 | Lindsay |
| 5,080,653 A | 1/1992 | Voss |
| 5,092,886 A | 3/1992 | Dobos-Hardy |
| 5,097,122 A | 3/1992 | Colman |
| 5,127,404 A | 7/1992 | Wyborny |
| 5,284,470 A | 2/1994 | Beltz |
| 5,302,288 A | 4/1994 | Meidl |
| 5,305,745 A | 4/1994 | Zacouto |
| 5,318,750 A | 6/1994 | Lascombes |
| 5,468,388 A | 11/1995 | Goddard |
| 5,683,432 A | 11/1997 | Goedeke |
| 5,762,782 A | 6/1998 | Kenley |
| 5,819,007 A | 10/1998 | Elghazzawi |
| 5,944,684 A | 8/1999 | Roberts |
| 5,987,352 A | 11/1999 | Klein |
| 6,048,732 A | 4/2000 | Anslyn |
| 6,052,622 A | 4/2000 | Holmstrom |
| 6,058,331 A | 5/2000 | King |
| 6,230,059 B1 | 5/2001 | Duffin |
| 6,248,093 B1 | 6/2001 | Moberg |
| 6,254,567 B1 | 7/2001 | Treu |
| 6,321,101 B1 | 11/2001 | Holmstrom |
| 6,362,591 B1 | 3/2002 | Moberg |
| 6,363,279 B1 | 3/2002 | Ben-Haim |
| 6,554,798 B1 | 4/2003 | Mann |
| 6,555,986 B2 | 4/2003 | Moberg |
| 6,589,229 B1 | 7/2003 | Connelly |
| 6,602,399 B1 | 8/2003 | Fromherz |
| 6,609,023 B1 | 8/2003 | Fischell |
| 6,627,164 B1 | 9/2003 | Wong |
| 6,676,608 B1 | 1/2004 | Keren |
| 6,711,439 B1 | 3/2004 | Bradley |
| 6,818,196 B2 | 11/2004 | Wong |
| 6,878,283 B2 | 4/2005 | Thompson |
| 6,960,179 B2 | 11/2005 | Gura |
| 7,077,819 B1 | 7/2006 | Goldau |
| 7,208,092 B2 | 4/2007 | Micheli |
| 7,276,042 B2 | 10/2007 | Polaschegg |
| 7,404,799 B1 | 7/2008 | Koh |
| 7,566,432 B2 | 7/2009 | Wong |
| 7,575,564 B2 | 8/2009 | Childers |
| 7,610,086 B1 | 10/2009 | Ke |
| 7,674,231 B2 | 3/2010 | McCombie |
| 7,704,361 B2 | 4/2010 | Garde |
| 7,736,507 B2 | 6/2010 | Wong |
| 7,754,852 B2 | 7/2010 | Burnett |
| 7,756,572 B1 | 7/2010 | Fard |
| 7,776,210 B2 | 8/2010 | Rosenbaum |
| 7,794,141 B2 | 9/2010 | Perry |
| 7,850,635 B2 | 12/2010 | Polaschegg |
| 7,867,214 B2 | 1/2011 | Childers |
| 7,922,686 B2 | 4/2011 | Childers |
| 7,922,911 B2 | 4/2011 | Micheli |
| 7,947,179 B2 | 5/2011 | Rosenbaum |
| 7,967,022 B2 | 6/2011 | Grant |
| 7,981,082 B2 | 7/2011 | Wang |
| 8,034,161 B2 | 10/2011 | Gura |
| 8,070,709 B2 | 12/2011 | Childers |
| 8,096,969 B2 | 1/2012 | Roberts |
| 8,183,046 B2 | 5/2012 | Lu |
| 8,187,250 B2 | 5/2012 | Roberts |
| 8,246,826 B2 | 8/2012 | Wilt |
| 8,273,049 B2 | 9/2012 | Demers |
| 8,292,594 B2 | 10/2012 | Tracey |
| 8,313,642 B2 | 11/2012 | Yu |
| 8,317,492 B2 | 11/2012 | Demers |
| 8,357,113 B2 | 1/2013 | Childers |
| 8,366,316 B2 | 2/2013 | Kamen |
| 8,366,655 B2 | 2/2013 | Kamen |
| 8,409,441 B2 | 4/2013 | Wilt |
| 8,499,780 B2 | 8/2013 | Wilt |
| 8,518,260 B2 | 8/2013 | Raimann |
| 8,535,525 B2 | 9/2013 | Heyes |
| 8,580,112 B2 | 11/2013 | Updyke |
| 8,597,227 B2 | 12/2013 | Childers |
| 8,696,626 B2 | 4/2014 | Kirsch |
| 8,903,492 B2 | 12/2014 | Soykan |
| 9,398,853 B2 | 7/2016 | Nanikashvili |
| 2002/0016550 A1 | 2/2002 | Sweeney |
| 2002/0042561 A1 | 4/2002 | Schulman |
| 2002/0112609 A1 | 8/2002 | Wong |
| 2003/0028089 A1 | 4/2003 | Galley |
| 2003/0069481 A1 | 4/2003 | Hervy |
| 2003/0080059 A1 | 5/2003 | Peterson |
| 2003/0097086 A1 | 5/2003 | Gura |
| 2003/0105435 A1 | 6/2003 | Taylor |
| 2003/0114787 A1 | 6/2003 | Gura |
| 2003/0187479 A1 | 10/2003 | Thong |
| 2004/0019312 A1 | 1/2004 | Childers |
| 2004/0099593 A1 | 5/2004 | DePaolis |
| 2004/0147900 A1 | 7/2004 | Polaschegg |
| 2004/0215090 A1 | 10/2004 | Erkkila |
| 2005/0065760 A1 | 3/2005 | Murtfeldt |
| 2005/0113796 A1 | 5/2005 | Taylor |
| 2005/0126961 A1 | 6/2005 | Bissler |
| 2005/0126998 A1 | 7/2005 | Childers |
| 2005/0150832 A1 | 7/2005 | Tsukamoto |
| 2005/0234354 A1* | 10/2005 | Rowlandson ........ A61B 5/7275 600/509 |

(56) References Cited

U.S. PATENT DOCUMENTS

| | | |
|---|---|---|
| 2005/0234357 A1 | 10/2005 | Xue |
| 2005/0234381 A1 | 10/2005 | Niemetz |
| 2005/0234534 A1 | 10/2005 | Rowlandson |
| 2005/0274658 A1 | 12/2005 | Rosenbaum |
| 2006/0025661 A1 | 2/2006 | Sweeney |
| 2006/0217771 A1 | 2/2006 | Soykan |
| 2006/0191850 A1 | 8/2006 | Bosetto |
| 2006/0195064 A1 | 8/2006 | Plahey |
| 2006/0226079 A1 | 10/2006 | Mori |
| 2006/0241709 A1 | 10/2006 | Soykan |
| 2006/0247548 A1 | 11/2006 | Sarkar |
| 2006/0264894 A1 | 11/2006 | Moberg |
| 2007/0007208 A1 | 1/2007 | Brugger |
| 2007/0038138 A1 | 2/2007 | Gill |
| 2007/0066928 A1 | 3/2007 | Lannoy |
| 2007/0138011 A1 | 6/2007 | Hofmann |
| 2007/0175827 A1 | 8/2007 | Wariar |
| 2007/0179431 A1 | 8/2007 | Roberts |
| 2007/0215545 A1 | 9/2007 | Bissler |
| 2007/0255250 A1 | 11/2007 | Moberg |
| 2007/0276270 A1 | 11/2007 | Tran |
| 2008/0006570 A1 | 1/2008 | Gura |
| 2008/0021337 A1 | 1/2008 | Li |
| 2008/0053905 A9 | 3/2008 | Brugger |
| 2008/0067132 A1 | 3/2008 | Ross |
| 2008/0215247 A1 | 9/2008 | Tonelli |
| 2009/0020471 A1 | 1/2009 | Tsukamoto |
| 2009/0101577 A1 | 4/2009 | Fulkerson |
| 2009/0124869 A1 | 5/2009 | Hu |
| 2009/0127193 A1 | 5/2009 | Updyke |
| 2009/0275849 A1 | 11/2009 | Stewart |
| 2009/0275883 A1 | 11/2009 | Chapman |
| 2009/0281484 A1 | 11/2009 | Childers |
| 2009/0282980 A1 | 11/2009 | Gura |
| 2010/0004588 A1 | 1/2010 | Yeh |
| 2010/0010429 A1 | 1/2010 | Childers |
| 2010/0078381 A1 | 4/2010 | Merchant |
| 2010/0078387 A1 | 4/2010 | Wong |
| 2010/0084330 A1 | 4/2010 | Wong |
| 2010/0094158 A1 | 4/2010 | Solem |
| 2010/0114012 A1 | 5/2010 | Sandford |
| 2010/0137693 A1 | 6/2010 | Porras |
| 2010/0168546 A1 | 7/2010 | Kamath |
| 2010/0217181 A1 | 8/2010 | Roberts |
| 2010/0224492 A1 | 9/2010 | Ding |
| 2010/0234795 A1 | 9/2010 | Wallenas |
| 2010/0241045 A1 | 9/2010 | Kelly |
| 2011/0017665 A1 | 1/2011 | Updyke |
| 2011/0066006 A1 | 3/2011 | Banet |
| 2011/0066043 A1 | 3/2011 | Banet |
| 2011/0077574 A1 | 3/2011 | Sigg |
| 2011/0077575 A1 | 3/2011 | Kraemer |
| 2011/0079558 A1 | 4/2011 | Raimann |
| 2011/0087187 A1 | 4/2011 | Beck |
| 2011/0130666 A1 | 6/2011 | Dong |
| 2011/0137136 A1 | 6/2011 | Kotanko |
| 2011/0141116 A1 | 6/2011 | Dalesch |
| 2011/0184340 A1 | 7/2011 | Tan |
| 2011/0272337 A1 | 11/2011 | Palmer |
| 2011/0301447 A1 | 12/2011 | Park |
| 2011/0301472 A1 | 12/2011 | Grober |
| 2012/0016228 A1 | 1/2012 | Kroh |
| 2012/0083729 A1 | 4/2012 | Childers |
| 2012/0085707 A1 | 4/2012 | Beiriger |
| 2012/0115248 A1 | 5/2012 | Ansyln |
| 2012/0220528 A1 | 8/2012 | VanAntwerp |
| 2012/0258546 A1 | 10/2012 | Marran |
| 2012/0273354 A1 | 11/2012 | Orhan et al. |
| 2012/0273415 A1 | 11/2012 | Gerber |
| 2012/0273420 A1 | 11/2012 | Gerber |
| 2012/0277546 A1 | 11/2012 | Soykan |
| 2012/0277551 A1 | 11/2012 | Gerber |
| 2012/0277552 A1 | 11/2012 | Gerber |
| 2012/0277604 A1 | 11/2012 | Gerber |
| 2012/0277650 A1 | 11/2012 | Gerber |
| 2012/0277655 A1 | 11/2012 | Gerber |
| 2012/0277722 A1 | 11/2012 | Gerber |
| 2012/0283581 A1 | 11/2012 | Olde et al. |
| 2012/0303079 A1* | 11/2012 | Mahajan ............ A61N 1/36564 607/17 |
| 2013/0037465 A1 | 2/2013 | Heyes |
| 2013/0116578 A1 | 5/2013 | An |
| 2013/0199998 A1 | 8/2013 | Kelly |
| 2013/0213890 A1 | 8/2013 | Kelly |
| 2013/0274642 A1 | 10/2013 | Soykan |
| 2013/0324915 A1 | 12/2013 | (Krensky) Britton |
| 2013/0330208 A1 | 12/2013 | Ly |
| 2013/0331774 A1 | 12/2013 | Farrell |
| 2014/0018728 A1 | 1/2014 | Plahey |
| 2014/0042092 A1 | 2/2014 | Akonur |
| 2014/0065950 A1 | 3/2014 | Mendelsohn |
| 2014/0088442 A1 | 3/2014 | Soykan |
| 2014/0110340 A1 | 4/2014 | White |
| 2014/0110341 A1 | 4/2014 | White |
| 2014/0158538 A1 | 6/2014 | Collier |
| 2014/0158588 A1 | 6/2014 | Pudil |
| 2014/0158623 A1 | 6/2014 | Pudil |
| 2014/0190876 A1 | 7/2014 | Meyer |
| 2014/0217028 A1 | 8/2014 | Pudil |
| 2014/0217030 A1 | 8/2014 | Meyer |
| 2014/0220699 A1 | 8/2014 | Pudil |
| 2015/0144539 A1 | 5/2015 | Pudil |
| 2015/0148697 A1 | 5/2015 | Burnes |
| 2015/0149096 A1 | 5/2015 | Soykan |
| 2016/0023467 A1 | 2/2016 | Smith |

FOREIGN PATENT DOCUMENTS

| | | |
|---|---|---|
| EP | 1085295 | 11/2001 |
| EP | 1281351 | 2/2003 |
| EP | 1364666 A1 | 11/2003 |
| EP | 0906768 B1 | 2/2004 |
| EP | 1450879 | 10/2008 |
| EP | 1592494 B1 | 6/2009 |
| EP | 2100553 A1 | 9/2009 |
| EP | 2575827 A2 | 12/2010 |
| EP | 2100553 | 8/2011 |
| EP | 2576453 A2 | 12/2011 |
| EP | 2701580 | 11/2012 |
| EP | 2701595 | 11/2012 |
| EP | 1345856 B1 | 3/2013 |
| EP | 2344220 B1 | 4/2013 |
| EP | 2701596 | 3/2014 |
| EP | 2719406 B1 | 5/2016 |
| JP | S63-143077 | 11/1987 |
| JP | 5-99464 | 10/2012 |
| WO | 9937342 | 7/1999 |
| WO | 0057935 | 10/2000 |
| WO | 200066197 A1 | 11/2000 |
| WO | 200170307 A1 | 9/2001 |
| WO | 2001085295 A2 | 9/2001 |
| WO | 2003043677 A2 | 5/2003 |
| WO | 2003043680 | 5/2003 |
| WO | 2003051422 A2 | 6/2003 |
| WO | 2004008826 | 1/2004 |
| WO | 2004009156 | 1/2004 |
| WO | 2004030716 A2 | 4/2004 |
| WO | 2004030717 A2 | 4/2004 |
| WO | 2004064616 A2 | 8/2004 |
| WO | 2005123230 A2 | 12/2005 |
| WO | 2007089855 A2 | 8/2007 |
| WO | 2009026603 | 12/2008 |
| WO | 2009157877 A1 | 12/2009 |
| WO | 2009157878 A1 | 12/2009 |
| WO | 2010028860 A1 | 3/2010 |
| WO | 2011025705 A1 | 3/2011 |
| WO | WO2013022760 A1 | 8/2011 |
| WO | 2012148781 | 11/2012 |
| WO | 2012148784 | 11/2012 |
| WO | 2012148786 | 11/2012 |
| WO | 2012148789 | 11/2012 |
| WO | 2012162515 A2 | 11/2012 |
| WO | WO2012148788 A1 | 11/2012 |
| WO | 2012172398 | 12/2012 |

(56) References Cited

FOREIGN PATENT DOCUMENTS

| WO | 2013019179 | A1 | 2/2013 |
|---|---|---|---|
| WO | 2013019994 | A2 | 2/2013 |
| WO | 2013025844 | | 2/2013 |
| WO | 2013028809 | A3 | 2/2013 |
| WO | 2013103607 | A1 | 7/2013 |
| WO | 2013103906 | | 7/2013 |
| WO | 2013114063 | A1 | 8/2013 |
| WO | 2013121162 | A1 | 8/2013 |
| WO | 14066254 | | 5/2014 |
| WO | 14066255 | | 5/2014 |
| WO | 14077082 | | 5/2014 |
| WO | 2014121162 | | 8/2014 |
| WO | 2014121163 | | 8/2014 |
| WO | 2014121167 | | 8/2014 |
| WO | 2014121169 | | 8/2014 |
| WO | WO2015081221 | A1 | 6/2015 |

OTHER PUBLICATIONS

[NPL219] U.S. Appl. No. 13/791,755, filed Mar. 8, 2013.
[NPL21] U.S. Appl. No. 13/424,479 dated Nov. 1, 2012.
[NPL220] U.S. Appl. No. 13/757,792, filed Feb. 2, 2013.
[NPL222] U.S. Appl. No. 13/757,794, filed Feb. 2, 2013.
[NPL227] U.S. Appl. No. 13/837,287, filed Mar. 15, 2013.
[NPL22] U.S. Appl. No. 13/424,429 dated Nov. 1, 2012.
[NPL230] Redfield, et. al, Restoration of renal response to atrial natriuretic factor in experimental low-output heat failure, Am. J. Physiol., Oct. 1, 1989, R917-923:257.
[NPL231] Rogoza, et. al., Validation of A&D UA-767 device for the self-measurement of blood pressure, Blood Pressure Monitoring, 2000, 227-231, 5(4).
[NPL234] Lima, et. al., An electrochemical sensor based on nanostructure hollsndite-type manganese oxide for detection of potassium ion, Sensors, Aug. 24, 2009, 6613-8625, 9.
[NPL235] Maclean, et, al., Effects of hindlimb contraction on pressor and muscle interstitial metabolite responses in the cat, J. App. Physiol., 1998, 1583-1592, 85(4).
[NPL237] U.S. Appl. No. 13/757,693, dated Feb. 1, 2013.
[NPL238] PCT Application, PCT/US2013/020404, filed Jan. 4, 2013.
[NPL23] U.S. Appl. No. 13/424,525, published Nov. 1, 2012.
[NPL240] U.S. Appl. No. 13/836,973, filed Mar. 15, 2013.
[NPL241] U.S. Appl. No. 14/259,655, filed Apr. 23, 2014.
[NPL242] U.S. Appl. No. 14/259,589, filed Apr. 23, 2014.
[NPL264] PCT/US2014/014357 International Search Report and Written Opinion dated May 19, 2014.
[NPL268] Ronco et al. 2008, Cardiorenal Syndrome, Journal American College Cardiology, 52:1527-1539, Abstract.
[NPL26] Overgaard, et. al., Activity-induced recovery of excitability in K+-depressed rat soleus muscle, Am. J. P 280: R48-R55, Jan. 1, 2001.
[NPL27] Overgaard. et. al., Relations between excitability and contractility in rate soleusmuscle: role of the NA+-K+ pump and NA+-K-S gradients. Journal of Physiology, 1999, 215-225, 518(1).
[NPL306] Coast, et al. 1990, An approach to Cardiac Arrhythmia analysis Using Hidden Markov Models, IEEE Transactions On Biomedical Engineering. 1990, 37(9):826-835.
[NPL309] Weiner, et. al., Article: Cardiac Function and Cardiovascular Disease in Chronic Kidney Disease, Book: Primer on Kidney Diseases (Author: Greenberg, et al), 2009,499-505, 5th Ed., Saunders Elsevier, Philadelphia, PA.
[NPL310] U.S. Appl. No. 61/480,532, filed Apr. 29, 2011.
[NPL311] U.S. Appl. No. 13/424,479, published Nov. 1, 2012.
[NPL312] U.S. Appl. No. 13/424,429 dated Nov. 1, 2012.
[NPL313] U.S. Appl. No. 13/424,525, published Nov. 1, 2013.
[NPL317] U.S. Appl. No. 61/480,530, filed Apr. 29, 2011.
[NPL318] U.S. Appl. No. 61/480,528 dated Apr. 29, 2011.
[NPL328] Genovesi, et al., Nephrology, Dialysis, Transplantation 2009; 24(8):2529-2536.

[NPL32] Secemsky, et. al, High prevalence of cardiac autonomic dysfunction and T-wave alternans in dialysis patients. Heart Rhythm, Apr. 2011, 592-598: vol. 8, No. 4.
[NPL35] Wei, et. al., Fullerene-cryptand coated piezoelectric crystal urea sensor based on urease, Analytics Chimica Acta, 2001,77-85:437.
[NPL376] Gambro AK 96 Dialysis Machine Operators Manual, Dec. 2012. p. 1-140.
[NPL37] U.S. Appl. No. 13/368,225 dated Feb. 7, 2012.
[NPL383] Leifer et al., A Study on the Temperature Variation of Rise Velocity for Large Clean Bubbles, J. Atmospheric & Oceanic Tech., vol. 17, pp. 1392-1402, Oct. 2000.
[NPL384] Talaia, Terminal Velocity of a Bubble Rise in a Liquid Column, World Acad. of Sci., Engineering & Tech., vol. 28, pp. 264-268, Published Jan. 1, 2007.
[NPL386] The FHN Trial Group. In-Center. Hemodialysis Six Times per Week versus Three Times per Week, New England Journal of Medicine, 2010 Abstract.
[NPL39] PCT/US2012/034332, International Search Report, date Jul. 5, 2012.
[NPL46] Siegenthaler, et al., Pulmonary fluid status monitoring with intrathoracic impedance, Journal of Clinical Monitoring and Computing, 24:449-451, published Jan. 12, 2011.
[NPL47] U.S. Appl. No. 61/480,544. unpublished.
[NPL55] U.S. Appl. No. 13/424,454, dated Nov. 1, 2012.
[NPL57] U.S. Appl. No. 13/424,467, published Nov. 1, 2012.
[NPL62] U.S. Appl. No. 13/424,533, dated Nov. 1, 2012.
[NPL632] Lakerveld et al., Primary prevention of diabetes mellitus type 2 and cardiovascular diseases using a cognitive behavior program aimed at lifestyle changes in people at risk: Design of a randomized controlled trial, 2008, BMC Endocrine Disorders, 8(6): 1-19.
[NPL633] Gordhandas et al, Real-Time Extraction and Analysis of Key Morphological Features in the Electrocardiogram, for Data Compression and Clinical Decision Support, 2004, Computational Physiology, pp. 15-18.
[NPL67] U.S. Appl. No. 13/424,490, published Nov. 1, 2012.
[NPL68] U.S. Appl. No. 13/424,517, dated Nov. 1, 2012.
[NPL81] U.S. Appl. No. 61/480,539 dated Apr. 29, 2011.
[NPL84] U.S. Appl. No. 61/480,535 dated Apr. 29, 2011.
[NPL90] Nedelkov, et. al., Design of buffer exchange surfaces and sensor chips for biosensor chip mass spectrometry, Proteomics, 2002, 441-446, 2(4).
[NPL] European Search Report App 14865374.4, dated Jun. 12, 2017.
[NPL] European Search Report for Application No. 14865128.4 dated Jun. 20, 2017.
[NPL] Green et al., Sudden Cardiac Death in Hemodialysis Patients: an In-Depth Review , Am J Kidney Dis 57(6)921:929; published Apr. 18, 2011.
[NPL] Rajan et al. Generalized Feature Extraction for Time-Varying Autoregressive Models, IEEE Transacion Signal Processing vol. 44, No. 10; published Oct. 1, 1996.
Chinese Office Action in App. No. 201480059332.5, dated Mar. 30, 2018.
EP OA for App. No. 16709165.1 dated Oct. 22, 2019.
European Office Action for App. No. 14865128.4, dated Jul. 13, 2020.
European Search Report for App. No. 14859115.9, dated Jan. 5, 2018.
Laurent, Jeanpierre, "Continuous Monitoring of Dynamic Systems: Application to Monitoring of Dialyzed Patients" Oct. 30, 2004, received from internet: http://laurent.jeanpierre1.free.fr/recherche/papiers/aista2004.pdf.
PCT/US2016/058579 International Search Report dated Jan. 31, 2017.
PCT/US2016/058579 Written Opinion dated Jan. 31, 2017.
[NPL105] Brynda, et. al., The detection of toman 2-microglcbuiin by grating coupler immunosensor with three dimensional antibody networks. Biosensors & Bioelectronics, 1999, 363-368, 14(4).

(56) References Cited

OTHER PUBLICATIONS

[NPL10] Wheaton, et al., Dowex Ion Exchange Resins—Fundamentals of Ion Exchange; Jun. 2000, pp. 1-9. http://www.dow.com/scripts/litorder.asp?filepath=liquidseps/pdfs/noreg/177-01837.pdf.
[NPL111] Zhong, et. al., Miniature urea sensor based on H(+)-ion sensitive field effect transistor and its application in clinical analysis, Chin. J. Biotechnol., 1992, 57-65. 8(1).
[NPL119] PCT/US2012/034331, International Search Report and Written Opinion dated Jul. 9, 2012.
[NPL121] Roberts M, The regenerative dialysis (REDY) sorbent system. Nephrology, 1998, 275-278:4.
[NPL138] U.S. Appl. No. 61/480,544, dated Apr. 29, 2011.
[NPL139] U.S. Appl. No. 61/480,541 dated Apr. 29, 2011.
[NPL142] Hemametrics, Crit-Line Hematocrit Accuracy, 2003, 1-5, vol. 1, Tech Note No. 11 (Rev. D).
[NPL144] Weissman, S., et al., Hydroxyurea-induced hepatitis in human immunodeficiency virus-positive patients. Clin. Infec. Dis, (Jul. 29, 1999): 223-224.
[NPL146] PCT/US2012/034334, International Search Report, dated Jul. 6, 2012.
[NPL147] PCT/US2012/034335, International Search Report, dated Sep. 5, 2012.
[NPL148] PCT/US/2012/034327, International Search Report, dated Aug. 13, 2013.
[NPL149] PCT/US/2012/034329, International Search Report, dated Dec. 3, 2012.
[NPL14] Foley, et. al., Long Interdialytic Interval and Martality among Patients Receiving Hemodialysis, N Engl Jrnl Med. 2011:365(12):1099-1107.
[NPL15] PCT International Search Report from International Application No. PCT/US2014/067650, dated Mar. 9, 2015.
[NPL169] Wang, Fundamentals of intrathoracic impedance monitoring in heart failure, Am. J. Cardiology, 2007, 3G-10G: Suppl.
[NPL16] PCT/US2014/067650 International Search Report Written Opinion dated Mar. 9, 2015.
[NPL170] Bleyer, et al, Kidney International. Jun. 2006; 69(12):2268-2273.
[NPL176] Bleyer, et. al., Sudden and cardiac death rated in hemodialysis patients, Kidney International. 1999, 1553-1559: 55.
[NPL187] PCT/US2012/034333, International Preliminary Report on Patentability, dated Oct. 29, 2013.
[NPL188] PCT/US2012/034333, International Search Report, dated Aug. 29, 2012.
[NPL197] PCT/US2012/034330, International Preliminary Report on Patentability, dated Oct. 29, 2013.
[NPL205] Culleton, BF et al. Effect of Frequent Nocturnal Hemodialysis vs. Conventional Hemodialysis on Left Ventricular Mass and Quality of Life. 2007 Journal of the American Medical Association 298 (11), 1291-1299.
[NPL217] U.S. Appl. No. 13/757,722, filed Feb. 1, 2013.
[NPL218] U.S. Appl. No. 13/757,794, filed Feb. 2, 2012.

\* cited by examiner

Relative Fluid Level (Peri-Session)

PRECISION DIALYSIS MONITORING AND SYNCHRONIZATION SYSTEM

FIELD OF THE INVENTION

The device, system and methods of the invention relate to a components and methods that can monitor a mammal with heart failure, kidney disease or both, and make predictions about the likelihood of a life threatening ventricular arrhythmia. The systems and methods of the invention include electronic circuits, electronic sensors, a computer processor, an algorithm and a telecommunications set-up. The invention further relates to methods for signal processing and patient monitoring.

The invention relates to systems and methods for synchronizing and presenting medical data obtained from sensors to provide precision care for dialysis patients. The systems and methods can identify dialysis session parameters and provide clinically actionable information that can be implemented using special-purpose computers and systems to provide improved medical outcomes. The systems include implantable and non-implantable sensors for gathering data on one or more medical parameters, and for gathering data on one or more dialysis session parameter. The collected medical parameter and dialysis session parameter data can be presented in synchronized and/or simultaneous form to assist in analysis and possible modification of dialysis parameters to reduce incidence and risk of arrhythmia and/or Sudden Cardiac Death (SCD).

The systems and methods further provide for computer-assisted methods for dialysis algorithms capable of implementing clinical action on networked health systems in a secure, HIPAA compliant environment based on any of the collected data. The systems and methods can further connect patient data to an Electronic Medical Record (EMR) providing historical data to assist in future dialysis sessions.

BACKGROUND

Dialysis patients have very high mortality rates with Cardiac Disease accounting for 43% of deaths. Data indicates that approximately 27% of the mortalities are due to Sudden Cardiac Death (SCD). SCD is unexpected death from a cardiac cause within a short time period, generally less than an hour from the onset of symptoms in a person without a prior condition that would appear to be fatal. In most cases, SCD death occurs because of Ventricular Arrhythmias (abnormal heart rhythms), including Ventricular Tachycardia (VT) or Ventricular Fibrillation (VF). Moreover, Life Threatening Ventricular Arrhythmia (LTVA), specifically, is one of the most common causes of death among Chronic Kidney Disease (CKD) patients. CKD, also known as chronic renal disease, is a progressive loss in renal function over a period of months or years. Excessive fluid, ions and other toxins accumulate in patients with CKD. Although CKD patients are usually treated by hemodialysis therapy, the treatment is not continuous, but periodic, causing the build-up of excessive amount of fluids, electrolytes and waste in the body between hemodialysis sessions.

Although hemodialysis and pharmaceutical treatment reduces the concentration of elevated potassium in the blood and in the tissues in a patient, there is no current method to predict the onset of LTVA. As such, there is a need to detect an increase in the likelihood of a LTVA. There is also a need for a method to determine the onset of a life threatening cardiac event, so a patient can be prophylactically treated including by the administration of anti-arrhythmic drugs or additional dialysis. There is also a need for techniques to monitor various bodily functions and parameters such as tissue impedance that can than lead to better capabilities to predict LTVA in patients with cardiac disease, and/or in dialysis patients.

Arrhythmias are sometimes caused by the delivery of dialysis. This may be due to cardiovascular stress caused by fluid overload prior to dialysis, rapid changes in fluid or electrolyte levels during dialysis, or the rebalancing of fluid or electrolyte levels in a period shortly after dialysis. Hemodialysis patients have a rate of fatal arrhythmias that is 40 times greater than the general population. Although End Stage Renal Disease (ESRD) patients are at increased risk of arrhythmias and Sudden Cardiac Death (SCD), known systems do not relate data for the prevalence or likelihood of arrhythmias to a particular dialysis schedule in an on-going, dynamic, or patient-specific manner. Medical care in known dialysis settings fail to provide or respond to feedback obtained from sensors. Further, it is often unknown what happens after a patient has left the medical facility. Importantly, how a patient responds to particular course of dialysis is not collected, stored, analyzed, or associated with a patient medical record. Although physicians may collect pertinent data from disparate sources, the collected data is not obtained nor monitored by specially adapted dialysis computer systems and processors such as implanted ECG and impedance sensors. Moreover, known systems do not monitor physiological data pre- or post-dialysis. Instead, blood pressure or heart rate monitoring is limited to 30-minute intervals during treatment.

Known dialysis systems and methods of treatment provide a fixed schedule of dialysis with little to no monitoring of related medical parameters, and consequently, no adjustment of dialysis parameters. Known dialysis systems also do not collect ECG data when a patient is not inside a hospital setting. Known systems also fail to provide prevalence of arrhythmias data in relationship to a particular set of dialysis parameters in synchronized form. Instead of providing a precise dialysis schedule that responds to observed arrhythmia events, most dialysis is prescribed in advance with little to no computer assisted monitoring. As such, known dialysis systems and methods are incapable of providing personalized care keyed to on-going feedback obtained from a patient.

Known dialysis systems further fail to incorporate data obtained from implantable medical devices (IMDs), such as implantable dialysis devices, pacemakers, drug delivery devices, ILRs, blood panels, a micro-fluidics based ambulatory blood composition monitor, or other devices that can monitor and record medical information from patients, such as the occurrence of arrhythmia, heart rate, or blood pressure. As such, the known systems and methods cannot determine the effect of such obtained data and thereby cannot improve therapy nor correctly align the monitored data with the periodic occurrences of dialysis for further computation and analysis. Known IMDs are not capable of generating a report tailored to show the relationship between changes in the medical data and the occurrence of dialysis for a specific patient. Known systems also cannot monitor at-home dialysis systems. Known monitoring systems do not provide a method to generate reports showing a relationship for long periods before and after dialysis for at-home systems.

Hence, there is a need for a personalized dialysis system that can present and analyze data to optimize dialysis treatment. There is also a need for obtaining, monitoring, and presenting patient data in an on-going, dynamic, or patient-specific manner. The need extends to providing a display for showing a relationship between data from at least one dialysis session parameter and data from at least one medical parameter. The need extends to systems and methods configured for monitoring patients when they are not under direct observation in a hospital or medical care setting. The need includes collecting, analyzing, and displaying inter-session data between dialysis visits. The need further includes configurations for monitoring and transmitting such data for at-home patients.

There is also a need for a medical monitoring system that can simultaneously provide the monitored medical data and show the occurrence of dialysis sessions so that health care personnel can properly interpret the changes in patient health due to dialysis, thereby enabling changes in dialysis treatment in order to avoid unwanted medical issues. There is further a need for a medical monitoring system that can provide displayed reports configured to the needs of medical professionals or researchers for interpreting the effects of dialysis on medical parameters.

There is a need for monitoring physiological data pre- or post-dialysis. There is further a need for providing a precise dialysis schedule that responds to observed arrhythmia events using specially adapted computers and dialysis systems suitable for the requirements of a healthcare setting including patient privacy. There is a need for dialysis systems and methods capable of providing personalized care based on data obtained from a patient. The dialysis systems and methods should incorporate data obtained from implantable medical devices (IMDs), such as implantable dialysis devices, pacemakers, drug delivery devices, ILRs, blood panels, a micro-fluidics based ambulatory blood composition monitor, or other devices that can monitor and record medical information from patients, such as the occurrence of arrhythmia, heart rate, or blood pressure. The need extends to correctly aligning therapy parameters based on the monitored data using specially adapted computers that address the technical challenges extant in healthcare settings such as patient safety and privacy.

SUMMARY OF THE INVENTION

The first aspect of the invention is directed to a medical device and an accompanying algorithm for monitoring of subjects with cardiac disease or kidney disease receiving dialysis treatment, and related medical systems, methods for providing improved treatment and diagnostic medical devices and related monitoring algorithms.

In any embodiment of the first aspect of the invention, a medical device can comprise one or more sensors in electronic communication with a processor, the sensors determining one or more physiological parameters, and communicating the physiological parameter to the processor, and the processors using an algorithm to determine the probability of a ventricular arrhythmia based on the physiological parameters.

In any embodiment of the first aspect of the invention, the physiological parameters can be any one selected from the group of tissue impedance, the number of spontaneous ventricular tachycardia and ventricular fibrillation events per day, the time spent in atrial fibrillation, and information about the patient's dialysis status data. In any embodiment of the first aspect of the invention, at least one of the sensors can be a component integrated into an implantable medical device. In any embodiment of the first aspect of the invention, the medical device can have a signaling mechanism to signal if the probability of ventricular arrhythmia is higher than a preset value. In any embodiment aspect of the invention, the processor can be implanted into a patient.

In any embodiment of the first aspect of the invention, the algorithm, for each of the one or more physiological parameters, can calculate an individual hazard estimate given by $y_1(t)=h_1(t)\otimes x_1(t)$, wherein $h_1(t)=k_1 e^{k_2 t}$, t is time, $y_1(t)$ is the individual hazard estimate at time t, $k_1$ and $k_2$ are constants for the given parameter, $x_1(t)$ is the physiological parameter at time t, and $\otimes$ is a convolution operator.

In any embodiment of the first aspect of the invention, wherein the convolution operator can be defined by $[h_1 \otimes x_1](n)=\Sigma_{m=-\infty}^{+\infty} h_1(m)x_1(n-m)$, wherein n is time, $h_1(n)=k_1 e^{k_2 n}$, $x_1(n)$ is the physiological parameter at time n, and $k_1$ and $k_2$ are constants for the given parameter.

In any embodiment of the first aspect of the invention, the algorithm can further calculate a total hazard function: $f(t)=\Sigma_{m=1}^{n} y_m(t)$, wherein f(t) is the total hazard at time t, $y_m(t)$ is an individual hazard estimate for parameter m at time t, and n is the number of physiological parameters used.

In any embodiment of the first aspect of the invention, the algorithm can further calculate a total hazard function:

$$f(t) = \left( \frac{1}{1 + e^{-(\Sigma_{m=1}^{n} y_m(t))}} \right) + k_9$$

wherein f(t) is the total hazard at time t, $y_m(t)$ is an individual hazard estimate for parameter m at time t, $k_9$ is an offset coefficient, and n is the number of physiological parameters used.

In any embodiment of the first aspect of the invention, the device can be configured to allow for entering actual results at time t for the patient into the processor, and the algorithm can further calculate a total error as the difference between the total hazard and the actual results at time t, and the algorithm can further adjust each of the coefficients to minimize the error.

In any embodiment of the first aspect of the invention, the physiological parameters can be any one of selected from the group consisting of tissue impedance, number of spontaneous ventricular tachycardia and ventricular fibrillation events per day, time spent in atrial fibrillation, and dialysis status data.

Any of the features disclosed as being part of the first aspect of the invention can be included in the first aspect of the invention, either alone or in combination.

The second aspect of the invention is directed to a method for determining the probability of a ventricular arrhythmia. In any embodiment of the second aspect of the invention, the method can have the steps of obtaining one or more physiological parameters of a patient from one or more sensors, communicating the parameters to a processor, wherein the processor utilizes an algorithm to determine the probability of a ventricular arrhythmia.

In any embodiment of the second aspect of the invention, the physiological parameters used for the method can be any one of tissue impedance, the number of spontaneous ventricular tachycardia and ventricular fibrillation events per day, time spent in atrial fibrillation, and information about the dialysis status data.

In any embodiment of the second aspect of the invention, at least one of the physiological parameters can be obtained from a sensor that integrated into an implantable medical device. In any embodiment of the second aspect of the invention, the processor can have a signaling mechanism to signal if the probability of ventricular arrhythmia is greater than a pre-set value.

In any embodiment of the second aspect of the invention, the method can also have a step for treating the patient with a pharmaceutical such as anti-arrhythmia drugs if the probability of ventricular arrhythmia is greater than a pre-set value.

In any embodiment of the second aspect of the invention, the algorithm in any system, method or device of the invention can calculate for each of the one or more physiological parameters, an individual hazard estimate given by $y_1(t)=h_1(t)\otimes x_1(t)$, wherein $h1(t)=k_1 e^{k_2 t}$, t is time, y1(t) is the individual hazard estimate at time t, k1 and k2 are constants for the given parameter, x1(t) is the physiological parameter at time t and $\otimes$ is a convolution operator.

In any embodiment of the second aspect of the invention, the convolution operator in any system, method or device of the invention can be defined by $[h_1 \otimes x_1](n)=\Sigma_{m=-\infty}^{+\infty} h_1(m) x_1(n-m)$, wherein n is time, $h1(n)=k_1 e^{k_2 n}$, x1(n) is the physiological parameter at time n, and k1 and k2 are constants for the given parameter.

In any embodiment of the second aspect of the invention, the algorithm in any system, method or device of the invention can calculate a total hazard function: $f(t)=\Sigma_{m=1}^{n} ym(t)$, wherein f(t) is the total hazard at time t, ym(t) is an individual hazard estimate for parameter m at time t, and n is the number of physiological parameters used.

In any embodiment of the second aspect of the invention, the algorithm can calculate a total hazard function:

$$f(t) = \left( \frac{1}{1 + e^{-(\Sigma_{m=1}^{n} y_m(t))}} \right) + k9$$

wherein f(t) is the total hazard at time t, ym(t) is an individual hazard estimate for parameter m at time t, k9 is an offset coefficient, and n is the number of physiological parameters used.

In any embodiment of the second aspect of the invention, the device, systems or method can also have the steps of entering actual results at time t for the patient into the processor, and the algorithm can also calculate a total error as the difference between the total hazard and the actual results at time t, and the algorithm can further adjust each of the coefficients to minimize the total error.

In any embodiment of the second aspect of the invention, the algorithm in any system, method or device of the invention can also utilize an adaptive filter to alter each of the coefficients for each patient periodically. In any embodiment of the second aspect of the invention, the algorithm can utilize the adaptive filter to alter each of the coefficients for each patient every 14 days.

In any embodiment of the second aspect of the invention, the information about the patient's dialysis status data can be determined by assuming the patient underwent dialysis when the sensor measures a periodic rise in tissue impedance. In any embodiment of the second aspect of the invention, the information about the patient's dialysis status data can be entered manually.

In any embodiment of the second aspect of the invention, the information about the patient's dialysis status data can be communicated to the processor from a patient's electronic medical record. In any embodiment second aspect of the invention, the method can also have the step of communicating the probability of a ventricular arrhythmia to the patient or a health care professional. In any embodiment of the second aspect of the invention, the actual results can be whether or not the patient has been hospitalized.

In any embodiment of the second aspect of the invention, the method can also have the step of entering actual results at time t for a group of patients into the processor, and the algorithm further calculates a total error as the difference between the total hazard and the actual results for the group of patients at time t, and the algorithm further adjusts each of the coefficients for each patient to minimize the error.

In any embodiment of the second aspect of the invention, a system can have one or more sensors in electronic communication with a processor, the sensors obtaining one or more physiological parameters of a patient and communicating the one or more physiological parameters to a processor; and the processor has an algorithm to determine a probability of a ventricular arrhythmia based on the physiological parameters wherein the processor can be component of an implantable medical device or be a separate stand-alone unit such as contained in a desktop computer or base module.

Any of the features disclosed as being part of the second aspect of the invention can be included in the second aspect of the invention, either alone or in combination.

The third aspect of the invention is drawn to a use of a device for determining the probability of a life-threatening ventricular arrhythmia. In any embodiment of the third aspect of the invention, the use can comprise the steps of obtaining one or more physiological parameters from one or more sensors, communicating the physiological parameters to a processor, wherein the processor utilizes an algorithm to determine a probability of a ventricular arrhythmia.

In any embodiment of the third aspect of the invention, the physiological parameters can be tissue impedance, number of spontaneous ventricular tachycardia and ventricular fibrillation events per day, time spent in atrial fibrillation, and information about the dialysis status data.

In any embodiment of the third aspect of the invention, at least one of the physiological parameters can be obtained from a sensor that is a component of an implantable medical device.

In any embodiment of the third aspect of the invention, the processor can further comprise a signaling mechanism to signal if the probability of ventricular arrhythmia is greater than a pre-set value.

In any embodiment of the third aspect of the invention, the algorithm, for each of the one or more physiological parameters, can calculate an individual hazard estimate given by $y_1(t)=h_1(t)\otimes x_1(t)$, wherein $h_1(t)=k_1 e^{k_2 t}$, t is time, $y_1(t)$ is the individual hazard estimate at time t, $k_1$ and $k_2$ are constants for the given parameter, $x_1(t)$ is the physiological parameter at time t, and $\otimes$ is a convolution operator.

In any embodiment of the third aspect of the invention, the convolution operator can be defined by $[h_1 \otimes x_1](n)=\Sigma_{m=-\infty}^{+\infty} h_1(m) x_1(n-m)$, wherein n is time, $h_1(n)=k_1 e^{k_2 n}$, $x_1(n)$ is the physiological parameter at time n, and $k_1$ and $k_2$ are constants for the given parameter.

In any embodiment of the third aspect of the invention, the algorithm can further calculate a total hazard function: $f(t)=\Sigma_{m=1}^{n} y_m(t)$, wherein f(t) is the total hazard at time t, $y_m(t)$ is an individual hazard estimate for parameter m at time t, and n is the number of physiological parameters used.

In any embodiment of the third aspect of the invention, the algorithm can further calculate a total hazard function:

$$f(t) = \left(\frac{1}{1 + e^{-(\Sigma_{m=1}^{n} y_m(t))}}\right) + k_9$$

wherein f(t) is the total hazard at time t, $y_m(t)$ is an individual hazard estimate for parameter m at time t, $k_9$ is an offset coefficient, and n is the number of physiological parameters used.

In any embodiment of the third aspect of the invention, the use can further comprise entering actual results at time t for the patient into the processor, and the algorithm can further calculate a total error as the difference between the total hazard and the actual results at time t, and the algorithm can further adjust each of the coefficients to minimize the error.

In any embodiment of the third aspect of the invention, the algorithm can further utilize an adaptive filter to alter the coefficients for each patient periodically.

In any embodiment of the third aspect of the invention, the algorithm can utilize the adaptive filter to alter the coefficients for each patient every 14 days.

In any embodiment of the third aspect of the invention, the information about the dialysis status data can be entered manually.

In any embodiment of the third aspect of the invention, the information about the dialysis status data can be communicated to the processor from an electronic medical record.

In any embodiment of the third aspect of the invention, the use can further comprise entering actual results at time t for a group of patients into the processor, and the algorithm can further calculate a total error as the difference between the total hazard and the actual results for the group of patients at time t, and the algorithm can further adjust each the coefficients for each patient to minimize the error.

Any of the features disclosed as being part of the third aspect of the invention can be included in the third aspect of the invention, either alone or in combination.

The fourth aspect of the invention relates to a medical monitoring system. In any embodiment of the fourth aspect of the invention, the medical monitoring system can comprise an external or implantable medical device comprising one or more sensors configured to detect at least one medical parameter; an input configured to receive at least one dialysis session parameter; a processor in electronic communication with the external or implantable medical device and the input wherein the processor is configured to synchronize the medical parameter to the at least one dialysis session parameter to determine whether an arrhythmia is related to an occurrence of dialysis.

In any embodiment of the fourth aspect of the invention, the processor can receive fluid management data and electrolyte management data, and determine whether the arrhythmia is due to any one of fluid management, electrolyte management, or both fluid management and electrolyte management.

In any embodiment of the fourth aspect of the invention, the system can provide an electronic-mediated communication to a medical server based on the determination of whether the arrhythmia is due to any one of fluid management, electrolyte management, or both fluid management and electrolyte management or the system provides an electronic-mediated communication to the medical server to adjust monitoring.

In any embodiment of the fourth aspect of the invention, the electronic-mediated communication can be electronically transmitted to one or more of a data hub, a handheld data receiver, or a patient electronic medical record.

In any embodiment of the fourth aspect of the invention, the sensor can be implanted and electronically transmit data via any one of Bluetooth Low Energy, radio frequency, and cellular technologies.

In any embodiment of the fourth aspect of the invention, the medical parameter can be selected from the group consisting of arrhythmia information, heart rate, fluid level, blood ion levels, and blood pressure, post-dialysis weight, and pre-dialysis weight.

In any embodiment of the fourth aspect of the invention, the dialysis session parameter can be selected from the group consisting of an occurrence of dialysis, fluid removal rate, dialysate electrolyte composition, and dialysate pH.

In any embodiment of the fourth aspect of the invention, the system can further comprise a non-transitory memory configured to receive and store the synchronized data from the processor.

In any embodiment of any aspect of the invention, a processor can be a medical device processor having an algorithm to determine a probability of a ventricular arrhythmia based on the physiological parameters. The algorithm, for each of the one or more physiological parameters of a patient, can calculate an individual hazard estimate given by $y_1(t) = h_1(t) \otimes x_1(t)$, wherein $h_1(t) = k_1 e^{k_2 t}$, t is time, $y_1(t)$ is the individual hazard estimate at time t, $k_1$ and $k_2$ are constants for the given parameter, $x_1(t)$ is the physiological parameter at time t, and $\otimes$ is a convolution operator.

Any of the features disclosed as being part of the fourth aspect of the invention can be included in the fourth aspect of the invention, either alone or in combination.

The fifth aspect of the invention is drawn to a medical monitoring system that can comprise a medical device comprising one or more sensors configured to sense at least one medical parameter, an input configured to receive at least one parameter of a dialysis session, a processor in electronic communication with the medical device and the input configured to obtain the data from the medical device and the input, and to synchronize the data from the medical device and the input; and an output configured to output the at least one medical parameter and the at least one parameter of a dialysis session, wherein the output is configured to display the at least one medical parameter and at least one parameter of a dialysis session simultaneously.

In any embodiment of the fifth aspect of the invention, the system can provide an electronic-mediated communication to a medical server based on a determination of whether the arrhythmia is due to any one of fluid management, electrolyte management, or both fluid management and electrolyte management or the processor provides an electronic-mediated communication to a medical server to adjust monitoring.

In any embodiment of the fifth aspect of the invention, the at least one medical parameter can be selected from the group consisting of arrhythmia information, heart rate, fluid level, blood ion levels, and blood pressure, post-dialysis weight, and pre-dialysis weight.

In any embodiment of the fifth aspect of the invention, the arrhythmia information can comprise at least one parameter selected from the group consisting of arrhythmia timing, arrhythmia duration, arrhythmia rate, arrhythmia burden, and arrhythmia type.

In any embodiment of the fifth aspect of the invention, the output can comprise a chart showing at least one medical parameter and at least one dialysis parameter on the same chart.

In any embodiment of the fifth aspect of the invention, the medical device can be configured to continuously monitor the at least one medical parameter.

In any embodiment of the fifth aspect of the invention, the medical device can be an implantable medical device.

In any embodiment of the fifth aspect of the invention, the at least one parameter of a dialysis session can be selected from the group consisting of an occurrence of dialysis, dialysis initiation time, a dialysis time length, and a dialysis session prescription.

In any embodiment of the fifth aspect of the invention, the output can show the at least one medical parameter for a preset time before a dialysis session, during the dialysis session and for a preset time after the dialysis session.

In any embodiment of the fifth aspect of the invention, a user can select the preset time before the dialysis session and the preset time after the dialysis session.

In any embodiment of the fifth aspect of the invention, the preset period can be selected from between: 1 hour-1 year, 1-2 hours, 1 hour-1 day, 4 hours-7 days, 1 day-1 month, 7 days-30 days, 30 days-6 months, or 4 months-1 year.

In any embodiment of the fifth aspect of the invention, the output can show the at least one medical parameter for a period of time including multiple dialysis sessions.

In any embodiment of the fifth aspect of the invention, the input can be configured to automatically receive the at least one parameter of a dialysis session.

In any embodiment of the fifth aspect of the invention, the input can be configured to receive the at least one parameter of a dialysis session from a dialysis machine or a device in communication with a dialysis machine.

In any embodiment of the fifth aspect of the invention, the medical monitoring system can further comprise an interface, wherein the interface is configured to allow for input of at least one parameter of a dialysis session.

Any of the features disclosed as being part of the fifth aspect of the invention can be included in the fifth aspect of the invention, either alone or in combination.

The sixth aspect of the invention relates to a method of displaying medical data and dialysis data simultaneously. In any embodiment of the sixth aspect of the invention, the method can comprise obtaining at least one set of data of at least one medical parameter from a sensor; obtaining at least one parameter from a dialysis session performed on a subject; and associating the at least one medical parameter and the at least one dialysis parameter with a time corresponding to the time of obtaining the at least one medical parameter and at least one dialysis parameter.

In any embodiment of the sixth aspect of the invention, the method can comprise the step of providing a synchronized output showing the at least one set of data of at least one medical parameter and the at least one dialysis parameter as a function of the time.

In any embodiment of the sixth aspect of the invention, the processor can determine whether an arrhythmia is due to fluid management by one or both of: comparing a fluid level of the patient to a fluid level of the patient before, during or after previous dialysis sessions, wherein the previous dialysis sessions did not result in arrhythmia; and comparing the rate and magnitude of fluid level drop during a dialysis session within a set time period of the arrhythmia to a rate and magnitude of fluid level drop during a previous dialysis session of the patient, wherein the previous dialysis session did not result in arrhythmia.

In any embodiment of the sixth aspect of the invention, the method can further comprise continuously monitoring the at least one medical parameter for a period of time over multiple dialysis sessions, and the output can be a display showing the at least one set of data of at least one medical parameter for a period of time including multiple dialysis sessions.

In any embodiment of the sixth aspect of the invention, the method can comprise providing an output showing the at least one set of data of at least one medical parameter for a set time period before the dialysis session, during the dialysis session and after the dialysis sessions.

In any embodiment of the sixth aspect of the invention, the set period before the dialysis session and the set period after a dialysis session can be between any of: 1 hour-1 year, 1-2 hours, 1 hour-1 day, 4 hours-7 days, 1 day-1 month, 7 days-30 days, 30 days-6 months, or 4 months-1 year.

In any embodiment of the sixth aspect of the invention, the at least one set of data of at least one medical parameter can be obtained from an implantable medical device.

In any embodiment of the sixth aspect of the invention, at least one dialysis parameter from a dialysis session can be obtained automatically from a dialysis machine or device in electronic communication with a dialysis machine.

In any embodiment of the sixth aspect of the invention, the method can comprise adjusting a measurement frequency based any one of an occurrence of arrhythmia, patient fluid level, post-dialysis weight, pre-dialysis weight, or a time duration of an arrhythmia.

In any embodiment of the sixth aspect of the invention, the method can comprise further comprising obtaining arrhythmia data for a patient during time periods before, during and after several dialysis sessions, and computing a risk score corresponding to the risk of arrhythmia during each of the time periods.

In any embodiment of the f sixth aspect of the invention, the method can comprise adjusting an ultrafiltration rate or ultrafiltration magnitude based on the processor determining that a rate or magnitude of fluid level drop during a dialysis session within the set time period of the arrhythmia is different from the rate and magnitude of fluid level drop during the previous dialysis session of the patient.

In any embodiment of the sixth aspect of the invention, the output can be provided on a monitor.

In any embodiment of the sixth aspect of the invention, the method can comprise determining the average of the medical parameter value for pre-set time windows before and after each dialysis session, and outputting the average value of the medical parameter in each window before and after each dialysis session.

In any embodiment of the sixth aspect of the invention, the medical parameter can comprise at least one of occurrence of an arrhythmia or occurrence of atrial fibrillation, and the frequency of measurements of the medical parameter can be adjusted based on a frequency of the occurrence of arrhythmia or the occurrence of atrial fibrillation.

In any embodiment of the sixth aspect of the invention, the medical parameter can comprise at least one of a time duration of atrial fibrillation or a time duration of arrhythmia, and the frequency of measurements of the medical parameter can be adjusted based on the time duration of atrial fibrillation or the time duration of arrhythmia.

In any embodiment of the sixth aspect of the invention, the medical parameter can comprise a patient fluid level and an arrhythmia occurrence, and the frequency of measurements can be adjusted based on the patient fluid level.

In any embodiment of the sixth aspect of the invention, the method can comprise obtaining a fluid level of a patient corresponding to an estimated dry weight of the patient, and the frequency of measurements can be adjusted based on the difference between the fluid level of the patient and the fluid level corresponding to the estimated dry weight of the patient.

In any embodiment of the sixth aspect of the invention, the method can comprise obtaining arrhythmia data for a patient during time periods before, during and after several dialysis sessions, and computing a risk score corresponding to the risk of arrhythmia during each of the time periods.

DETAILED DESCRIPTION OF THE INVENTION

Figure 1:
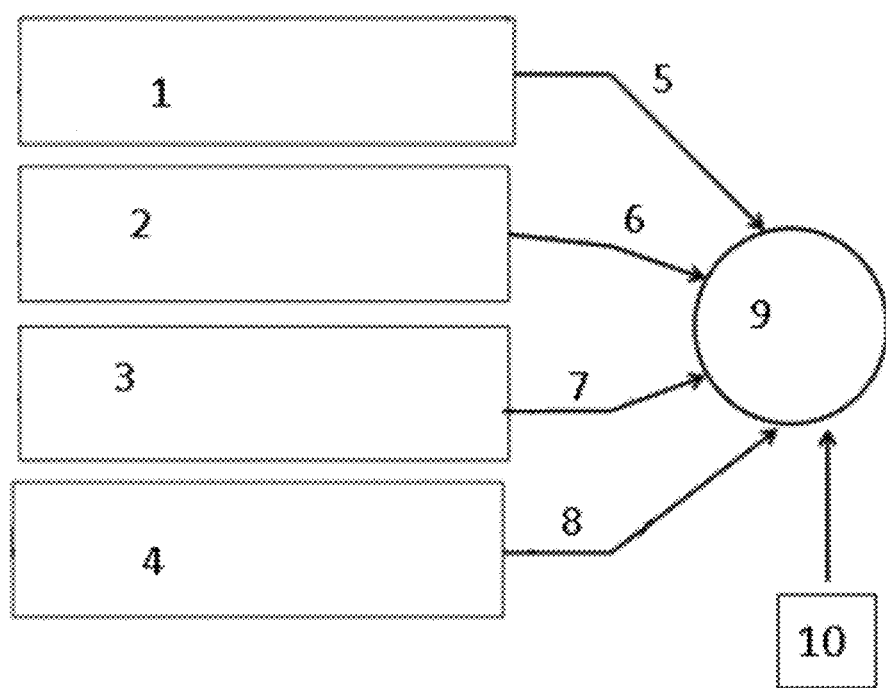
FIG. 1 is a block diagram of the calculation of the total hazard function.

Unless defined otherwise, all technical and scientific terms used herein generally have the same meaning as commonly understood by one of ordinary skill in the relevant art.

The articles "a" and "an" are used herein to refer to one or to more than one (i.e., to at least one) of the grammatical object of the article. For example, "an element" means one element or more than one element.

The term "adaptive filter" refers to a mathematical operation that recalculates constants for use in another operation periodically based on the differences between the predicted results of the second operation and the actual results.

The term "algorithm" refers to a set of steps used to solve a mathematical computation.

An "arrhythmia" or "arrhythmia event" is a condition wherein a subject's heart beats at an abnormal rhythm. As used herein, arrhythmia can refer to atrial fibrillation, atrial flutter, ventricular fibrillation, ventricular tachycardia, bradyarrhythmia, or any type of arrhythmia known in the art.

"Arrhythmia information" refers to any data corresponding to an observed arrhythmia. Arrhythmia information includes, but is not limited to, arrhythmia timing, arrhythmia type, arrhythmia burden, arrhythmia rate, or arrhythmia duration.

The term "atrial fibrillation" refers to a condition wherein the atria beat rapidly and irregularly.

"Bluetooth Low Energy" refers to a wireless communication that transmits data using ultrahigh frequency radio waves.

"Blood ion levels" as used herein refer to the concentration of specific solutes in the blood of a patient.

"Cellular technology" refers to a method of transmitting information electronically through short wave analog or digital signals to or from a transmitter.

The term "chart," as used herein describes a diagram, plot, graph, or visual representation of data of any kind. The chart can be presented on a computer monitor computer window or handheld device and can also be reduced to any tangible medium without limitation.

The term "Chronic Kidney Disease" (CKD) refers to a condition often characterized by the slow loss of kidney function over time. The most common causes of CKD are high blood pressure, diabetes, heart disease, and diseases that cause inflammation in the kidneys. CKD can also be caused by infections or urinary blockages. If CKD progresses, it can lead to end-stage renal disease (ESRD), where the kidneys fail completely.

The terms "communicate" and "communication" include but are not limited to, the connection between the electrical elements of the system, either directly or wirelessly, using optical, electromagnetic, electrical, acoustic or mechanical connections, for data transmission among and between said elements.

The term "comprising" includes, but is not limited to, whatever follows the word "comprising." Use of the term indicates the listed elements are required or mandatory but that other elements are optional and may or may not be present.

The term "configured to detect" refers to the ability of a sensor or detector to make a measurement concerning one or more medical parameters.

The term "configured to receive" refers to the ability of a device to obtain data from another source. The device can be configured to receive data via electronic transmission of the data or by manual entry of the data.

The term "consisting of" includes and is limited to whatever follows the phrase the phrase "consisting of." The phrase indicates the limited elements are required or mandatory and that no other elements may be present.

The phrase "consisting essentially of" includes any elements listed after the phrase and is limited to other elements that do not interfere with or contribute to the activity or action specified in the disclosure for the listed elements. Thus, the phrase indicates that the listed elements are required or mandatory but that other elements are optional and may or may not be present, depending upon whether or not they affect the activity or action of the listed elements.

A "convolution operator" is a mathematical function that operates on two other mathematical functions.

"Dialysate electrolyte composition" refers to the types and/or concentrations of solutes in the dialysate used for a dialysis session.

"Dialysis" is a type of filtration, or a process of selective diffusion through a membrane. Dialysis removes solutes of a specific range of molecular weights via diffusion through a membrane from a fluid to be dialyzed into a dialysate. During dialysis, a fluid to be dialyzed is passed over a filter membrane, while dialysate is passed over the other side of that membrane. Dissolved solutes are transported across the filter membrane by diffusion between the fluids. The dialysate is used to remove solutes from the fluid to be dialyzed. The dialysate can also provide enrichment to the other fluid.

A "dialysis parameter," "dialysis session parameter," or "parameter of a dialysis session" is any factor of a dialysis session that tends to affect the health of the patient during and after dialysis. As used herein, "dialysis parameter" includes, but is not limited to, occurrence of dialysis, fluid removal prescription such as a "dialysis session prescription," fluid removal rate, electrolyte balance of the dialysate or pH of the dialysate.

A "dialysis session" is time period that a patient is treated by dialysis, hemodialysis, hemofiltration, ultrafiltration, or other blood fluid removal therapy.

A "dialysis session prescription" can refer to any parameter of a dialysis session, including the amount of fluid removed, the dialysate composition, the rate of fluid removal, the length of the dialysis session, the frequency of dialysis session or any other parameter used for one or more dialysis sessions of a patient.

The term "dialysis status," as used herein, refers to whether the patient has undergone dialysis, whether and how often the patient is regularly undergoing dialysis, and how long it has been since the patient's last dialysis session.

The term "display" as used herein means presentation of information on a computer screen of any type or form.

A "data hub" is a server or computer system designed to aggregate and store data from multiple sources.

The terms "electrical impedance," "impedance," or "tissue impedance," generally, refer to a measure of the difficulty an electrical current faces when it traverses through a biological tissue. Electrical impedance can be the ratio of the voltage to the current, and given in the units of Ohms. Electrical impedance can be measured by applying a known voltage and measuring the electrical current, or by applying a known electrical current and measuring the resulting voltage. In either case, a direct current (DC) or preferably an alternating current (AC) can be used. The AC waveform can be in the form of a sinusoidal current, a square wave, a pulse train or any other repeating form.

The term "electrocardiogram" (ECG) refers to a time varying waveform, produced by the electrical activity of the cardiac muscle and the associated electrical network within the myocardium. The term is often used interchangeably for the ECG tracing available from the surface of the subject, or from an implantable device.

"Electrolyte management data" refers to data affecting the electrolyte balance of a patient. Electrolyte management data can include the concentration of electrolytes in the patient's blood.

"Electronic communication" refers to the connection between the electrical elements of the system, either directly or wirelessly.

An "electronic-mediated communication" is any communication sent by electronic means. This includes wireless technology or wired communication.

The term "error" as used herein, refers to the difference between the predicted results and the actual results for predictions given based on one or more parameters, and include such physiological parameters as defined herein. "Total error" refers to the combination of all of the errors for each parameter used in the prediction.

"Fluid management data" refers to data affecting the fluid levels of a patient. The data can include ultrafiltration rate, ultrafiltration amount, fluid level, pre-dialysis weight, post-dialysis weight, and frequency of fluid removal.

A "handheld data receiver" refers to a device capable of receiving data in electronic form and small enough to be held in the hand.

The term "implantable medical device" describes a device, component or module intended to be totally or partially introduced, surgically or medically into a mammalian body, or by medical intervention that remains after the procedure.

The term "individual hazard estimate" refers to a function that correlates a single variable with a probability of a given event occurring.

An "input" as used herein is a component that allows data to be entered into or received by a device or system. The input can provision the submission of data of any type for further processing by the device or system.

An "interface" is a component that allows a user to manually communicate information to a processor or a memory device.

The "magnitude of a fluid level drop" refers to the difference between the fluid level of a patient at one point in time and the fluid level of a patient at some other point in time.

A "medical device" is any device, component or module capable of sensing one or more medical parameters and/or delivering medical therapy.

A "medical device processor" refers a special purpose processor that can have any one of the following functions of controlling the collection of external or implantable medical device data, controlling the collection of metadata based on the collected data of any type, synchronizing data, and combinations thereof.

A "medical parameter" is any data that gives information about the health of a patient. As used herein, the term "medical parameter" includes, but is not limited to, electromyogram (EMG), an electroencephalogram (EEG), an electrocardiogram (ECG), tissue impedance, blood pressure, the level of specific ions in the blood of a patient such as, but not limited to potassium, sodium, and calcium, patient weight including both dry weight and wet weight, pre- and post-dialysis, a fluid profile including current and historical profiles, or other data concerning the health of the patient such as arrhythmia information, heart rate, fluid level, blood ion levels, and blood pressure.

A "medical server" is a specifically designed server capable of storing medical information. The medical server can have specialized software enabling the storage and protection of patient medical information.

"Monitoring" refers to the detection of one or more patient parameters.

"Occurrence of dialysis" refers to the initiation of a dialysis session, regardless of whether the session is completed as planned.

An "output" as used herein refers to a result obtained from a computation of any type performed by a processor or computer.

A "patient" is a member of any animal species, preferably a mammalian species, optionally a human. The subject can be an apparently healthy individual, an individual suffering from a disease, or an individual being treated for an acute condition or a chronic disease.

A "patient electronic medical record" is a digital file containing health or medical information from a patient.

The term "physiological parameter" refers to any data without limitations that gives any medical relevant information about the health status of a patient. As used herein, it includes, but is not limited to electromyogram (EMG), an electroencephalogram (EEG), an electrocardiogram (ECG), tissue impedance, or any other data concerning the health of the patient. For example, the physiological parameters can encompasses information such as age, weight, gender, current drug therapies, smoking habits, diet, etc.

"Pre-dialysis weight" refers to the weight of the patient just prior to a dialysis session. "Post-dialysis weight" refers to the weight of a patient immediately after a dialysis session. In any embodiment of the second, third, and fourth inventions, the post-dialysis weight can be the patient's dry weight, or the patient's weight when the patient is not fluid overloaded. The pre-dialysis weight can be the patient's wet weight, or the weight of the patient while the patient is fluid overloaded. The pre-dialysis weight minus the post-dialysis weight would then equal the fluid overload of the patient.

The term "pre-set value," as used herein, refers to a variable wherein the user can determine the value of the variable.

The term "processor" as used herein is a broad term and is to be given its ordinary and customary meaning to a person of ordinary skill in the art. The term refers without limitation to a computer system, state machine, processor, or the like designed to perform arithmetic or logic operations using logic circuitry that responds to and processes the basic instructions that drive a computer. In any embodiment of the first, second, third, and fourth invention, the terms can include ROM ("read-only memory") and/or RAM ("random-access memory") associated therewith.

The term "programmable" as used herein refers to a device using computer hardware architecture and being capable of carrying out a set of commands, automatically.

"Radio frequency" refers to signals in the radio wave portion of the electromagnetic spectrum.

The term "sensory unit" or "sensor" refers to an electronic component capable of measuring a property or condition of interest.

A "signaling mechanism," as used herein, includes any mechanism capable of alerting a person. The signal may be audible, visual, or through some other means such as vibration, that will get the attention of the user.

The term "simultaneously" as used herein refers to the concurrent presentation of data or clinical information of any type in any form. The concurrent presentation of data can include data from the same instance in time, but is not necessarily limited to particular instances in time, and can include past data and future expected data.

"Synchronize," as used herein, means to place two variables of any type on the same time scale.

The terms "treating" and "treatment" refer to the management and care of a patient having a pathology or condition. Treating includes administering one or more embodiments of the present invention to prevent or alleviate the symptoms or complications or to eliminate the disease, condition, or disorder. As used herein, "treatment" or "therapy" refers to both therapeutic treatment and prophylactic or preventative measures. "Treating" or "treatment" does not require complete alleviation of signs or symptoms, does not require a cure, and includes protocols having only a marginal or incomplete effect on a patient.

The term "Ventricular Arrhythmias" refers to any type of abnormal heart rhythms in the ventricles of a heart including Ventricular Tachycardia (VT) or Ventricular Fibrillation (VF) without limitation. One, specific, non-limiting example of a Ventricular Arrhythmia can be a "Life Threatening Ventricular Arrhythmia" (LTVA).

Medical Device and Algorithm

The first, second, third, fourth, fifth and sixth aspects of the invention are directed to a medical device and its accompanying algorithm for monitoring of subjects with cardiac disease or kidney disease receiving dialysis treatment, and related medical systems, methods for providing improved treatment and diagnostic medical devices and related monitoring algorithms.

In any embodiment of the first, second, third, fourth, fifth and sixth aspects of the invention, a medical device can comprise one or more sensors in electronic communication with a processor, the sensors determining one or more physiological parameters of a patient, and communicating the physiological parameter to the processor, and the processors using an algorithm to determine the probability of a ventricular arrhythmia based on the physiological parameters.

In any embodiment of the first, second, third, fourth, fifth and sixth aspects of the invention, the parameters can be any one selected from the group of tissue impedance, the number of spontaneous ventricular tachycardia and ventricular fibrillation events per day, the time spent in atrial fibrillation, and information about the patient's dialysis status data. In any embodiment of the first, second, third, fourth, fifth and sixth aspects of the invention, at least one of the sensors can be a component integrated into an implantable medical device. In any embodiment of the first, second, third, fourth, fifth and sixth aspects of the invention, the medical device can have a signaling mechanism to signal if the probability of ventricular arrhythmia is higher than a preset value. In another embodiment, the processor can be implanted into the patient.

The first, second, third, fourth, fifth and sixth aspects of the invention are also directed to a method for determining the probability of a ventricular arrhythmia. In one embodiment of the first, second, third, fourth, fifth and sixth aspects of the invention, the method can have the steps of obtaining one or more physiological parameters of a patient from one or more sensors, communicating the parameters to a processor, wherein the processor utilizes an algorithm to determine the probability of a ventricular arrhythmia.

In any embodiment of the first, second, third, fourth, fifth and sixth aspects of the invention, the physiological parameters used for the method can be any one of tissue impedance, the number of spontaneous ventricular tachycardia and ventricular fibrillation events per day, time spent in atrial fibrillation, and information about the dialysis status data.

In any embodiment of the first, second, third, fourth, fifth and sixth aspects of the invention, at least one of the physiological parameters can be obtained from a sensor that integrated into an implantable medical device. In any embodiment of the first, second, third, fourth, fifth and sixth aspects of the invention, the processor can have a signaling mechanism to signal if the probability of ventricular arrhythmia is greater than a pre-set value.

In any embodiment of the first, second, third, fourth, fifth and sixth aspects of the invention, the method can also have a step for treating the patient with a pharmaceutical such as anti-arrhythmia drugs if the probability of ventricular arrhythmia is greater than a pre-set value.

In any embodiment of the first, second, third, fourth, fifth and sixth aspects of the invention, the algorithm in any system, method or device of the invention can calculate for each of the one or more physiological parameters, an individual hazard estimate given by $y_1(t)=h_1(t) \otimes x_1(t)$, wherein $h1(t)=k_1 e^{k_2 t}$, t is time, y1(t) is the individual hazard estimate at time t, k1 and k2 are constants for the given parameter, x1(t) is the physiological parameter at time t and $\otimes$ is a convolution operator.

In any embodiment of the first, second, third, fourth, fifth and sixth aspects of the invention, the convolution operator in any system, method or device of the invention can be defined by $[h_1 \otimes x_1](n)=\Sigma_{m=-\infty}^{+\infty} h_1(m) x_1(n-m)$, wherein n is time, $h1(n)=k_1 e^{k_2 n}$, x1(n) is the physiological parameter at time n, and k1 and k2 are constants for the given parameter.

In any embodiment of the first, second, third, fourth, fifth and sixth aspects of the invention, the algorithm in any system, method or device of the invention can calculate a total hazard function: $f(t)=\Sigma_{m=1}^{n} y_m(t)$, wherein f(t) is the total hazard at time t, ym(t) is an individual hazard estimate for parameter m at time t, and n is the number of physiological parameters used.

In any embodiment of the first, second, third, fourth, fifth and sixth aspects of the invention, the algorithm can calculate a total hazard function:

$$f(t) = \left( \frac{1}{1 + e^{-(\Sigma_{m=1}^{n} y_m(t))}} \right) + k9$$

wherein f(t) is the total hazard at time t, ym(t) is an individual hazard estimate for parameter m at time t, k9 is an offset coefficient, and n is the number of physiological parameters used.

In any embodiment of the first, second, third, fourth, fifth and sixth aspects of the invention, the device, systems or method can also have the steps of entering actual results at time t for the patient into the processor, and the algorithm can also calculate a total error as the difference between the total hazard and the actual results at time t, and the algorithm can further adjust each of the coefficients to minimize the total error.

In any embodiment of the first, second, third, fourth, fifth and sixth aspects of the invention, the algorithm in any system, method or device of the invention can also utilize an adaptive filter to alter each of the coefficients for each patient periodically. In another embodiment of the first invention, the algorithm can utilize the adaptive filter to alter each of the coefficients for each patient every 14 days.

In any embodiment of the first, second, third, fourth, fifth and sixth aspects of the invention, the information about the patient's dialysis status data can be determined by assuming the patient underwent dialysis when the sensor measures a periodic rise in tissue impedance. In any embodiment of the first, second, third, fourth, fifth and sixth aspects of the invention, the information about the patient's dialysis status data can be entered manually.

In any embodiment of the first, second, third, fourth, fifth and sixth aspects of the invention, the information about the patient's dialysis status data can be communicated to the processor from a patient's electronic medical record. In any embodiment of the first, second, third, fourth, fifth and sixth aspects of the invention, the method can also have the step of communicating the probability of a ventricular arrhythmia to the patient or a health care professional. In any embodiment of the first, second, third, fourth, fifth and sixth aspects of the invention, the actual results can be whether or not the patient has been hospitalized.

In any embodiment of the first, second, third, fourth, fifth and sixth aspects of the invention, the method can also have the step of entering actual results at time t for a group of patients into the processor, and the algorithm further calculates a total error as the difference between the total hazard and the actual results for the group of patients at time t, and the algorithm further adjusts each of the coefficients for each patient to minimize the error.

In any embodiment of the first, second, third, fourth, fifth and sixth aspects of the invention, a system can have one or more sensors in electronic communication with a processor, the sensors obtaining one or more physiological parameters of a patient and communicating the one or more physiological parameters to a processor; and the processor has an algorithm to determine a probability of a ventricular arrhythmia based on the physiological parameters wherein the processor can be component of an implantable medical device or be a separate stand-alone unit such as contained in a desktop computer or base module.

Computing Unit and Algorithm

Unless specifically stated otherwise, as apparent from the foregoing discussions, it should be appreciated that throughout the specification discussions utilizing terms such as "processing," "computing," "calculating," "determining," or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices. In a similar manner, the term "processor" may refer to any device or portion of a device that processes electronic data from registers and/or memory to transform that electronic data into other electronic data that may be stored in registers and/or memory. A "computing platform" may comprise one or more processors.

Embodiments of the first, second and third aspects of the invention may include apparatuses and/or devices for performing the operations herein. An apparatus may be specially constructed for the desired purposes, or it may comprise a general purpose device selectively activated or reconfigured by a program stored in the device. In any embodiment of the first, second and third aspects of the invention, the invention may be implemented using a combination of any of, e.g., but not limited to, hardware, firmware, and software, etc.

The methods, software and hardware described herein can be embodied in or use transitory or non-transitory computer readable media with instructions that cause a programmable processor to carry out the techniques described herein. A "computer-readable medium" includes but is not limited to read-only memory, Flash memory, EPROM and a magnetic or optical storage medium. A non-transitory computer readable medium includes all computer readable media except for a transitory, propagating signal.

The first, second, third, fourth, fifth and sixth aspects of the invention can detect an increase in the likelihood of a Ventricular Arrhythmia, such as LTVA, to provide prophylactic treatment to a patient in need thereof, such as by the administration of a pharmaceutical to alleviate the condition or by hemodialysis or dialysis. In general, functional kidneys remove excess fluids, electrolytes and other molecules. One of the physiological parameters of kidney function can be measured by one or more sensor in the present invention to provide an input of information into the methods described herein for calculating the likelihood of Ventricular Arrhythmia. In particular, a processor or electronic circuit can use an algorithm to calculate an individual hazard estimate having a physiological parameter obtained from a patient, a time variable, and constants for a given physiological parameters.

The hazard function can use any number of physiological parameters unique to the patient. For example, the hazard function can use tissue impedance, which is directly affected by the amount of fluid being retained by the patient: as fluid retention increases, the electrical impedance measured by an implantable device decreases. In one exemplary algorithm, a decrease in the electrical impedance can indicate an increase in fluid retention and an increased propensity toward a LTVA, and can indicate need for dialysis or administration of pharmaceutical based on the methods for calculating the likelihood of LTVA described herein, including but not limited to administration of anti-arrhythmic drugs. It will be understood that many such parameters and combinations thereof can be used wherein the present invention can determine a number of such parameters to be advantageously used.

The first, second, third, fourth, fifth and sixth aspects of the invention also provide methods for monitoring various bodily functions that can than lead to better abilities to predict Ventricular Arrhythmia in patients with cardiac disease, and/or in dialysis patients. The methods can also reduce the chances for Ventricular Arrhythmia patients suffer by monitoring and forwarding data for analysis according to the methods described herein.

The processing of the information collected by the sensors is carried out by a computing unit that can contain a processor or an electronic circuit. It will be understood that any special purpose machine or computer implementing the algorithms contemplated by the present invention are encompassed by the broadly intended interpretation of the term computing unit. In particular, an algorithm processes signals from all of the sensors to produce an estimation of the risk for an arrhythmia using a mathematical model. In any embodiment of the first, second, third, fourth, fifth and sixth aspects of the invention, the algorithm processes information unique to the patient that is entered manually into the computing unit such as patient weight, age, gender, etc. In any embodiment of the first, second, third, fourth, fifth and sixth aspects of the invention, a non-limiting, and non-exhaustive list of physiological parameters can include AF burden, tissue impedance, ambulatory HRV, respiratory rate, sleep pattern (nocturnal activity), body temperature, heart rate change during dialysis, HRV during the dialysis session, BP reduction during dialysis, mixed venous oxygen saturation, fluid removed during dialysis session, dialysis markers known to those of ordinary skill in the art such a sodium, potassium, etc. measured periodically, patient weight measured, medications and their dosage, and patient supplied data such as (discomfort). The performance of the model is monitored by comparing its predictions to the actual patient outcomes and necessary modifications are made to the model parameters to improve its performance using the algorithms of the present invention.

In any embodiment of the first, second, third, fourth, fifth and sixth aspects of the invention, four of the input variables, which are daily impedance, spontaneous VT/VF, time in AT/AF, and hemodialysis, can influence a patient outcome. Further, the effect that any input variable has on the patient outcome can decrease exponentially as time passes, which will be expressed in the form of a hazard function as shown in Eq. 1:

$$h_1(t) = k_1 e^{k_2 t} \qquad \text{[Eq. 1]}$$

where
h1(t) is the hazard function,
k1 and k2 are constants,
t is time in days.

For each of the input parameters, the hazard function can include two constants. For the first input parameter, the constants can be k1 and k2. For the second input parameter, the constants can be k3 and k4, for the third input parameter the constants can be k5 and k6, for the fourth input parameter the constants can be k7 and k8, for the fifth input parameter the constants can be k9 and k10, for the sixth input parameter the constants can be k11 and k12, for the seventh input parameter the constants can be k13 and k14, for the eighth input parameter the constants can be k15 and k16, and for the ninth input parameter the constants can be k17 and k18. It will be understood that additional input parameters can be included having constants kx and ky where x represents an iteration of a first constant and y represents an iteration of a second constant.

Individual hazard estimates can be calculated as the convolution of the input variable and the corresponding hazard function shown in Eq. 2:

$$y_1(t)=h_1(t)\otimes x_1(t) \quad \text{[Eq. 2]}$$

where
y1(t) is the individual hazard estimate,
h1(t) is the hazard function
x1(t) is the input function,
⊗ is the convolution operator.

The convolution can be carried out in the discrete time domain using Eq. 3:

$$y_1(n)=[h_1\otimes x_1](n)=\Sigma_{m=-\infty}^{+\infty}h_1(m)x_1(n-m) \quad \text{[Eq. 3]}$$

It should be noted that the hazard function h1(t) and the input function x1(t) representing the data, i.e., physiological parameters, from the patient have both limited lengths, i.e. they are finite. Hence, the calculation shown in Eq. 3 can be finite.

The total hazard can be estimated as the summation of the individual hazard estimates as shown in Eq. 4:

$$y_T(t)=f[y_1(t),y_2(t),y_3(t),y_4(t)] \quad \text{[Eq. 4]}$$

where
yT(t) is the total hazard estimate,
y1(t), y2(t), y3(t) and y4(t) are the individual hazard estimates, and
f is the summation function.

The summation function, f, may take the form of a linear summation or a non-linear summation, as shown in Eq. 5 and 6.

$$f_{LIN}[y_1(t),y_2(t),y_3(t),y_4(t)]=y_1(t)+y_2(t)+y_3(t)+y_4(t) \quad \text{[Eq. 5]}$$

$$f_{SIG}[y_1(t),y_2(t),y_3(t),y_4(t)]=\text{Sigmoidal}\{y_1(t)+y_2(t)+y_3(t)+y_4(t)+k_9\} \quad \text{[Eq. 6]}$$

where the Sigmoidal function is given by Eq. 7:

$$\text{Sigmoidal}(w) = \frac{1}{1+e^{-+}} \quad \text{[Eq. 7]}$$

The constant k9 shown in Eq. 6 can be added to provide any necessary offset for the operation of the Sigmoidal function.

FIG. 1 shows a block diagram for the calculation of the total hazard function in any embodiment of the first, second, third, fourth, fifth and sixth aspects of the invention. Four input parameters: tissue impedance 1, ventricular tachycardia and ventricular fibrillation 2, atrial fibrillation 3, and dialysis information 4, can be received by the computing unit. The computer can calculate the individual hazard estimates according to the equations described herein. The hazard estimates based on tissue impedance 5, ventricular tachycardia and ventricular fibrillation 6, atrial fibrillation 7, and dialysis information 8 can be processed by the total hazard estimation function 9, according to either the linear summation or non-linear summation equations as described herein to generate a total risk estimate. If the non-linear summation equation is utilized, then the off-set coefficient k9 10 can be added to the total hazard estimation function 9.

In any embodiment of the first, second, third, fourth, fifth and sixth aspects of the invention, any discrepancy between the estimated hazard and the actual patient outcome can be used for the calculation of the estimation error shown in Eq. 8:

$$\text{error}(n)=z(n)-y_T(n) \quad \text{[Eq. 8]}$$

where
error(n) is the estimation error at time index n,
z(n) is the actual patient outcome at time index n, and
yT(n) is the total hazard estimate at time index n.

Finally, the total error can be calculated as the sum of squared errors shown in Eq. 11:

$$e_{SS}(n) = \sum_{m=-\infty}^{n} \text{error}^2(m) = \sum_{m=-\infty}^{n} [z(m) - =_T(m)]^2 \quad \text{[Eq. 11]}$$

When the total error, ess (n), is minimized, the estimator can produce an output as close as possible to the actual patient outcome.

Figure 2:
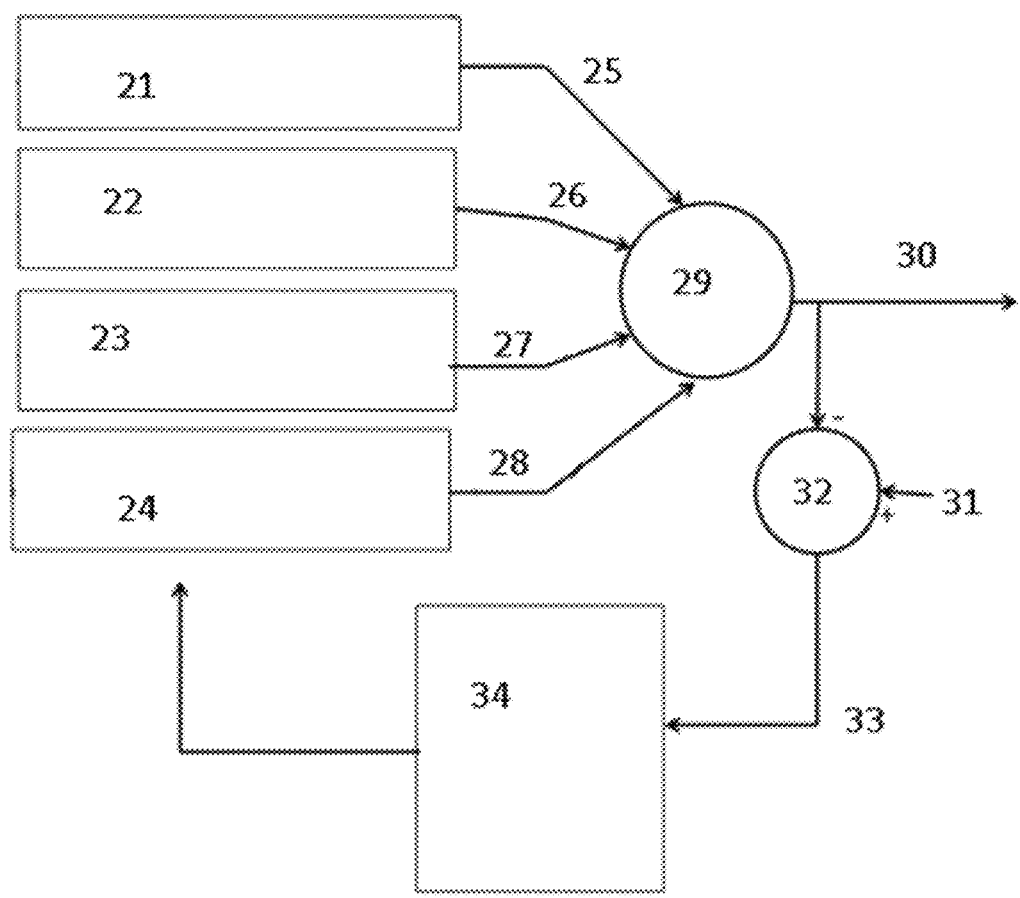
FIG. 2 is a block diagram of the predictive model.

FIG. 2 shows the overall block diagram of the predictive model. The four input parameters: tissue impedance 21, ventricular tachycardia and ventricular fibrillation 22, atrial fibrillation 23 and dialysis information 24, are received by the computing unit. The computer calculates the individual hazard estimates according to the equations described herein. The hazard estimates based on tissue impedance 25, ventricular tachycardia and ventricular fibrillation 26, atrial fibrillation 27 and dialysis information 28 are processed by the total hazard estimation function 29, according to either the linear summation or non-linear summation equations as described herein to generate a total risk estimate 30. This total risk estimate can be transmitted to the user. Additionally, the actual patient outcome 31 is entered, and the computing unit performs the error determination by the equations described herein 32 to generate the total error at time t 33. The computer can then use the error determination to correct the coefficients k1 through k9 34, and feeds the new coefficients back into the individual hazard functions.

In order to correctly reduce the estimation error, the coefficients ki are to be adjusted. Since there is more than one coefficient, this process requires the utilization of a multi-dimensional optimization function, where the goal is to minimize the total error, ess (n). Many algorithms can be used for this task such as Nelder-Mead's downhill simplex method, which is also known as the Amoeba algorithm. In one preferred embodiment, Amoeba algorithm is used, because it does not require the computation of the derivative of the error, ess (n). [Ref: Numerical Recipes in Fortran, The Art of Scientific Computing, W. H. Press, S. A. Teukolsky, W. T. Vetterling and B. P. Flannery]. The described model can be referred to as the non-adaptive model as it does not customize itself to each patient or does not adapt when the patient condition changes. This can be expected because a model using a fixed set of coefficients is not likely to be able account for patient-to-patient variations. Moreover, a model using a fixed set of coefficients cannot adapt to changes that are taking place in the physiological conditions of a given patient. To address these issues, one advanced version of the model that is contemplated in any embodiment of the first, second, third, fourth, fifth and sixth aspects of the invention, can be built using an adaptive filter.

Figure 3A:
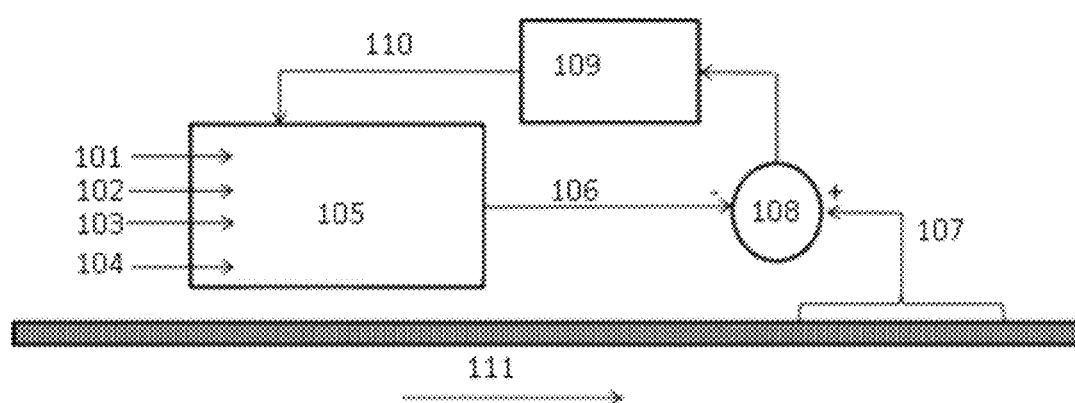
FIG. 3a is an illustration of adaptive version of the predictive model.

As used in any embodiment of the first, second, third, fourth, fifth and sixth aspects of the invention, an adaptive filter based predictor can be illustrated in FIG. 3a and plotted against time 111. The input parameters: tissue impedance 101, ventricular tachycardia and ventricular fibrillation 102, atrial fibrillation 103 and dialysis information 104 are fed into the computing unit or processor, which then performs the individual hazard calculations and the hazard summation described above 105 to give the total hazard estimate at time t 106. The actual patient outcome at time t 107 is then entered into the computing unit to calculate the error at time t 108. The error at time t can then be entered into the adaptive filter 109 to obtain new values for the constants k2, k3, k4, k5, k6, k7, k8, k9 110. It will be understood that the number of constants k2, k3, k4, k5, k6, k7, k8, k9 are not limited to nine and range from any number of required constants, including any one of additional k10 k11, k12, k13, k14 k15, k16, k17, etc. For initialization, the model can be started using some initial values for the parameters k2, k3, k4, k5, k6, k7, k8, k9, which can be determined using the non-adaptive model described herein. However, this new adaptive model can then recalculate the error value at each step using the data from any number of days, e.g., the last 14 days as shown in Eq. 12.

$$g_{error}(n) = \Sigma_{m=n-14}^{n} error^2(m) = \Sigma_{m=n-14}^{n} [z(m) - =_T(m)]^2 \quad [\text{Eq. 12}]$$

Figure 3B:
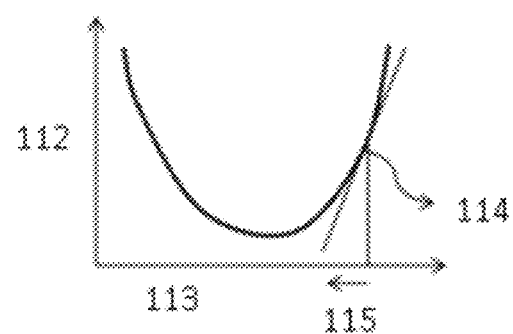
FIG. 3b is a graph showing the error in the prediction as a function of one of the variables.

Once the error, gerror (n), is calculated, its behavior can be studied as a function of each parameter, k2, k3, k4, k5, k6, k7, k8, k9. This can be accomplished by varying each parameter, one by one, while keeping the remaining parameters fixed. This can be shown by the curve in FIG. 3b. The graph shows the plot of the total error function gerror (n) 112 against the value of k1 113. The parameters k2, k3, k4, k5, k6, k7, k8, k9 are kept constant, while the parameter k1 may vary. One can then plot the error, gerror, as a function of k1 only. For illustration, assume that the current value of k1 corresponds to the point labeled as 114 on the graph. To reduce the error function gerror, k1 must be moved toward the left, i.e. the value of k1 must be reduced, perhaps by an amount of 115. This process is repeated for the remaining parameters, k2, k3, k4, k5, k6, k7, k8, k9, to determine the new values for each parameter, which is used during the next iteration. The adaptive filter can be used for the dynamic determination of the coefficients, k2, k3, k4, k5, k6, k7, k8, k9, individually for each subject at each step. In the case of fourteen days, the set of representative calculations can be shown by Eq.'s 13-16.

$$h_1(k_1, k_2, t) = k_1 e^{k_2 t} \quad [\text{Eq. 13}]$$

$$y_1(k_1, k_2, t) = h_1(k_1, k_2, t) \otimes x_1(t) \quad [\text{Eq. 14}]$$

$$\text{Estimate}(k_1, \ldots, k_9, t) = y_T(t) \quad [\text{Eq. 15}]$$

$$g_{ERROR}(k_1, \ldots, k_9, t) = \int_{t-14}^{t} [\text{Actual}(\tau) - \text{Estimate}(\tau)]^2 d\tau \quad [\text{Eq. 16}]$$

One skilled in the art will understand that the adaptive filter may be set to calculate new constants at time intervals other than fourteen days. It may calculate more or less often depending on the needs of the patients. In any embodiment of the first, second, third, fourth, fifth and sixth aspects of the invention, the algorithm can utilize the adaptive filter to alter the coefficients for each patient for any one of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, and 31 days.

In any embodiment of the first, second, third, fourth, fifth and sixth aspects of the invention, the methods predict Ventricular Arrhythmia in a patient whereupon a physician can administer one or more commonly prescribed antiarrhythmic drugs. A non-limiting, partial list of antiarrhythmic drugs can include any one of Amiodarone (Cordarone, Pacerone), Bepridil Hydrochloride (Vascor), Disopyramide (Norpace), Dofetilide (Tikosyn), Dronedarone (Multaq), Flecainide (Tambocor), Ibutilide (Corvert), Lidocaine (Xylocaine), Procainamide (Procan, Procanbid), Propafenone (Rythmol), Propranolol (Inderal), Quinidine, Sotalol (Betapace), or Tocainide (Tonocarid). The drugs can be given intravenously in an emergency situation or orally for long-term treatment. Depending on clinical practice, in patients with atrial fibrillation, a blood thinner (anticoagulant or antiplatelet agent such as aspirin) can also be added to reduce the risk of blood clots and stroke. However, the particular therapies are not critical to the first, second, third, fourth, fifth and sixth aspects of the invention and will depend on a physician's or clinical judgment; whereas the likelihood of a Ventricular Arrhythmia can be determined according to the methods of the first, second, third, fourth, fifth and sixth aspects of the invention.

Processor and Communication System

The computing unit can be a specially adapted unit in order to carry out the purposes and steps described herein. In any embodiment of the first, second, or third aspect of the invention, the sensors described herein can operate in combination or conjunction with circuitry specially adapted to the purposes or steps described herein, or in combination or conjunction with more than one such processor, or in combination or conjunction with one or more elements of each type, such as for distinct steps or portions thereof. The computing unit and the sensors which detect the data in each of the categories are specifically adapted computers and processors configured or a medical or healthcare setting. The computers or processors can have shielded circuitry to prevent electric shock to a patient or operator. In any embodiment of the first, second, and third aspects of the invention, the computers and processors of the present invention are not general purpose computers and can have regulatory approval for approved medical use on patients.

One skilled in the art will recognize that the processor or an electrical circuit used for calculating the methods of the first, second, third, fourth, fifth and sixth aspects of the invention can be integrated into an implantable medical device or can be external to a patient. The methods of constructing such a processor based on the methods described herein are well known and can be fabricated by those of ordinary skill depending on the specific application. It is noted that the present method can be advantageously used in the application of biomedical devices such as ICD and pacemakers, or any other biomedical device having an electrode that can be used as a sensor. Where the processor is external to a device in which the battery is used, the detection of physiological parameters may be made either wirelessly or wired, to the processor. In any embodiment of the first, second, third, fourth, fifth and sixth aspects of the invention, the processor may be a component of a separate device, and may determine the algorithms of the invention upon receiving the physiological parameters. For example, an implantable pacemaker, cardioverter, and/or defibrillator that provide therapy to the heart of a patient via electrodes can be advantageously monitored by the methods and apparatuses of the first, second, third, fourth, fifth and sixth aspects of the invention. In any configuration, the algorithm can use electrical excitation charges used in biomedical electrical stimulation devices to obtain physiological parameters or can passively receive data on such parameters.

The present methods and systems can assist a programmer or clinician to schedule treatment such as administration of a pharmaceutical, dialysis or hemodialysis or determine the dosing or length of time of such procedures. In any embodiment of the first, second, third, fourth, fifth and sixth aspects of the invention, the physiological parameters whether obtained by a sensor, manually entered, or from an electronic record or database, can be entered into a processor or computer unit. From the obtained parameters, the value of the hazard function can be determined by the processor or computing unit. The processor or computing unit can then estimate the probability of a ventricular arrhythmia. The processor or computing unit can then use an obtained result at time t for the patient, and further calculate a total error as the difference between the total hazard and the actual results at time t. In any embodiment of the first, second, third, fourth, fifth and sixth aspects of the invention, the algorithm can further adjust each of the coefficients to minimize the error. The algorithm can also utilize an adaptive filter of any type known to those of skill in the art to alter the coefficients for each patient periodically. In any embodiment of the first, second, third, fourth, fifth and sixth aspects of the invention, the processor or computing can transmit the results to an output display. In any embodiment of the first, second, third, fourth, fifth and sixth aspects of the invention, the systems and methods of the system can transmit the results to a programmer, server, clinician decision tool, 3rd party software, physician or clinician. The obtained results can be transmitted via email, wirelessly, wired transmission, facsimile, or any suitable means for transmitting such information whether via a graphical user interface, iPad or smartphone, or tablet application.

In any embodiment of the first, second, third, fourth, fifth and sixth aspects of the invention, the processor contemplated may include any one or more of a microprocessor, a controller, a digital signal processor (DSP), an application specific integrated circuit (ASIC), a field-programmable gate array (FPGA), or equivalent discrete or integrated logic circuitry adapted for using the method of the first, second, third, fourth, fifth and sixth aspects of the invention. In any embodiment of the first, second, third, fourth, fifth and sixth aspects of the invention, the processor can include multiple components, such as any combination of one or more microprocessors, one or more controllers, one or more DSPs, one or more ASICs, or one or more FPGAs, as well as other discrete or integrated logic circuitry. The functions attributed to the processor may be embodied as software, firmware, hardware or any combination thereof. In particular, any processor contemplated by the first, second, third, fourth, fifth and sixth aspects of the invention can have a microprocessor configured to obtain the physiological parameters and make the necessary calculations for the hazard function stored in memory. In particular, the processor may receive data from sensors contained in an implantable biomedical device while operating in a patient and described by the present formulae of the invention and provide alerts or messaging via wireless control to base module connected wirelessly to the implantable device. In any embodiment of the first, second, third, fourth, fifth and sixth aspects of the invention, the device may provide an audible alert or signal an alert during a routine monitoring session. In any embodiment of the first, second, third, fourth, fifth and sixth aspects of the invention, a user and/or clinician can interface and receive the results of the algorithm including the probability of Ventricular Arrhythmia and the calculated hazard function. In any embodiment of the first, second, third, fourth, fifth and sixth aspects of the invention, the adaptive filter can be used to calculate the optimal number and type of physiological parameters.

In any embodiment of the first, second, third, fourth, fifth and sixth aspects of the invention, the communication system allows transferring any data, including the data from the sensors to the processing unit. The communication system also allows the communication of the estimated arrhythmia risks and patient outcomes. In any embodiment of the first, second, third, fourth, fifth and sixth aspects of the invention, a telemetry module having any suitable hardware, firmware, software or any combination thereof known to those of ordinary skill for communicating with another device, can transmit the probability of Ventricular Arrhythmia and the calculated hazard function or any other calculation obtained from the medical device or data records. Under the control of the processor, the telemetry module can receive downlink telemetry from and send uplink telemetry to a programmer or a base module with the aid of an antenna, which may be internal and/or external. The processor can also provide the data to be uplinked and the control signals for the telemetry circuit within the telemetry module via an address/data bus. In any embodiment of the first, second, third, fourth, fifth and sixth aspects of the invention, the telemetry module can provide received data to the processor via a multiplexer or any other suitable methods and systems. In any embodiment of the first, second, third, fourth, fifth and sixth aspects of the invention, a telemetry module can communicate with the processor in the implanted biomedical device using RF communication techniques supported by telemetry modules known to those of ordinary skill.

In any embodiment of the first, second, third, fourth, fifth and sixth aspects of the invention, the processor can transmit the probability of Ventricular Arrhythmia and the calculated hazard function and any other obtained measurement or calculated values to a programmer or base module. In any embodiment of the first, second, third, fourth, fifth and sixth aspects of the invention, the programmer or base module may electrically interrogate the processor or implantable biomedical device as needed. The processor and/or implanted biomedical device can store the probability of Ventricular Arrhythmia and the calculated hazard function and/or calculated values within memory and retrieve the stored values from memory upon receiving an instruction from a programmer or base module. The processor may also generate and store data containing the obtained calculations based on the measurements collected from the sensors or data records and transmit the data to programmer or base module upon receiving instructions. In any embodiment of the first, second, third, fourth, fifth and sixth aspects of the invention, data from the sensors, the processor, or implanted biomedical device may be uploaded to a remote server on a regular or non-regular basis where a clinician or program may access the data to determine whether a potential life threatening or hazardous event due to the probability of Ventricular Arrhythmia and the calculated hazard function exists. An example of a remote server includes the CareLink Network, available from Medtronic, Inc. of Minneapolis, Minn.

The technical benefits of the real-time monitoring described herein provide for immediate adjustments to the hazard functions that cannot be accomplished with pen and paper. The changes to the parameters and therefore the changes to the hazard level occur constantly in order to continuously update the hazard level of the patient. These changes occur too quickly for the calculations to be performed with the use of pen and paper.

The processors described herein can be medical device processors. Medical device processors can control the collection of external or implantable medical device data, control the collection of metadata based on the collected data, and synchronize the data on a timeline. The computing unit and the sensors which detect the data in each of the categories are specific purpose computers and processors configured or a medical or healthcare setting. The computers or processors can have shielded circuitry to prevent electric shock to a patient or operator. In any embodiment of the first, second or third aspects of the invention, the computers and processors of the present invention are not general purpose computers and can have regulatory approval for approved medical use on patients. The processors also have communication systems, hardware and software that protect patient privacy by protecting the information obtained from the patient.

The systems described herein can also obtain historical data from electronic medical records or other sources. The hardware configurations of the system allow for transmission of the data obtained to the patient's electronic medical records, or to a hospital data hub, handheld device, or monitor. The computers or processors described herein are specially adapted to receive patient data from the sensors and immediately perform the necessary calculations to determine the probability of a life threatening ventricular arrhythmia.

Sensors

The first, second, third, fourth, fifth and sixth aspects of the invention can have a set of sensors on implantable or external devices to gather physiological parameters from the patient. The sensors can be in communicated or be a part of communication system, which relays information and data between the device, the processing unit, and optionally the patient and the medical care personnel, and a computing unit to process the information. In any embodiment of the first, second, third, fourth, fifth and sixth aspects of the invention, the device can be either implantable or non-implantable depending on the therapy being delivered or the availability of a particular device to obtain data for use in the algorithms of the first, second, third, fourth, fifth and sixth aspects of the invention. For example, an external blood pressure cuff obtaining a digital reading during a therapy session can be used to collect blood pressure data for use by the processor whereas an implanted pacemaker can obtain ECG data in vivo. In any embodiment of the first, second, third, fourth, fifth and sixth aspects of the invention, the device may be specially designed to obtain specific types of data such as an EMG and in other cases can be obtained from non-specifically designed devices such as from the electrodes of an ICD. In general, it will be understood that the sensors used in the first, second, third, fourth, fifth and sixth aspects of the invention can be integral, separate, specially designed or not specially designed to obtain the physiological parameters contemplated by the first, second, third, fourth, fifth and sixth aspects of the invention. The only requirement is that the sensors in whatever form, provide the sources of data necessary for the processing unit to interpret. In one specific example, an implantable medical device, such as cardiac pacemakers, implantable defibrillators and implantable loop recorders can be used to collect data from patients and search for correlations between the physiological signals and patient outcomes, such as a Ventricular Arrhythmia. Electrical impedance of the tissue, number of spontaneous Ventricular Tachycardia (VT) and Ventricular Fibrillation (VF) events per day, time spent in Atrial Fibrillation (AF), and information about the patient's dialysis situation can all be used as factors contributing to the patient's outcome.

The number of spontaneous Ventricular Tachycardia (VT) and Ventricular Fibrillation (VF), collectively defined as VT/VF events, experienced by the patient in a given day can be correlated to the parasympathetic stimulus that the patient has been receiving: the parasympathetic nervous system (PNS) controlling certain aspects of bodily excretion. An increase in the number of spontaneous VT/VF events experienced by the patient in a given day can also indicate an increased trend toward a LTVA. Moreover, Atrial Fibrillation (AF) can also lead to Ventricular Arrhythmias that can be life threatening, e.g. LTVA. An increase in the amount of time spent in AF in a given day, also known as AF burden, can also indicate an increased trend toward a LTVA. Moreover, high levels of potassium in the blood can lead to an increased occurrence of Ventricular Arrhythmias.

Figure 10:
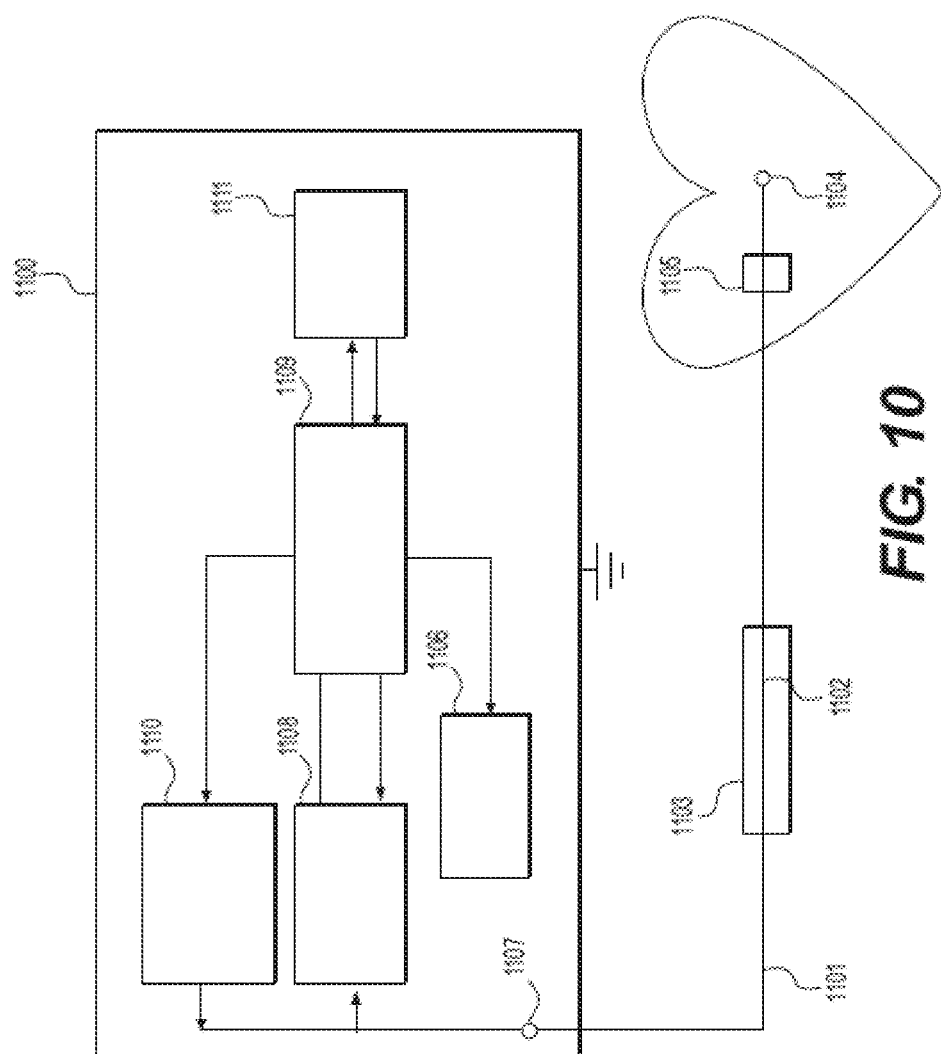
FIG. 10 is a diagram of a pacemaker with a bipolar pacing lead.

In any embodiment of the first, second, third, fourth, fifth and sixth aspects of the invention, the electrical impedance of a tissue can be measured by an implantable device. The impedance can be measured by any of one, two, three, four or more electrodes. In an exemplary one electrode system, the single electrode can be used for both excitation and measurement such as a pacemaker with a bipolar pacing lead. In the case of a pacemaker having a bipolar pacing lead, excitation can be applied between a ring electrode. The measurement can be then taken between the electrode tip and the case wherein the pacemaker case serves as the common electrode. An example of a pacemaker with a bipolar pacing lead is described in U.S. Pat. No. 5,843,135, the contents of which are incorporated herein in their entirety. As shown in FIG. 10, a pacemaker device 1100 can be connected at an output 1107 to a lead 1101. The lead 1101 can extend into the heart and has a tip electrode 1104 and a sensor 1105. The lead 1101 only has a single conductor 1102 to send pacing pulses to tip electrode 1104. The lead 1101 can have a casing 1103 which runs the length of the lead 1101 from the proximal end where it connects to the output 1107 to the distal end where it connects to the tip electrode 1104. The pacemaker provides output pulses from a pulse generator 1106 to the lead 1101. The pulse generator 1106 can be controlled by a timing logic and control block 1109. This block 1109 can be in two way communication with a transmit and receive circuit 1111, which is in telemetric or electrical communication with an external programmer (not shown). Sense processing circuitry 1108 can receive signals from the lead 1101. This circuitry 1108 receives signals and contains other circuitry for the separation of cardiac and sensor information. A square wave current generator 1110 can also be in electrical communication with the timing logic and control block 1109.

Figure 11:
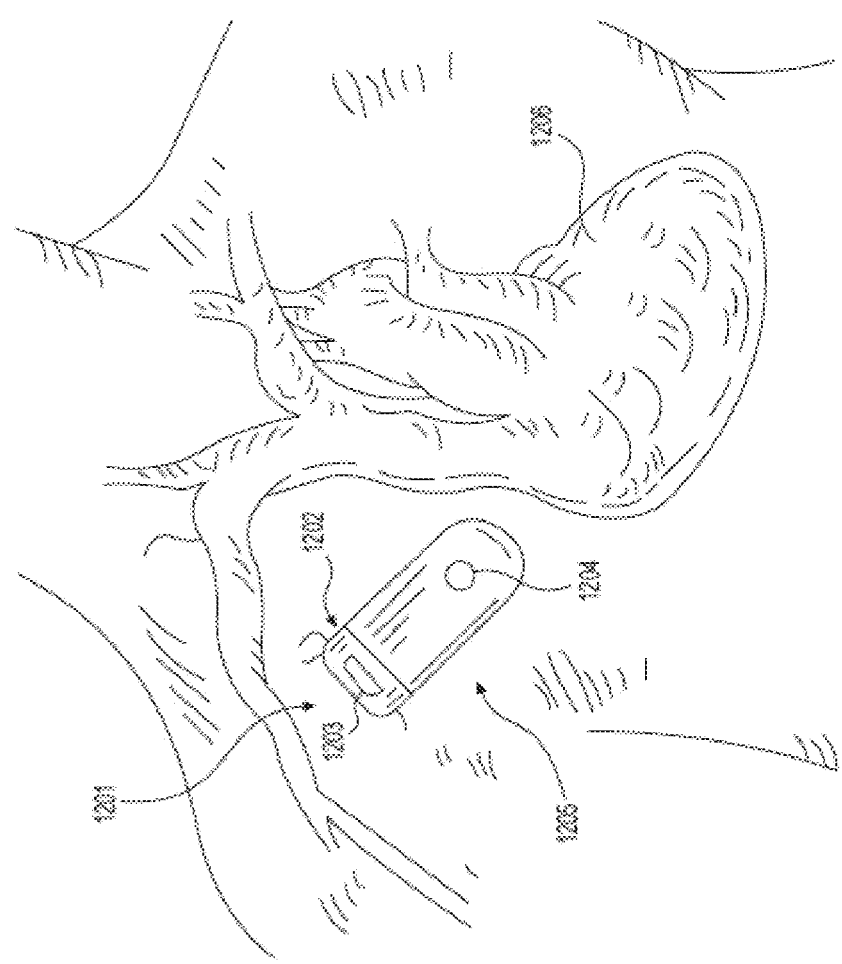
FIG. 11 is a diagram of a two electrode system for impedance measurement.

In an exemplary two electrode system, such as an implantable loop recorder, e.g. Medtronic Reveal, two electrodes can be used both for excitation and for measurement of electrical signals. Aspects of the Reveal insertable loop recorder are disclosed in commonly assigned U.S. Pat. Nos. 5,987,352 and 6,230,059, the contents of which are incorporated herein in their entirety. As shown in FIG. 11, a medical device can have a monitor 1201 implanted in the upper thoracic region of the patient's body, displaced from the patient's heart 1206. The device can have a non-conductive header module 1202 attached to a hermetically sealed enclosure 1205. The enclosure 1205 can contain the operating system of the device. A first subcutaneous electrode 1203 can be formed on the header module 1202, and a second subcutaneous electrode 1204 can be formed by an exposed portion of the enclosure. The conductive housing electrode 1204 can be directly connected to sensing circuitry, while a feed through extends through the mating surfaces of the header module 1202 and the enclosure 1205 to connect the first electrode 1203 to sensing circuitry.

Figure 13:
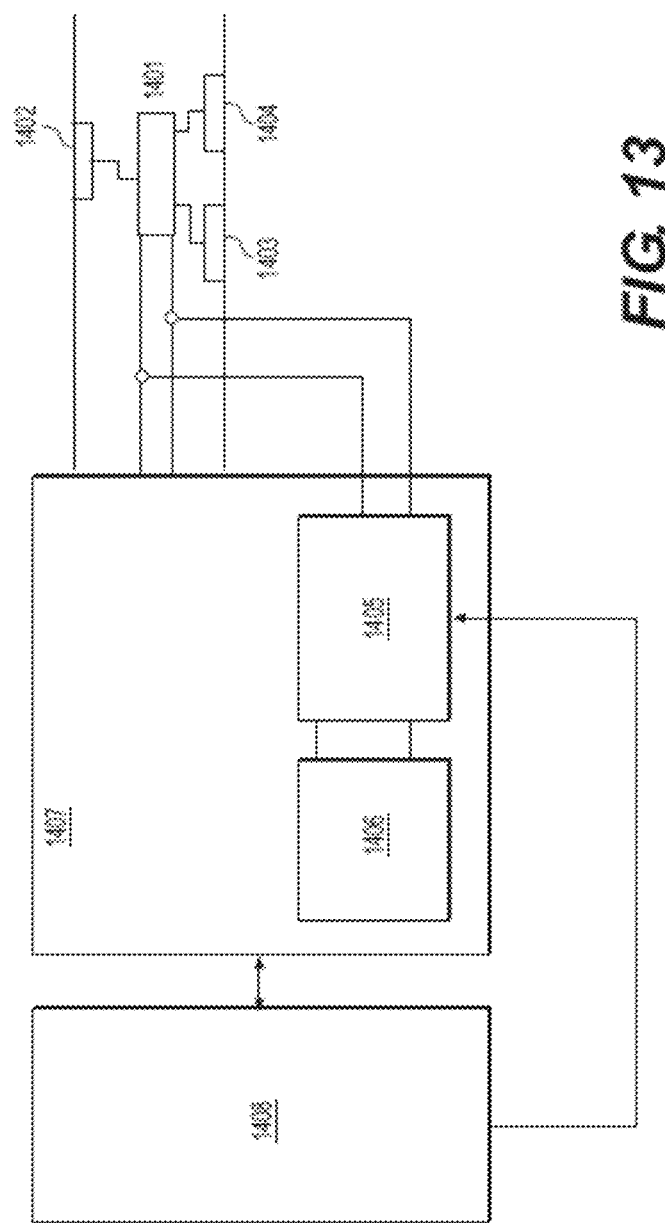
FIG. 13 is a diagram of a three electrode system for measuring impedance.

In exemplary three electrode systems, two electrodes can be used for excitation and one can be used for measurement. A three electrode system capable of measuring impedance is shown in FIG. 13. Lead 1401 can have electrodes 1402, 1403, and 1404, and can attach to an impedance measurement module 1407. The electrodes 1402, 1403, and 1404, and impedance measurement module 1407 can be in electronic communication with and can be controlled by a switching system 1405. The switching system 1405 can be in electronic communication with a stimulation circuit 1406 and a processor 1408. In any embodiment of the first, second, third, fourth, fifth and sixth aspects of the invention, the processor 1408 can be connected directly to the switching system 1405. For measuring impedance, two of the electrodes 1403 and 1404 can be used for stimulation connected to the impedance measurement module 1407. The lead 1401 can be connected to both the impedance measurement module 1407 as well as the switching system 1405. The third electrode 1402 can be used for measurement and can be connected to the lead 1401 wherein the impedance measurement module 1407 collects data from the third electrode 1402.

Figure 14:
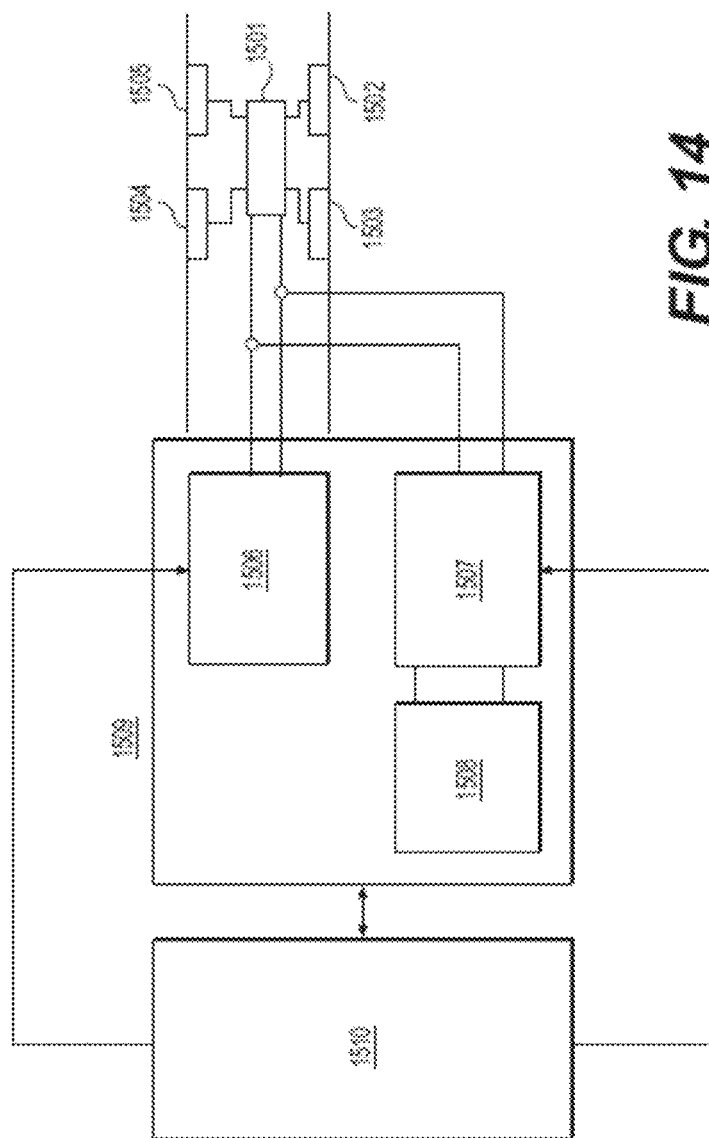
FIG. 14 is a diagram of a four electrode system for measuring impedance.

In an exemplary four electrode system, a separate pair of electrodes can be used for both excitation and measurement; such systems can be more commonly used in external devices. One example of a four electrode system is shown in FIG. 14. Lead 1501 contains four electrodes, 1502, 1503, 1504, and 1505. The electrodes 1502, 1503, 1504, and 1505 can be electronically connected to switching arrays 1506 and 1507 located within the impedance measurement module 1509. A source generator 1508 can be in direct electrical communication with the switching array 1507. In any embodiment of the first, second, third, fourth, fifth and sixth aspects of the invention, the source generator 1508 can be in direct electrical communication with the switching array 1506, the particular arrangement depending upon which pair of electrodes is being used to provide electrical stimulation. The impedance can be measured between any two of the electrodes as determined by the switching arrays 1506 and 1507. The information from the impedance measurements from impedance measurement module 1509 can then be transferred to the processor 1510. In any embodiment of the first, second, third, fourth, fifth and sixth aspects of the invention, the processor 1510 can be connected directly to the switching system 1506.

In any embodiment of the first, second, third, fourth, fifth and sixth aspects of the invention, electrical excitation can be in the form of a sinusoidal or in the form of a step function, e.g. pulse. The frequencies for such signals can range from 16 Hz to 200 KHz, with a current amplitude of 10 micro-Amps or more. In any embodiment of the first, second, third, fourth, fifth and sixth aspects of the invention, excitation can be generated by a constant current or a constant voltage source, and can be applied continuously or periodically to prolong the battery life. Circuitry within the implantable device can measure the response from the tissue and calculate the magnitude of the electrical impedance, which has a base value usually in the range of 100 Ohms to 1,000 Ohms. In any embodiment of the first, second, third, fourth, fifth and sixth aspects of the invention, the electrical impedance can range from any of 25 to 100, 25 to 250, 25 to 500, 25 to 1,000, 25 to 1,250, 50 to 100, 50 to 250, 50 to 500, 50 to 1,000, 50 to 1,250, 100 to 250, 100 to 500, 100 to 1,250, 100 to 1,500, 500 to 1,000, 500 to 1,500, 500 to 2,000, 750 to 1,250, 750 to 1,500, 750 to 2,000, 1,000 to 1,250, 1,000 to 1,500, 1,000 to 2,000, 1,000 to 2,500, and 1,500 to 2,000 Ohms. The expected changes in the tissue impedance are usually less than 10% of its base value. Any such expected changes of a calculated value are contemplated by the first, second, third, fourth, fifth and sixth aspects of the invention. An implantable device can store an entire impedance trace or a representative value, such as a daily average, for further processing by the computing unit. Alternatively, the implantable device may transmit the raw data to an external unit, and the external unit may store and process that data.

In any embodiment of the first, second, third, fourth, fifth and sixth aspects of the invention, a spontaneous VT/VF event can be detected by an ECG processing circuitry of the device. The ECG can be sensed by the electrodes on the device as performed by an implantable loop recorder such as Medtronic Reveal and leadless pacing systems that can be deployed in the right ventricle, or with the aid of electrodes on the leads as in the case of implantable pacemakers, defibrillators, cardiac resynchronization devices or subcutaneous defibrillators. In any embodiment of the first, second, third, fourth, fifth and sixth aspects of the invention, ventricular rhythm can be classified by the device or processor based on certain programming parameters. For example, a physician or programmer may program the device to classify three or more sequential beats that originate from the ventricle at a rate of more than 100 beats per minute as a Ventricular Tachycardia (VT). An implantable device may record the entire electrogram trace for the Ventricular Arrhythmic (VA) event, or some information such as the rate and duration of the arrhythmia, or simply the number of arrhythmic events in a given day.

In any embodiment of the first, second, third, fourth, fifth and sixth aspects of the invention, Atrial Tachycardia (AT) and Atrial Fibrillation (AF) can be detected by the ECG processing circuitry of the implantable device. As described above, the ECG can be sensed solely by the electrodes placed on the device or with the aid of electrodes that are on the leads attached to the implantable medical device. In any configuration, a lead can be attached to the atrium where the implantable medical device senses the electrical activity of the atrium and processes the signals to detect atrial arrhythmias such as AT and AF. When there is no atrial lead, the detection of AT can use a pseudo ECG recorded by the electrodes on the implantable medical device by searching for P-waves or monitoring a ventricular electrogram for irregularities caused by atrial arrhythmias conducted from an atrium to a ventricle. In any embodiment of the first, second, third, fourth, fifth and sixth aspects of the invention, the implantable device can record the entire electrogram trace for the atrial arrhythmic event, or obtain information such as the rate and duration of the arrhythmia, or the total time spent in AT/AF during a given day.

In any embodiment of the first, second, third, fourth, fifth and sixth aspects of the invention, information related to whether hemodialysis treatment was received during a day can be entered manually, communicated electronically from a medical system, such as an electronic health record or the dialysis management system, or imputed by the implantable medical device. Although manual entry and the retrieval from an electronic system are simple options, they may not be always available. In that situation, the implantable medical device can inspect the daily impedance values and interpret a rise in the impedance value as an indication of a reduction of the fluid volumes resulting from a dialysis session. In any embodiment of the first, second, third, fourth, fifth and sixth aspects of the invention, the processing unit can check the calendar to determine if the patient is scheduled to receive dialysis on a particular day. Insofar as most dialysis patients maintain a fixed schedule, such as receiving three dialysis sessions per week on either Monday, Wednesday, and Friday or Tuesday, Thursday, and Saturday of each week, the processing unit can store data according to such schedules or any combination of days thereof.

Example 1

Figure 4A:
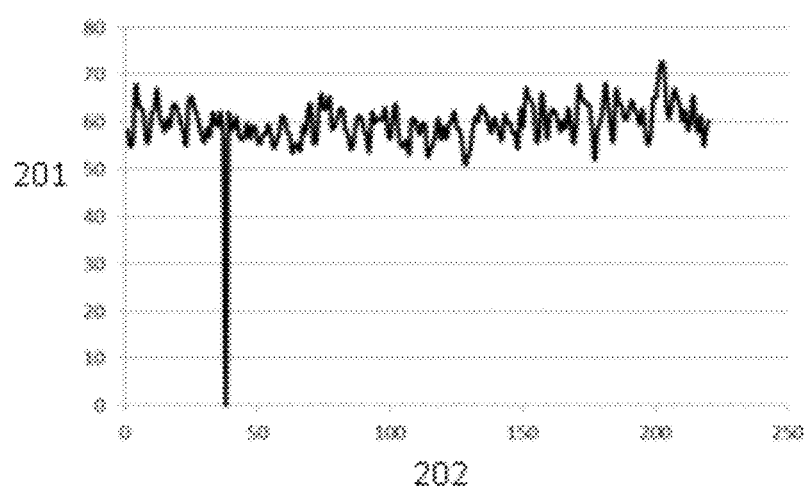
FIG. 4a is a tracing of the daily impedance for a patient in the time domain.
Figure 4B:
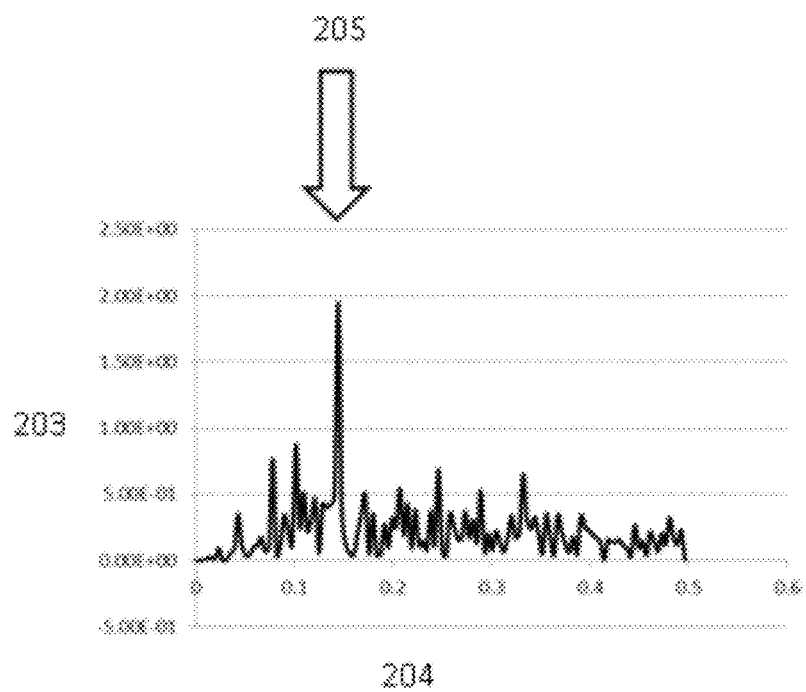
FIG. 4b is a tracing of the daily impedance for a patient in the frequency domain.
Figure 5:
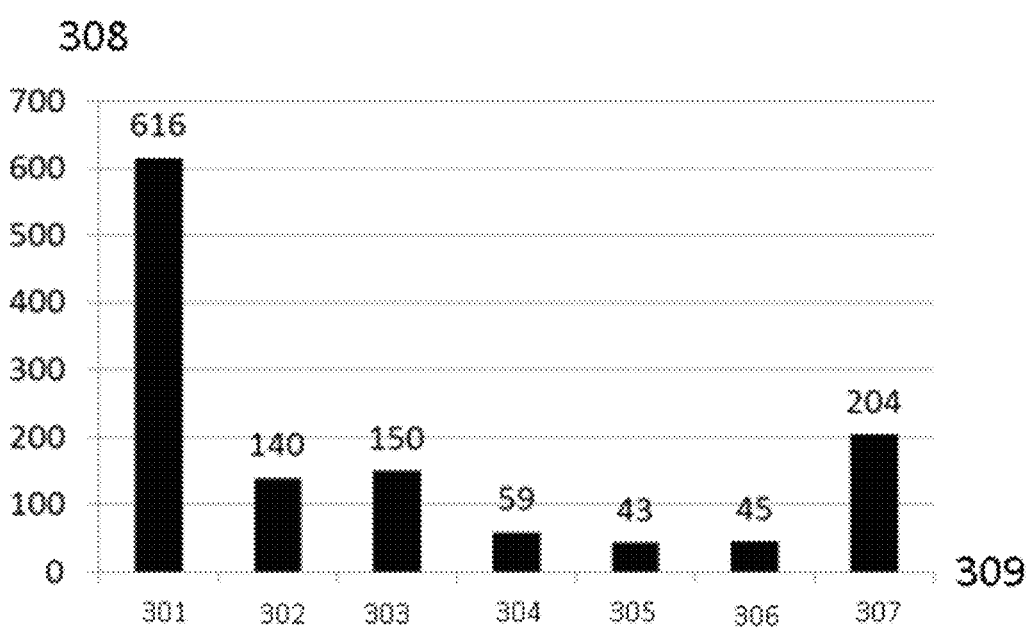
FIG. 5 is a histogram showing the day of the week that the minimum tissue impedance is observed in a 1,257 patient data set.

A database containing transmissions from patients with implantable medical devices was used. In this database, a search was carried out to search for individuals having a weekly pattern in their electrical impedance trace as shown in FIG. 4a, which shows the daily impedance 201 plotted against time in days 202. Without being limited to any theory, it is hypothesized that mild fluid overloads are experienced during the long interdialytic period of the hemodialysis patients, usually on the weekends, manifest themselves as drops in the impedance values on Sundays. The presence of a weekly pattern in the daily impedance was confirmed by a peak at a frequency of 1/7 reciprocal days in the power spectrum, as shown in FIG. 4b, which plots the power 203 against reciprocal days 204. The arrow at 205 corresponds to a peak frequency at 1/7 days. At the end, 1,257 patients with a weekly impedance pattern were identified in the dataset. FIG. 5 shows a plot of the number of patients 308 against the day of the week the patient had the lowest impedance value 309. 301 refers to Sunday, 302 to Monday, 303 to Tuesday, 304 to Wednesday, 305 to Thursday, 306 to Friday, and 307 to Saturday. The graph shows that majority of these patients, 616, have their lowest impedance value corresponding to a volume overload at the end of the weekend, i.e. on Sundays. This fact allows us to infer that for these patients, Sunday corresponds to the longest time period since their last dialysis session.

A closer review of the data from the 616 patients having their lowest daily impedance values on Sundays showed that some patient had missing data which would negatively impact the analysis. Once those patients were removed from the population, a group comprising 593 patients was obtained for the final analysis. Amoeba algorithm applied to the data extracted from all 593 patients selected for the analysis to build a non-adaptive predictive model. One set of values for the nine coefficients, k1 through k9, was determined by minimizing the prediction error for each patient. Afterwards, mean and median values were determined for each of the nine coefficients, k1 through k9. Finally, the model was run with these fixed coefficients and the outcomes were inspected. Results of this evaluation are shown in FIGS. 6a, 6b and 6c.

Figure 6A:
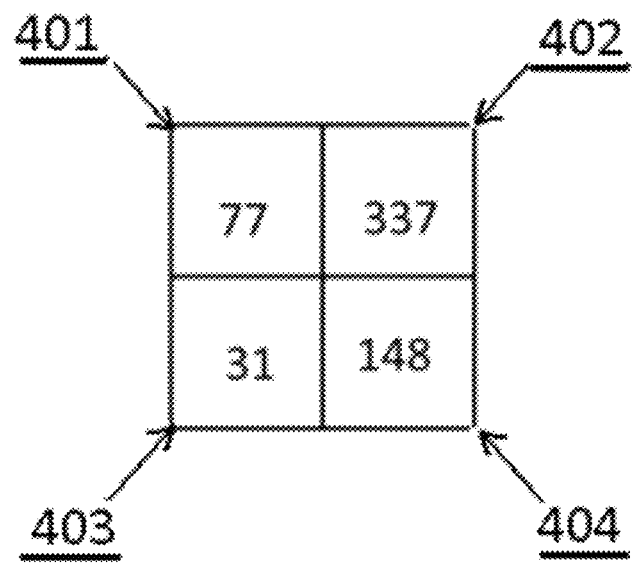
FIG. 6a is the result of the non-adaptive predictive model when the mean values of the coefficients are used.
Figure 6B:
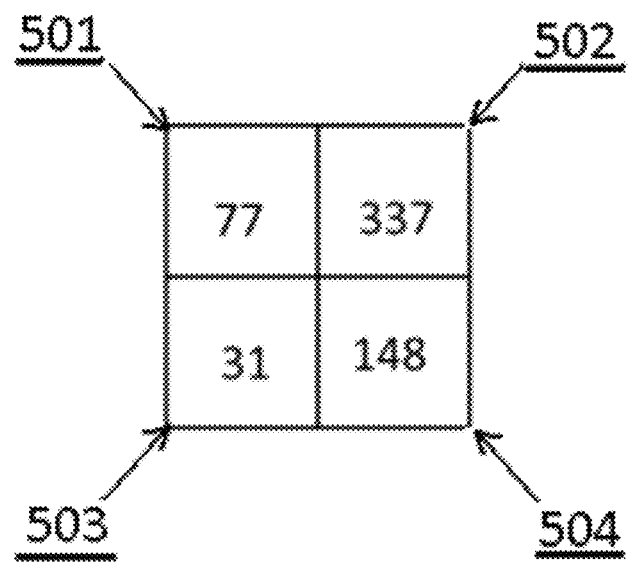
FIG. 6b is the result of the non-adaptive predictive model when the median values of the coefficients are used.

FIG. 6a shows the results where the mean values of the nine coefficients were used. The box labeled 401 shows the number of true positive results, 402 shows the number of false positive results, 403 shows the number of the false negative results, and 404 shows the number of the true negative results. FIG. 6b shows the results when the median values of the nine coefficients are used. The box labeled 501 shows the number of true positive results, 502 shows the number of false positive results, 503 shows the number of the false negative results, and 504 shows the number of the true negative results. FIG. 6c shows the present situation where hemodialysis patients do not receive device based treatments.

Figure 6C:
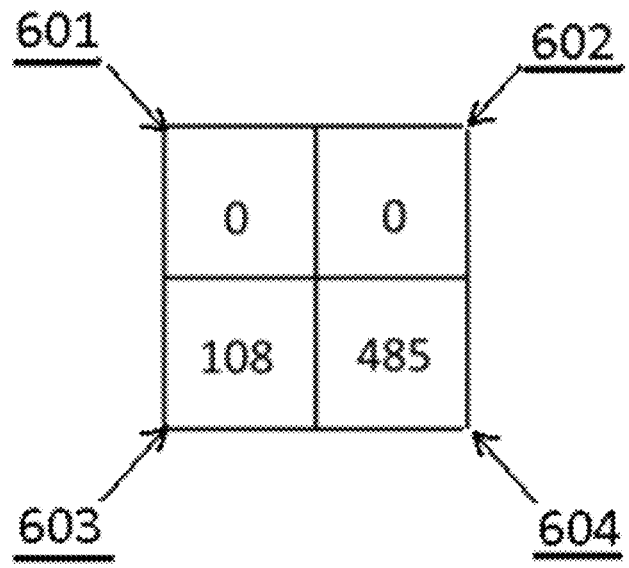
FIG. 6c is the result of the trivial case where no test is done and no patient is selected for treatment.

To help interpret the performance of the non-adaptive algorithm, the current medical treatment option was also evaluated, and is shown in FIG. 6c. The box labeled 601 shows the number of true positive results, 602 shows the number of false positive results, 603 shows the number of false negative results and 604 shows the number of true negative results. Because under the current situation patients do not receive device based treatments, all the patients are placed in the negative boxes, 603 and 604. This gives a sensitivity, defined as Sensor equals the number of true positives divided by the sum of true positives and the number of false negatives of 0%. This can give a specificity defined as Specificity equals the number of true negatives divided by the sum of the number of true negatives and the number of false positives of 100%. The positive predictive value of the current treatment option, defined as PPV equals the number of true positives divided by the sum of the number of true positives and the number of false positives is undefined, as no patient is selected for treatment. The negative predictive value, defined as the number of true negatives divided by the sum of the number of true negatives and the number of false negatives can be 81.2%.

By contrast, and in one specific example, the sensitivity when using the mean values of the coefficients is 37.96%, and the specificity is 72.96%. This method gives a positive predictive value of 23.16% and a negative predictive value of 16.11%. When the median values of the coefficients are used, the sensitivity is 71.30%, with a specificity of 30.52%. This gives a positive predictive value of 18.60% and a negative predictive value of 17.32%.

In this trivial case, sensitivity of the test is zero, as no patient is selected for treatment. In addition, specificity was shown to be 100%, as all the patients who do not need treatment are correctly denied therapy. These observations bring out few important points:

(1) by doing no test, one can achieve 100% specificity because no patient is selected for treatment. Therefore, any new test would have a difficult time measuring up to the status quo if the goal improves specificity; and (2) Since the no test results in the selection of no patients, sensitivity value is zero, meaning that none of the patients needing treatment can be being identified. Hence, improvements in patient identification can be achieved easily by almost any test.

Figure 7A:
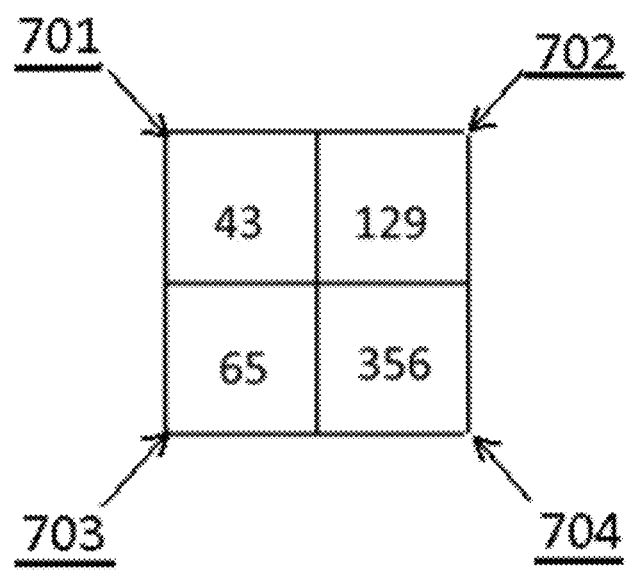
FIG. 7a is the result of the adaptive predictive model where the mean values of the coefficients are used.
Figure 7B:
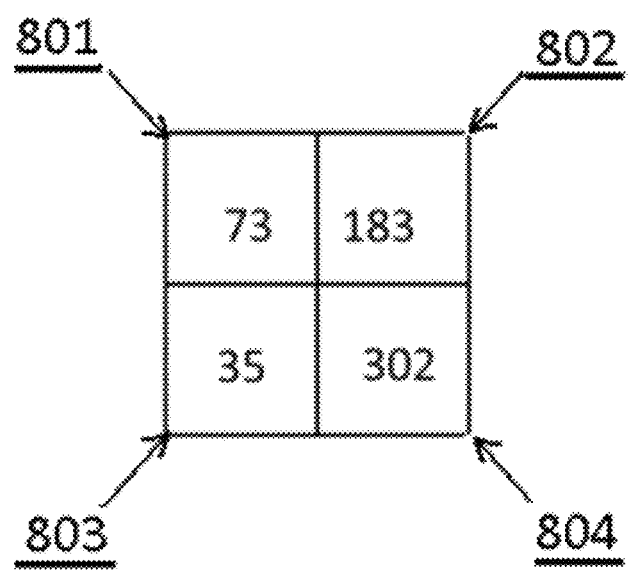
FIG. 7b is the result of the adaptive model when the median values of the coefficients are used.

Once the model using the adaptive filter was applied to the data from the group of 593 patients, the results shown in FIGS. 7a and 7b were obtained. Briefly, when the initial values given to the model were the mean values of the parameters determined earlier, the results shown in FIG. 7a were obtained. The box labeled 701 shows the number of true positive results, 702 shows the number of false positive results, 703 shows the number of false negative results and 704 shows the number of true negative results. Similarly, when the median values of the parameters determined earlier were used as the starting values, the results shown in FIG. 7b were found. The box labeled 801 shows the number of true positive results, 802 shows the number of false positive results, 803 shows the number of false negative results and 804 shows the number of true negative results.

Using the mean values of the coefficients as the initial values give a sensitivity of 39.81% and a specificity of 73.40%. This method had a positive predictive value of 25.00% and a negative predictive value of 15.14%. Using the median values of the coefficients as the initial values gave a sensitivity 67.59% and a specificity of 67.27%. This method had a positive predictive value of 28.52% and a negative predictive value of 10.39%.

Results shown in FIG. 7 can be interpreted by focusing on the data shown in FIG. 7b. In that case, the model was started with a fixed set of values for the parameters k1, k2, k3, k4, k5, k6, k7, k8, and k9, any of which could vary at each step along the way to reduce the error at the time. This method produced a test with sensitivity and specificity values over 60%. As mentioned earlier, the focus can be on the sensitivity measure, which was calculated to be 67.58% in this example. However, the number needed to treat (NNT) to save a life is $(73+183)/73 \approx 3.5$, which is a reasonable number for a lifesaving therapy. The NNT value is significantly lower than what it would have been if all the patients were to be treated, that is $(108+485)/108 \approx 5.5$.

The study was carried out using electrical impedance of the tissue, number of spontaneous ventricular tachycardia and ventricular fibrillation events per day, time spent in atrial fibrillation and information about patient's dialysis situation as the input parameters. The information about the patient's dialysis situation was inferred by the periodic fall of the tissue impedance measurements.

Figure 8:
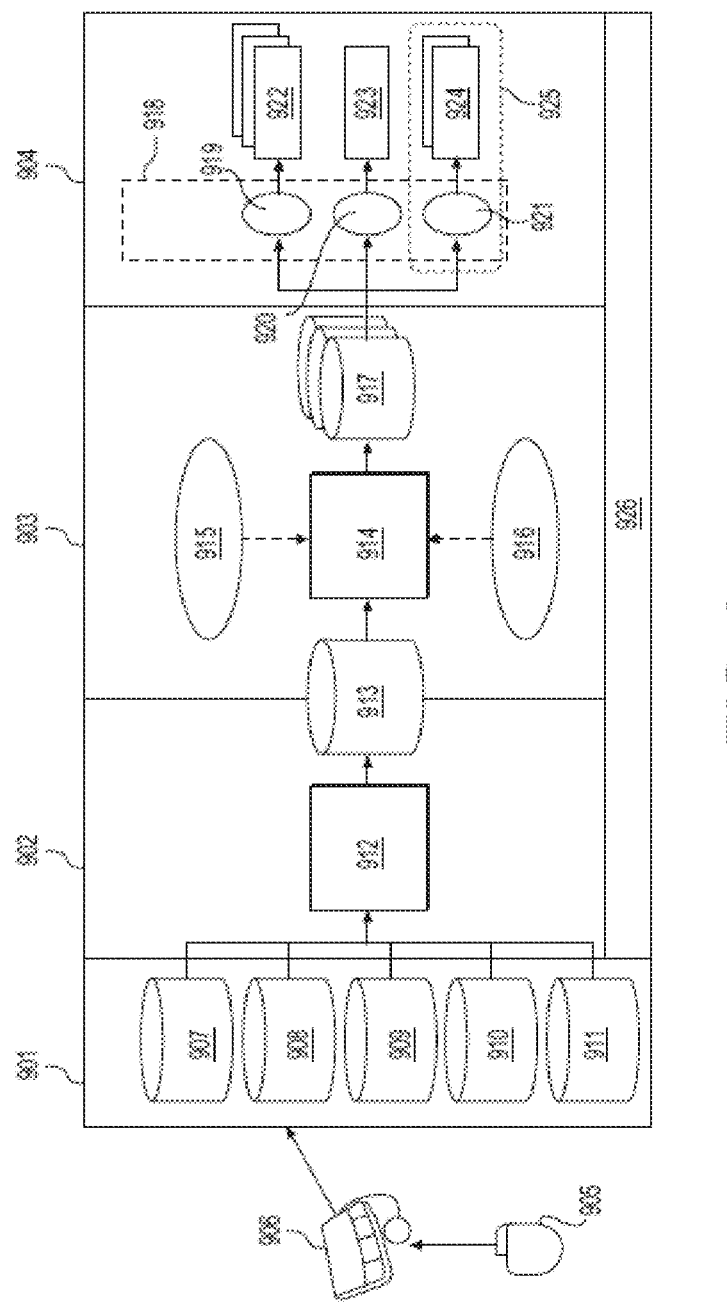
FIG. 8 is a block diagram of the Medtronic Carelink® System.

The information obtained by the sensors and algorithm can be integrated into a system for remote monitoring and analysis, allowing easier use for the patient and caregivers. One example of such a system is the Medtronic CareLink® Network and DWAS system. This system is described in FIG. 8. The information from the implantable device 905 can be transmitted to a remote monitor 906, which can then upload the information into the system. This data can then be stored with information from all data sources 901, including enrollment data 907, follow-up data 908, device and registrant tracking data 909, consumer data 910, and other data sources 911. The data can then be transferred to a data collection subsystem 902. This subsystem can extract, transform and load the data 912, into a source warehouse 913. Copies of the data subsets 914 can be distributed by the data distribution subsystem 903, taking into account appropriate business rules 915 and privacy laws 916. This information can then be transferred to data marts 917. The data from the data marts 917 can then be transferred to a data analysis subsystem 904. The data analysis subsystem then makes data inferences 918, for each of the data marts to give the analyzable data 919, 920 and 921. The data can then be analyzed, including any analytics applications 925, to give analyzed information 922, 923, and 924. All of this can be done utilizing the Data Warehousing and Analytics Services (DWAS) components 926.

Figure 9:
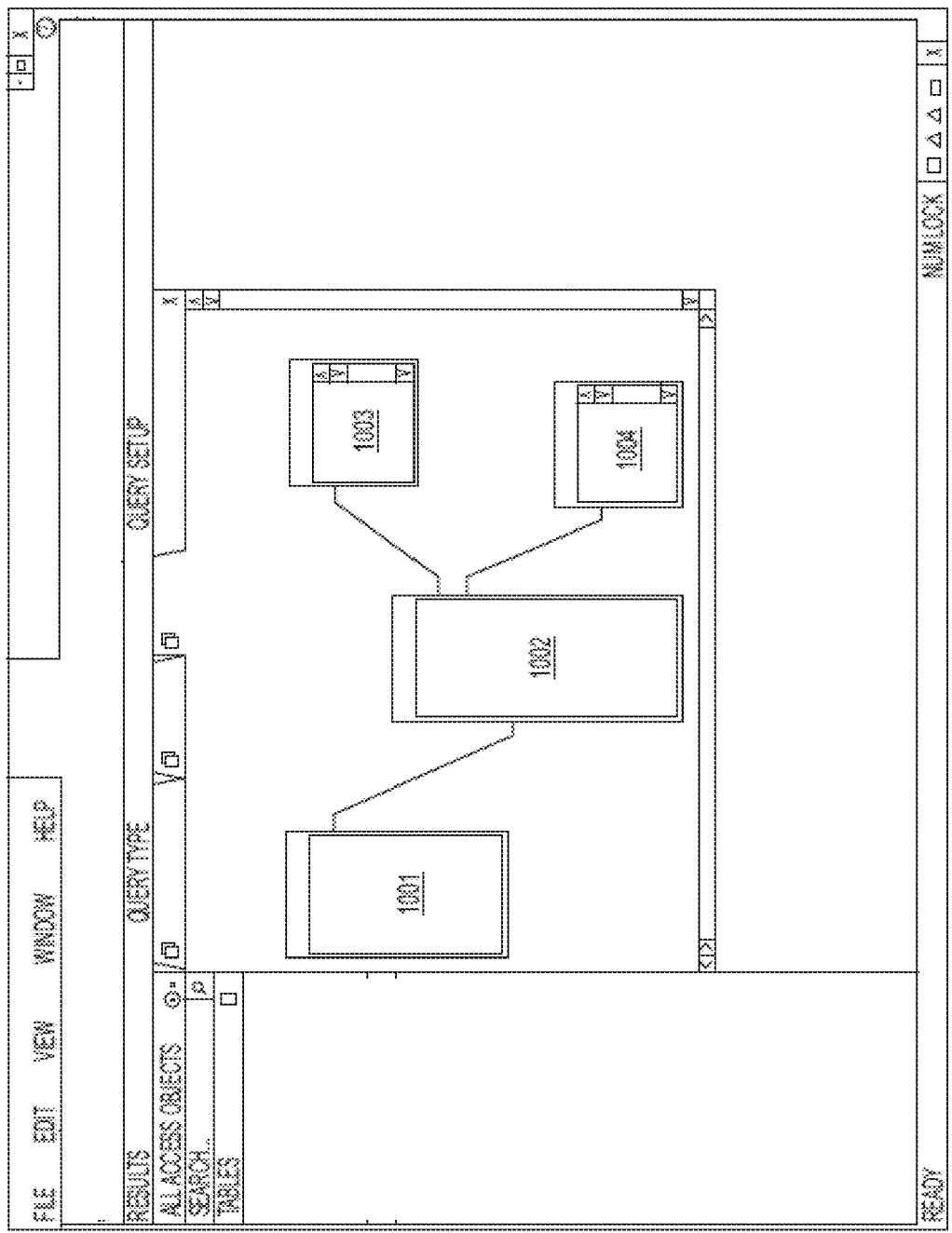
FIG. 9 is a screenshot of a query using the DWAS system.

One benefit of utilizing a system such as the Medtronic CareLink® Network is the ease of access to information. FIG. 9 shows a screen shot of a search of patients using the system. The user need only enter the information required, such as patient age 1001, type of device 1002, or device model 1003, and the length of time for which to search 1004, and a DWAS system can select the patients that match the criteria and provide the necessary data. This allows for analysis of trends, and data necessary for calculating the coefficients based on an aggregate group of similar patients.

One skilled in the art will realize that it is possible to use less than four parameters to estimate the risk of a life threatening ventricular arrhythmia. The first, second, third, fourth, fifth and sixth aspects of the invention can work with fewer parameters, albeit with some loss in sensitivity and selectivity. Additionally, other factors that correlate to a higher risk of a life threatening ventricular arrhythmia may be added to the first, second, third, fourth, fifth and sixth aspects of the invention without going beyond its scope.

Figure 12:
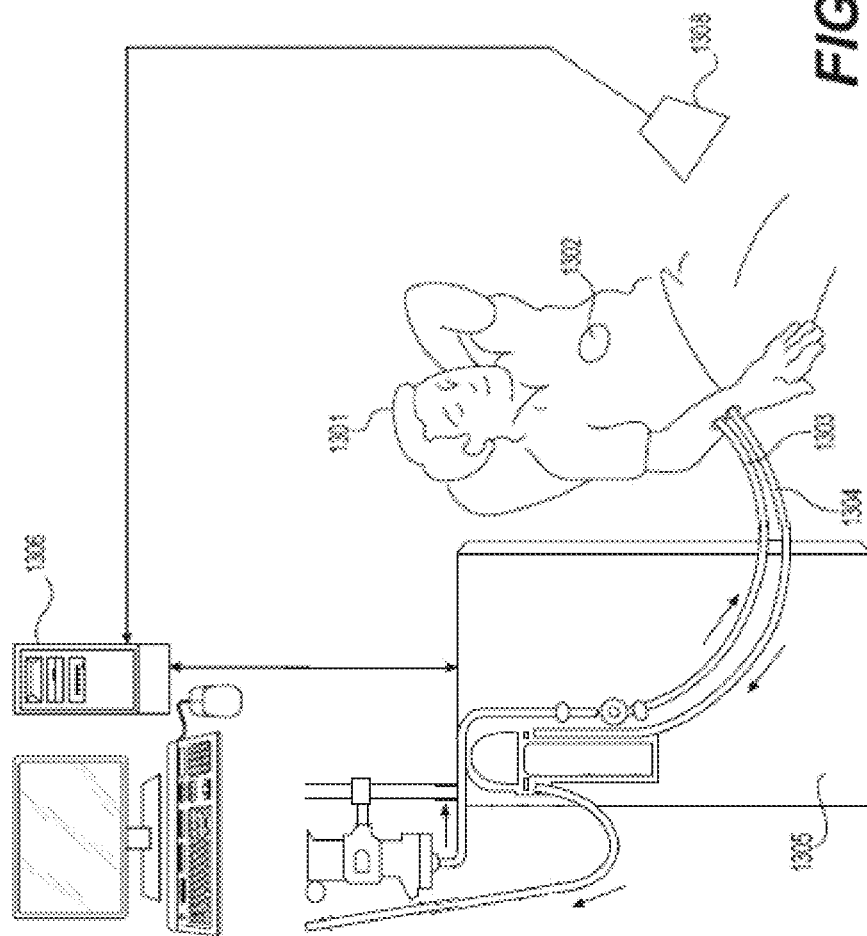
FIG. 12 is a set up of the system for obtaining real time data during a dialysis session.

Real time information from a patient 1301 may be obtained during a dialysis session as shown in FIG. 12. The patient 1301 may have an implantable medical device 1302, examples of which are described herein. The dialysis system 1305 can be connected to the patient via blood lines 1303 and 1304. The dialysis system 1305 may include sensors detecting any number of combination of physiological parameters contemplated by the first, second, third, fourth, fifth and sixth aspects of the invention including, but not limited to mixed venous oxygen saturation, the amount of fluid removed, and dialysis markers such as sodium or potassium using any of the sensors described herein or known to one of ordinary skill for its intended purpose for collecting the relevant data. The information detected by the dialysis system 1305 can be directly uploaded to a processor 1306 wirelessly or through a wired connection, or the information can be read by a user (not shown) and manually entered into the processor 1306. In any embodiment of the first, second, third, fourth, fifth and sixth aspects of the invention, information can be obtained from the implanted medical device 1302 and collected by a receiver 1308 and either directly uploaded into the processor 1306 wirelessly or through a wired connection, or the information read by the user and manually entered into the computer.

It will be apparent to one skilled in the art that various combinations and/or modifications and variations can be made in the dialysis system depending upon the specific needs for operation. Features illustrated or described as being part of one embodiment may be used on another embodiment to yield a still further embodiment.

Medical Monitoring System

The first, second, third, fourth, fifth and sixth aspects of the invention provide for medical monitoring system having one or more implantable medical devices capable of detecting and monitoring a variety of patient medical parameters, as defined herein. Several of these parameters, such as fluid level and incidence of arrhythmia can be affected by dialysis. In order to provide more efficient and precise dialysis treatment and avoid the incidence and/or risk of arrhythmia, the effects of a dialysis session on a patient's physiological parameters can be monitored, analyzed, and displayed. The first, second, third, fourth, fifth and sixth aspects of the invention can accomplish this by providing at least one output from an implantable or non-implantable medical device collecting patient data, which can then be synchronized and/or simultaneously presented with at least one medical parameter and the occurrence of a dialysis session. The dialysis systems or method of the first, second or third inventions can also display dialysis parameter data related to the occurrence of arrhythmia, in conjunction with any medically and clinically pertinent information such as a patient's name, age, electronic medical number. In particular, the relationship between dialysis and physiological data can be especially important and require computation using specific dialysis algorithms.

The synchronized and/or simultaneous presentation of data allows for the analysis and detection of arrhythmia due to the effects of dialysis. The first, second, third, fourth, fifth and sixth aspects of the invention can lead to improved clinical assessment, personalization or customization of therapy delivery, improved therapeutic delivery, and better clinical outcomes and provides significantly more than simply aggregating information. The systems and methods of the first, second, third, fourth, fifth and sixth aspects of the invention further provide for computer-assisted methods for dialysis algorithms capable of implementing clinical action on networked health systems in a secure, HIPAA compliant environment based on any of the collected data. The systems and methods of the first, second, third, fourth, fifth and sixth aspects of the invention can further connect patient data to an Electronic Medical Record (EMR) providing historical data to assist in future dialysis sessions, or can call and receive information from the EMR.

In any embodiment of the first, second, third, fourth, fifth and sixth aspects of the inventions, data can be collected from a patient in between dialysis sessions. The data can be collected continuously or in pre-programmed time intervals. The first, second, third, fourth, fifth and sixth aspects of the invention provide for collecting medical parameter data including the non-limiting group consisting of electromyogram (EMG), an electroencephalogram (EEG), an electrocardiogram (ECG), tissue impedance, blood pressure, the level of specific ions in the blood of a patient, or other data concerning the health of the patient. In any embodiment of the first, second, third, fourth, fifth and sixth aspects of the invention, the systems and methods can analyze the collected data and provide or recommend adjustment of a patient's dialysis prescription. The adjustment can be provided in the form of computer instructions to specially adapted dialysis systems configured to effectuate a change in any number of dialysis parameters such as time of dialysis, flow rate, ion or solute concentration in the dialysis, time in between or number of dialysis sessions, or any parameter impacting a patient's physiological response to dialysis known to those of ordinary skill.

The collected data can be presented in synchronized and/or simultaneous form wherein the collection, presentation, and analysis of such data can assist in evaluation and possible subsequent modification of dialysis induced stressors to reduce incidence and risk of arrhythmia and/or sudden cardiac death (SCD). Aggregating such data, e.g., ECG, is non-trivial and cannot be performed by pencil and paper. The dialysis systems and methods of the first, second, third, fourth, fifth and sixth aspects of the inventions are implemented on specifically adapted computers and processors configured for a medical or healthcare setting. The computers and processors can have shielded circuitry to prevent electric shock to a patient or an operator. In any embodiment of the first, second, third, fourth, fifth and sixth aspects of the inventions, the computers and processors are not general purpose computers and can have regulatory approval for approved medical use on patients. The computer and processors can be use secure communication channels specially adapted to a particular medical device.

In the implanted sensors of the first, second, third, fourth, fifth and sixth aspects of the invention, a critical issue can be battery life. The more sensing and data streaming is required, the faster a battery may be depleted. As such, the first, second, third, fourth, fifth and sixth aspects of the invention can use specially adapted computers, processors and systems to preserve battery life, and to reduce or otherwise optimize an amount of time required for recharging. In any embodiment, the first, second, third, fourth, fifth and sixth aspects of the invention contemplate a safety window for battery life wherein data sensed from a patient having an implantable sensor is not lost. In particular, a prioritization schedule of parameters can be implemented to sense and stream data in order to maintain a battery reserve. For example, as a battery charge reaches a certain minimum threshold, the sensing performed by the implanted sensor can be reduced or performed intermittently at a reduced rate to preserve charge.

Figure 15:
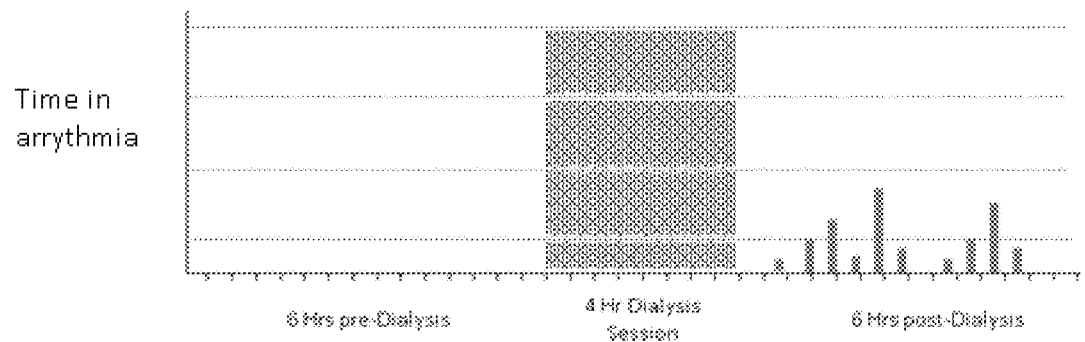
FIG. 15 is a sample display according to one embodiment showing the arrhythmia data of a patient before, during and after a dialysis session.

FIG. 15 shows one, non-limiting embodiment of the first, second, third, fourth, fifth and sixth aspects of the inventions. The output from the medical monitoring system in FIG. 15 is a chart showing the time a patient spent in arrhythmia and the occurrence of a dialysis session. Each hash on the x-axis of the chart corresponds to a period of about 30 minutes. The y-axis shows the time spent in arrhythmia in each time period. As can be seen in FIG. 15, the incidence of arrhythmia was increased for the patient in the time period following dialysis. Such data is important to the health care providers, as the data shows how the patient responds to the dialysis session. If the patient experiences abnormal amounts of arrhythmia events in the time period after a dialysis session, a need to change dialysis parameters and or drug regimens in order to improve patient outcome may be indicated. If the patient experiences abnormal amounts of arrhythmia events in the time period immediately before dialysis, the arrhythmia events could indicate that the patient was experiencing fluid overload between dialysis sessions, possibly indicating that not enough fluid was removed from the patient during the previous dialysis session. The length of time before and after dialysis could be increased or decreased based on the particular time period of interest of the health care provider, and need not be six hours. In any embodiment of the first, second, third, fourth, fifth and sixth aspects of the invention, the data for about 1-4 hours before a dialysis session can be displayed if this data is of more value to the user. In any embodiment of the first, second, third, fourth, fifth and sixth aspects of the invention, up to 8 hours of data after dialysis can be displayed. In any embodiment of the first, second, third, fourth, fifth and sixth aspects of the invention, the user can select the time period before or after each dialysis session to be displayed. In any embodiment of the first, second, third, fourth, fifth and sixth aspects of the invention, the monitoring of the specific parameters can be constant, but the display can show only the time periods the user is interested in. In any embodiments of the first, second, third, fourth, fifth and sixth aspects of the invention, further arrhythmia information can be collected and displayed on the same chart. For example, the height of the bars shown in FIG. 15 can represent the total number of times an arrhythmia started and stopped during the time period, or the number of minutes out of the time period that the patient spent in arrhythmia. The arrhythmia rate can also be included in the data. Further information can include the number of arrhythmia events, the types of arrhythmia or the arrhythmia rate. This information can be included on the same chart by using colors or symbols to indicate the data.

The output shown in FIG. 15 includes a four hour dialysis session. Four hours is a common length of time for a dialysis session. However, one skilled in the art will understand that a dialysis session of any length of time can be shown in the output of the first, second, or third invention. For at-home dialysis, sessions may often be longer, including in the range of 6-8 hours. No matter the length of the dialysis session, the entire session can be shown using the display of the first, second, third, fourth, fifth and sixth aspects of the invention.

By using the data shown in FIG. 15, the user can determine if the previous dialysis session resulted in arrhythmias. If the previous dialysis session resulted in arrhythmias, the system of the first, second, third, fourth, fifth and sixth aspects of the invention can warn the health care provider if the patient started over the target fluid level, had excess fluid removed, if the session ended below the target fluid level or any other parameters that may be out of range. In any embodiment of the first, second, third, fourth, fifth and sixth aspects of the invention, these parameters can be included in the same output as arrhythmia data. For example, out of range parameters can be noted by a symbol or color change in the chart. The output can also note whether arrhythmias have occurred just prior to the current dialysis session. If high fluid levels are noted as well, the high fluid levels could inform or warn the health care provider that extra fluid may have caused arrhythmias in the patient, and that the patient should fluid removed to a new target level.

In any embodiment of the first, second, third, fourth, fifth and sixth aspects of the invention, the frequency of measurements of arrhythmia or any other medical parameter can be adjusted based on the observed frequency of arrhythmia events. That is, if the frequency of arrhythmia is found to be increased during a specific time period, the frequency of measurements taken by one or more other medical parameters can be increased during the same time period. This can provide additional data on the underlying cause of the arrhythmia events.

Figure 16:
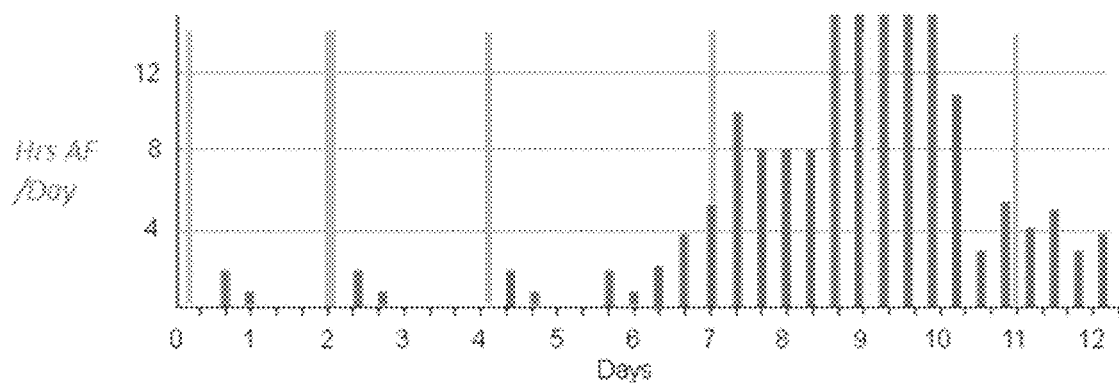
FIG. 16 is a sample display according to one embodiment showing the hours of atrial fibrillation per day and the occurrence of dialysis (shaded bars) for the same patient.

FIG. 16 shows an output including the hours spent in atrial fibrillation per day. The dark lines on the chart in FIG. 16 show the occurrence of a dialysis session. Data from multiple dialysis sessions can be analyzed and the relative risk of arrhythmic event can be displayed for each period of time. As can be seen in FIG. 16, the incidence of atrial fibrillation is increased in the time soon after each dialysis session. The chart in FIG. 16 also shows that the patient had a long interdialytic window during the week, going three days without receiving dialysis, from day 4 to day 7. This can be a common occurrence in dialysis patients, as routine dialysis is often not performed on weekends. After going three days without dialysis, the incidence of atrial fibrillation increased significantly. By providing the medical parameters in this fashion, a care giver can observe the increased incidence of atrial fibrillation due to a longer period without dialysis. The information can provide clinically relevant information concerning the optimal frequency of dialysis for the particular patient, by allowing physicians to see the temporal link between the dialysis and observed arrhythmias. A physician can take steps to reduce the occurrence of arrhythmia. In any embodiment of the first, second, third, fourth, fifth and sixth aspects of the invention, the specially adapted computer and processors used for dialysis can be programmed with algorithms that can adjust one or more dialysis parameters in response to the observed synchronized data. Observation of arrhythmia occurrences before a dialysis session coupled with higher than normal pre-dialysis fluid levels could trigger a longer dialysis session to remove excess fluid. Arrhythmias before a dialysis session without higher than normal pre-dialysis fluid levels could trigger use of lower potassium (or other ion) dialysate concentrations in response to a probable high potassium (or other ion) blood concentration. An observed increase in heart rate or arrhythmia occurrence after the previous session may signal a need to not remove as much fluid as the previous session or to not remove fluid to the same level as in the previous session.

In any embodiment of the first, second, third, fourth, fifth and sixth aspects of the invention, the frequency of measurements of medical parameters such as blood ion concentration or fluid level can be adjusted based on the time duration of arrhythmia events. If the observed arrhythmia events are of a longer time, then the frequency of measurements of other medical parameters can be increased to provide additional information as to the cause of the arrhythmia.

If the incidence of atrial fibrillation is increased during the time periods immediately before or after a dialysis session, the increase in atrial fibrillation would indicate that the events are linked to the dialysis sessions. This information can prompt the health care provider to adjust dialysis session parameters, such as the rate of ultrafiltration or the concentration of solutes provided to the patient during the session. If the incidence of atrial fibrillation is increased during the longer interdialytic window, as shown in FIG. 16, the atrial fibrillation may be caused by fluid overload, and the health care provider may add extra dialysis sessions each week in order to avoid long interdialytic windows.

Changes to dialysis parameters can be selected by choosing a less aggressive method to achieving dry weight, such as a lower blood flow or lower ultrafiltration rate, and then determining the effect of changing the dialysis parameter on arrhythmic events or incidence of atrial fibrillation. If dry weight is determined by fluid measurement, such as by sensing the impedance of a patient, a closed loop optimization can be created to create a smoother fluid removal profile and/or stop therapy if there is a spike in impedance or rise in heart rate driven by volume depletion. In any embodiment of the first, second, third, fourth, fifth and sixth aspects of the invention, changes to dialysis parameters can be determined by a computer. One skilled in the art will understand that algorithms can be created to highlight trends in the medical parameters due to dialysis parameters. Based on the timing of arrhythmic events with respect to dialysis, the computer can automatically cause the dialysis system to change the ultrafiltration rate, blood flow rate or fluid removal target. In any embodiment of the first, second, third, fourth, fifth and sixth aspects of the invention, a computer can make suggestions to the health care providers based on the data.

Figure 17:
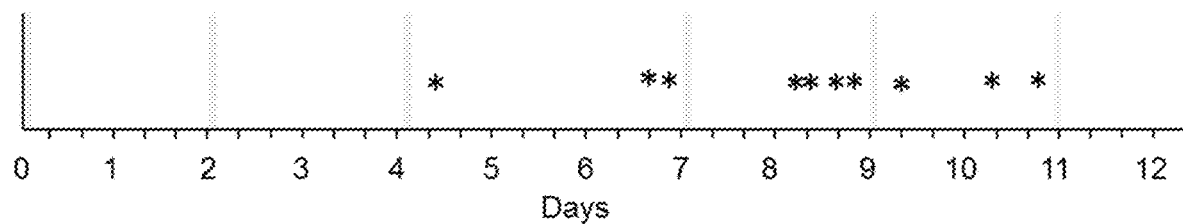
FIG. 17 is a sample display according to one embodiment showing the occurrence of arrhythmia and the occurrence of dialysis for the same patient.

FIG. 17 shows a sample output including the incidence of arrhythmia. The stars on the chart are the times when an arrhythmia was detected. The dark bars show the occurrence of a dialysis session. As can be seen in FIG. 17, after a longer interdialytic window, that is, after three days without dialysis, between days 4 and 7, the incidence of arrhythmia was increased. This display allows the doctors to determine the effect of a longer period of time between dialysis sessions. Arrhythmias may be linked to factors resulting from dialysis, or arrhythmias can be linked to factors that are not related to dialysis. Providing the arrhythmia data with the occurrence of dialysis sessions allows the health care providers to determine the link between the patient's arrhythmias and the dialysis. An increase in arrhythmia prior to a dialysis session, especially after a long interdialytic window, may mean that the arrhythmias are being caused by fluid overload or excessive ion or metabolite build-up during these periods. As a result, the frequency of dialysis could be increased to reduce the occurrence of arrhythmia. Alternatively, more fluid can be removed from the patient during dialysis. The patient's estimated dry weight can be altered in order to remove additional fluid and decrease fluid overload between dialysis sessions. This is especially true if the patient is not experiencing arrhythmias in the periods after dialysis. If the patient is experiencing arrhythmia during or after dialysis, the dialysis parameters can be adjusted to reduce the amount of fluid removed, or reduce the rate at which fluid is removed.

Figure 18:
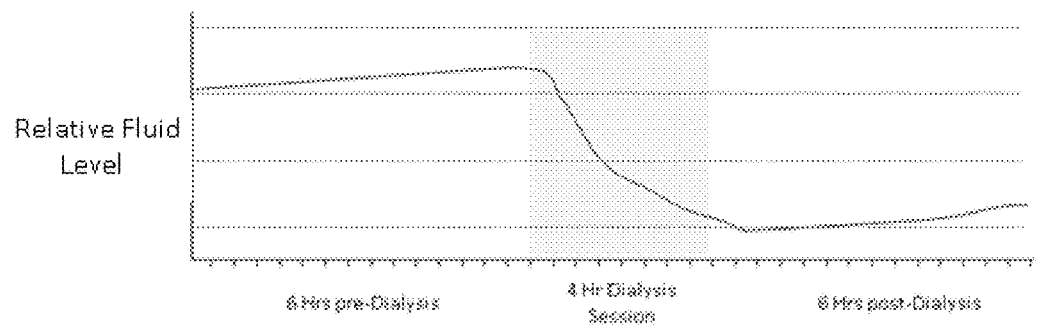
FIG. 18 is a sample display according to one embodiment showing the relative fluid level of a patient before, during and after a dialysis session.

FIG. 18 shows a sample output according to another embodiment of the first, second, third, fourth, fifth and sixth aspects of the invention. The output from the medical monitoring system in FIG. 18 shows the relative fluid level of a patient for a time period including the six hours before a dialysis session, during the dialysis session, and in the six hours after a dialysis session, shown as the inverse of impedance. In any embodiment of the first, second, third, fourth, fifth and sixth aspects of the invention, the relative fluid level of the patient can also be determined by the pre-dialysis and post-dialysis weight of the patient. As is shown in FIG. 18, and as expected, the occurrence of a dialysis session caused a marked change in the relative fluid level of the patient. Fluid in the patient accumulated slowly before the dialysis session, and then quickly dropped during the dialysis session, before slowly increasing after dialysis. In any embodiment of the first, second, third, fourth, fifth and sixth aspects of the invention, arrhythmia or other data such as patient reported symptoms can be superimposed over the fluid level data shown in FIG. 18. Including arrhythmia data on the same chart as fluid level can be useful for clinical diagnosis because the additional information can help to show the link between fluid level and arrhythmia for the particular patient.

In any embodiment of the s first, second, third, fourth, fifth and sixth aspects of the invention, the frequency of measurements by the medical monitoring system can be adjusted based on the fluid level of the patient. For example, if the patient fluid level is significantly higher or lower than the expected patient fluid level, the frequency of measurements for other medical parameters can be increased. Because the patient fluid level can effect arrhythmia or other medical parameters, the frequency of measurements of these medical parameters can be changed when the fluid level of the patient changes.

Figure 19:
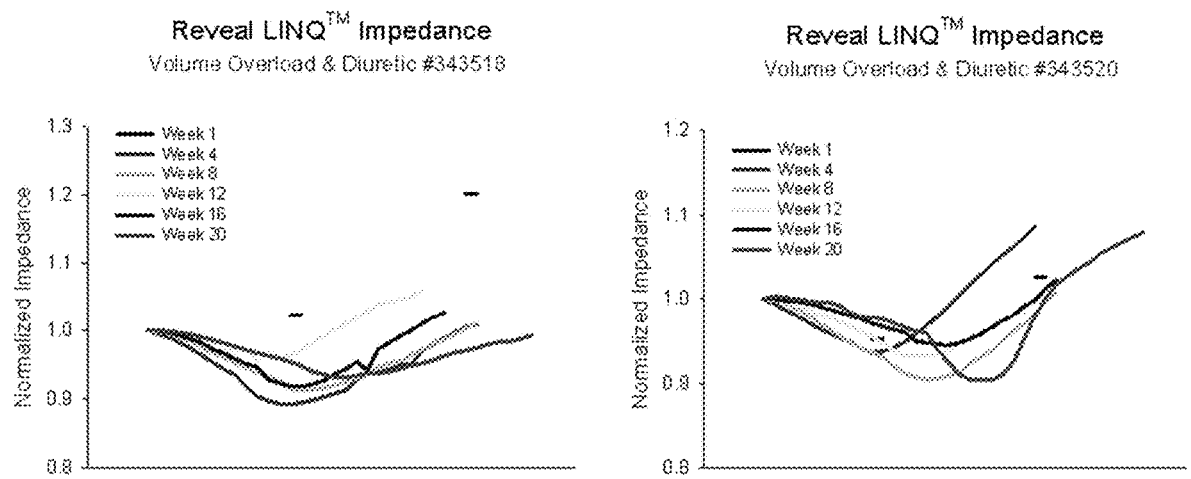
FIG. 19 shows sample impedance value trends corresponding to changes in subject fluid levels.

FIG. 19 shows the effect of fluid level on the measured impedance of a subject. The charts in FIG. 19 show the results of a study measuring the normalized impedance on two different animals with respect to fluid level over the course of several weeks. In each of the charts shown, 1 L of fluid was given to each of the animals each week. As can be seen, after the addition of fluid, the impedance levels dropped dramatically. As urine was excreted by the animals, the impedance levels began to rise back to the normalized level, shown as 1.0 on each of the charts. FIG. 19 shows that the relative fluid level of a patient can be determined based on the measured impedance. Drops in impedance correspond to increases in the relative fluid level of the patient.

Figure 20A:
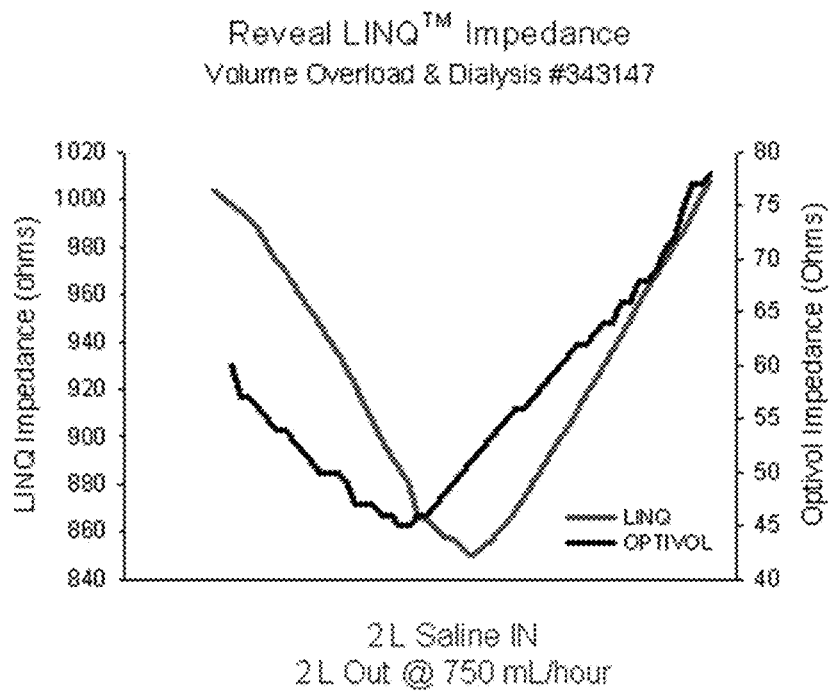
FIGS. 20a-e show sample impedance value trends corresponding to changes in subject fluid levels at a variety of starting impedance values and fluid removal rates.
Figure 20B:
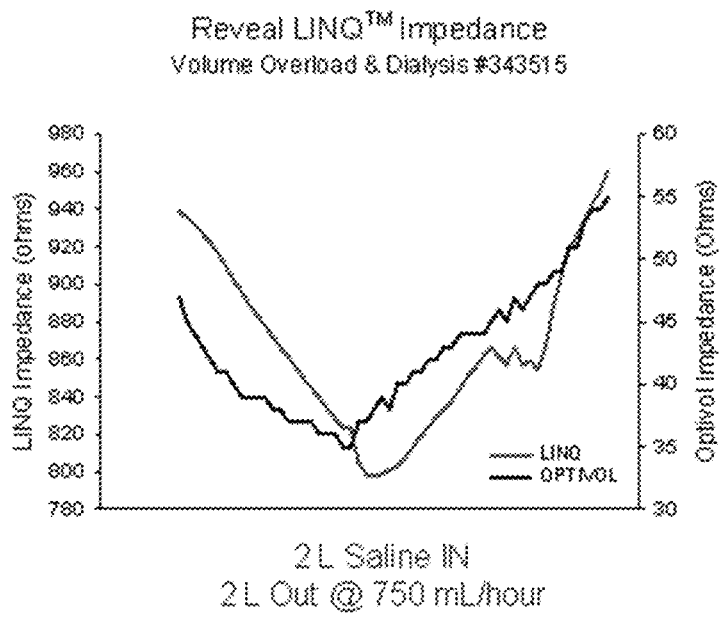
Figure 20C:
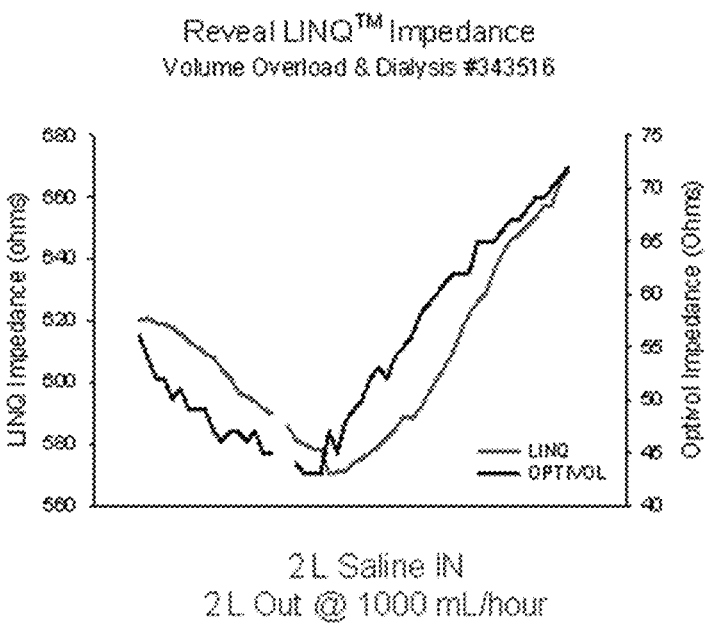
Figure 20D:
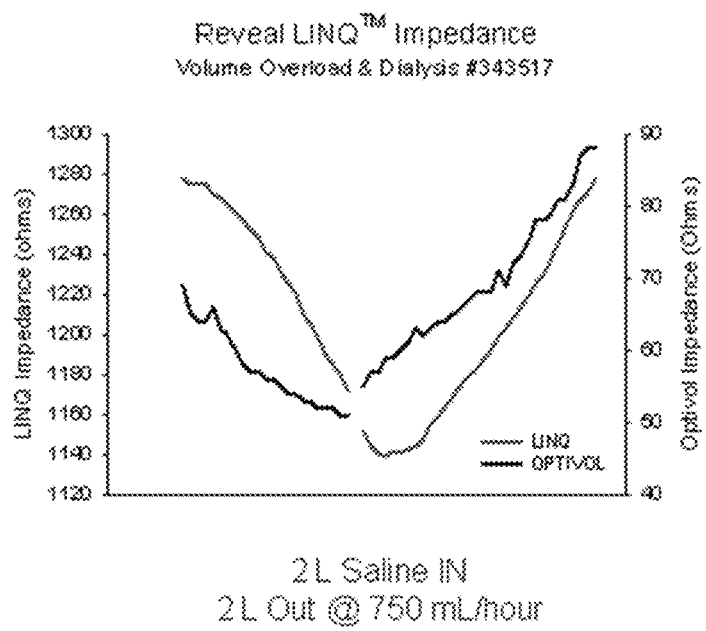
Figure 20E:
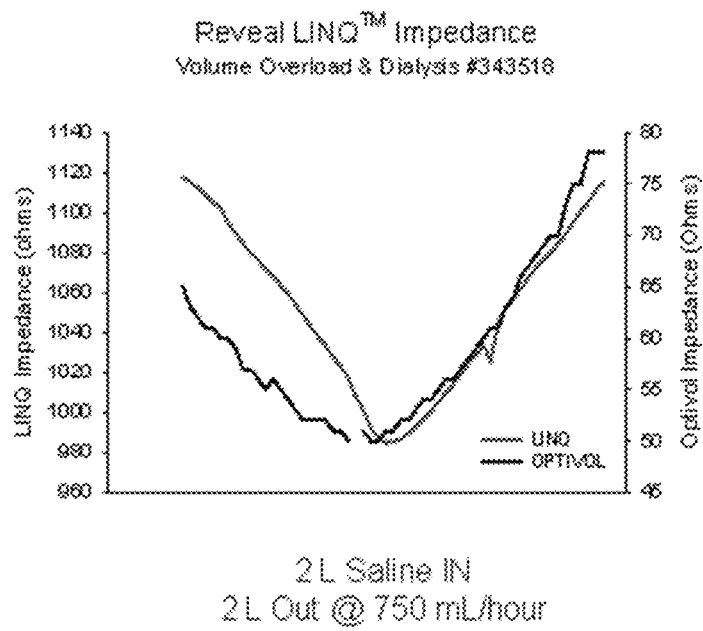

FIGS. 20a-20e show a similar study, measuring impedance with respect to the fluid level of the animal. As with FIG. 19, the subjects shown in FIG. 20 experienced a drop in impedance as fluid was given to the subjects, and then experienced a rise in impedance as fluid was subsequently removed. The charts in FIG. 20 show the actual impedance values obtained in ohms with the Reveal LINQ system. In each of the charts in FIG. 6, 2 L of fluid was infused into the subject over the course of approximately 20 minutes. This corresponds with the initial downward slope of the impedance graphs. The time to remove the 2 L of fluid depends on the rate of fluid removal from the dialysis machine. In FIG. 20c, this rate was 1000 mL/hour removed. For all of the other graphs in FIG. 20, the fluid removal rate was 750 mL/hour. The rate of fluid removal did not alter the fact that the impedance values obtained increased with decreasing fluid of the subject. This can be seen by comparing FIG. 20c, with a fluid removal rate of 1000 mL/hour with the other figures showing fluid removal rates of 750 mL/hour. Likewise, the starting fluid level of the subject did not change the fact that the impedance varied with the fluid level. For example, in FIG. 20d, the starting impedance value with the LINQ system was about 1220 ohms. The effect on impedance due to fluid level for the subject of FIG. 20d was similar to that shown in FIG. 20b, where the starting impedance value was about 890 ohms.

The peak and trough of the charts in FIGS. 19-20 are important to health care providers. These points show the maximum and minimum fluid levels achieved by the subject during the dialysis session. Failure to reach the optimum fluid level for a patient during dialysis may show that the patient is in a non-optimal, or a wet state after dialysis. If the fluid level drops below the optimum level for the patient, there may be an increased risk of arrhythmias, hypotension, HF or other negative symptoms.

Figure 21:
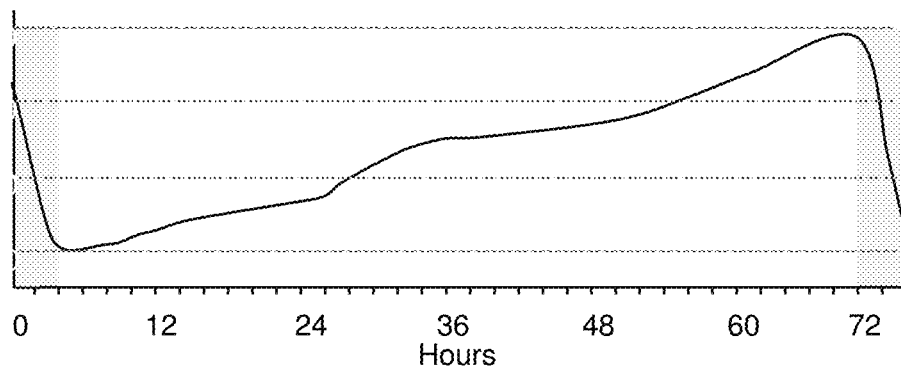
FIG. 21 is a sample display according to one embodiment showing the relative fluid level of a patient between dialysis sessions.

FIG. 21 shows a sample output showing the relative fluid level of a patient between dialysis sessions. The dark bars at the start and end of the chart show the occurrence of a dialysis session. As can be seen, the relative fluid level of the patient increased in the time period between the sessions. An output such as shown in FIG. 21 allows the health care providers to see the rate and amount of increase in fluid level between dialysis sessions. This, in turn, can allow the health care providers to change the dialysis schedule for the patient, counsel the patient on managing their fluid intake or to change the fluid removal prescription. The data in FIG. 21 shows the fluid level of the patient at the end of the previous dialysis session. From this data, the health care provider can determine if the patient arrived at the target weight after the previous dialysis session. The data in FIG. 21 also shows how quickly the fluid level in the patient increased between sessions, and the fluid status of the patient before beginning the current dialysis session. If the patient shows a higher than normal fluid level, or if the patient did not reach the dry weight after the previous dialysis session, the rate of fluid removal can be increased to ensure that the dry weight is reached during the current session. In any embodiment of the first, second, third, fourth, fifth and sixth aspects of the invention, this can be done automatically by a computer in communication with the dialysis machine. In a typical dialysis session, about 2 L of fluid may be removed from a patient. Some larger or non-compliant patients can have more fluid removed, including 6-7 L or more. The output shown in FIG. 21 will enable the physician to determine how much fluid was removed in the previous dialysis session, and to set the target fluid removal amounts and rates accordingly. The rate of fluid increase between dialysis sessions may be due to other factors, such as diet. The ability to see this information clearly can enable the health care provider to identify causes of fluid accumulation and educate the patient on a healthier lifestyle. In any embodiment of the first, second, third, fourth, fifth and sixth aspects of the invention, longer time periods shown in the output display are contemplated. For example, the output display can show the entire week, including if there is a long interdialytic window.

Figure 22:
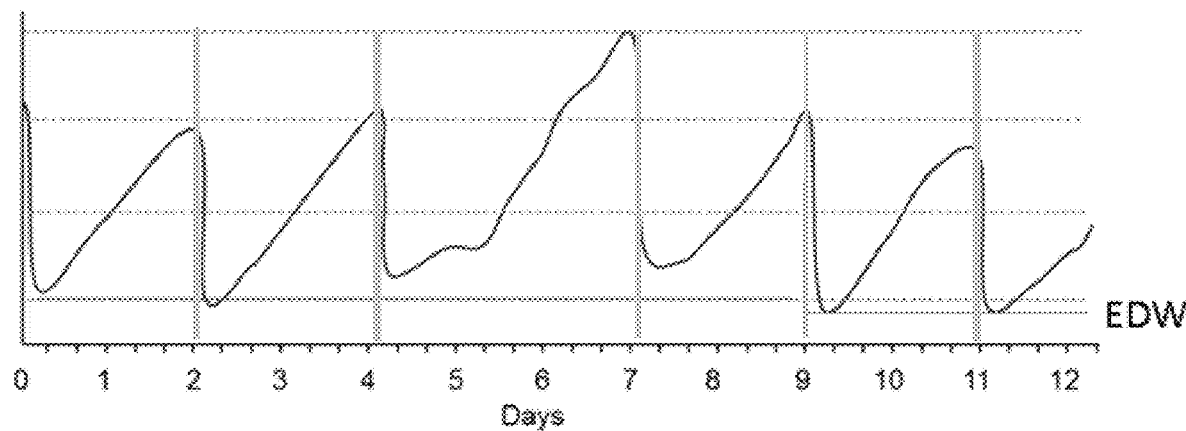
FIG. 22 is a sample display according to one embodiment showing the relative fluid level of a patient for a time period spanning multiple dialysis sessions.

FIG. 22 shows the relative fluid level of a patient over a period of 13 days. The dark bars on the chart show the occurrence of dialysis. The estimated dry weight of the patient is also shown on the graph as "EDW", and taken by the fluid level achieved by the patient during dialysis. Outputs such as shown in FIG. 22 allow the health care providers to determine long-term trends for medical parameters such as the relative fluid level of the patient. The effect of each dialysis session can be quickly noted on the chart because the two variables are presented together. Long term data concerning the fluid level of the patient with respect to dialysis can be used by the health care providers in order to determine whether the patient is approaching the target fluid level after each dialysis session. The rate at which fluid level increases between sessions can be used for determining the optimal schedule for dialysis. For example, if the fluid level of the patient rises quickly between dialysis sessions, the rapid fluid level rise may signal a need to increase dialysis frequency. If the patient is having issues with large fluid gains between dialysis sessions, the large fluid gains may mean that the target fluid levels need to be changed. One skilled in the art will understand that a time period for the chart can be longer or shorter than the 13 days shown in FIG. 22. A long time period shown on the chart can help the health care providers assess whether enough fluid is being removed each dialysis session, if there are any recurring problems with large gains in fluid, or whether the target fluid level of the patient should be altered.

In any embodiment of the first, second, third, fourth, fifth and sixth aspects of the invention, the systems described herein can use the data shown in FIG. 22, or in displays with longer time windows to determine the average fluid level achieved after dialysis over the particular time window. This time window can be any window of interest. In any embodiment of the second, third, and fourth inventions, the time window chosen may be two dialysis sessions. In any embodiment of the second, third, and fourth inventions, the time window can be between any of two dialysis sessions to 1 year or longer, one week to two weeks, one week to one month, two weeks to two months, one month to six months, or six months to a year. After determining the average fluid level achieved over the time period of interest, the user can determine how this particular dialysis session compares with respect to the average dialysis session over the time period. The user can also determine how close to the target weight the patient has gotten over the time period, or warn the user if the patient is starting out in a wet state, or if they did not get to a completely dry state during the last dialysis session. The displays, such as shown in FIG. 22, show a long term dialysis efficiency index.

In any embodiment of the first, second, third, fourth, fifth and sixth aspects of the invention, the frequency of measurements of other medical parameters can be adjusted based on the patient fluid level relative to the patient's estimated dry weight. For example, if the patient fluid level is far above the estimated dry weight, the frequency of monitoring other medical parameters can be increased during this time period.

One skilled in the art will understand that other medical parameters can be included in the output of the first, second, third, fourth, fifth and sixth aspects of the invention. In any embodiment of the first, second, third, fourth, fifth and sixth aspects of the invention, the medical parameters can include arrhythmia information, heart rate, fluid level, blood pressure, or potassium or other blood ion levels. In any embodiment of the first, second, third, fourth, fifth and sixth aspects of the invention, multiple parameters can be included on a single chart. By way of example, a single chart can include both fluid level and the incidence of arrhythmia along with the occurrence of dialysis sessions.

In any embodiment of the first, second, third, fourth, fifth and sixth aspects of the invention, the dialysis parameters shown on the output can include more than the time that dialysis took place. The amount of fluid removed, the ultrafiltration rate, or the concentration of solutes in the dialysate can be included on the same chart.

One skilled in the art will understand that continuous monitoring of every medical parameter is not necessary. Certain medical parameters, such as dialysis symptoms, potassium level, calcium level, or blood pH, can be monitored periodically. Dialysis symptoms can include whether the patient experienced pain, cramping, light headedness, and the severity of the symptoms. The output provided by the system can still show the occurrence of dialysis and the periodically monitored medical parameter. In any embodiment of the first, second, third, fourth, fifth and sixth aspects of the invention, parameters that are measured to be outside of a predetermined range can be highlighted, or shown with a specific symbol.

One skilled in the art will also understand that the particular time period provided in the output of the first, second, third, fourth, fifth and sixth aspects of the invention is flexible. The time period can be selected based on the needs of the researchers or health care providers. For example, at the start of a dialysis session, understanding how the health status of the patient changed from the start to the end of the previous dialysis session, along with how the patient responded physiologically to the dialysis, can be important. Fluid levels and arrhythmia information from the previous week can be valuable to the dialysis clinic for determining the effectiveness of the particular dialysis sessions. A longer period of time, such as week or months, may be valuable in order to determine long term trends. If the user needs to see the effects of dialysis on a particular medical parameter over a long period of time, the output can be shown for weeks, months or years. The output can be shown for lengths of time between 1 hour and 1 year, 1-2 hours, 1 hour-1 day, 4 hours-7 days, 1 day-1 month, 7 days-30 days, 30 days-6 months, 4 months-1 year, or for longer than one year. Trending the information enables physicians to see patterns between dialysis session parameters and patient health episodes. By placing sequential dialysis sequences next to one another, the physician can determine the effectiveness of interventions in preventing futures symptoms. Typically, nephrologists will conduct a comprehensive review of the patient each month. The ability to look at data concerning fluid levels, arrhythmias and blood pressure across 1, 2 or 4 weeks can enable the nephrologists to determine long term trends and if necessary change the dialysis prescription, anti-arrhythmic medications, dialysis frequency or any other corrective action. If a shorter time period is needed, the output can be selected for hours or days. In any embodiment of the first, second, third, fourth, fifth and sixth aspects of the invention, the output can show one dialysis session, or a small portion, such as one hour or less, of a dialysis session. In any embodiment of the first, second, third, fourth, fifth and sixth aspects of the invention, the user can select the time period to be displayed. In any embodiment of the first, second, third, fourth, fifth and sixth aspects of the invention, the display can be generated for months or years, but allow the user to select the particular window of interest. For example, if an output display shows the incidence of arrhythmia corresponding to dialysis sessions for an entire year, the user can select only the previous week. The data for the previous week can then be shown larger, and in greater detail. In any embodiment of the first, second, third, fourth, fifth and sixth aspects of the invention, the user can pre-select the time intervals for data to be shown. The user can enter in the specific hours, days, weeks, months, or years to be displayed. In any embodiment of the first, second, third, fourth, fifth and sixth aspects of the invention, a sliding bar or other interface can be used for the user to be able to set the interval to be displayed.

Other dialysis information in addition to the occurrence of a dialysis session can be included in the output of the second, third, and fourth first, second, third, fourth, fifth and sixth aspects of the invention. Dialysis parameters such as the time a dialysis session takes place, the length of a dialysis session, the amount of fluid removed, symptoms experienced by the patient, and the dialysis session prescription can also be included. These parameters can be included in the outputs described herein. Providing specific parameters from each dialysis session in the output will allow the health care providers to determine the effects of each dialysis parameter, and the effects of changing the dialysis parameters, on the monitored medical parameters.

The exact appearance of the output can be changed without departing from the scope of the first, second, third, fourth, fifth and sixth aspects of the invention. Although many of the charts shown in FIGS. 15-22 include the dialysis sessions as darkened bars, the dialysis sessions can instead be shown as any suitable character or symbol. Further, the occurrence of a dialysis session need not be shown on a single display or chart with the monitored medical parameter. Instead, a second display chart showing the occurrence of dialysis sessions can be included, wherein the two displays or charts are synchronized in time. For instance a chart showing when dialysis occurs along with the fluid removed during dialysis could be shown in one panel, with arrhythmia information, blood pressure, and heart rate each shown in separate panels below the dialysis chart. The chart can be created on a computer monitor, handheld device, programmer, dialysis machine display, or formatted for a paper printout.

The output displays of the first, second, third, fourth, fifth and sixth aspects of the invention can enable physicians or other users to see the temporal link between the dialysis and observed arrhythmias or other medical parameters. This can enables the physician to take actions to reduce the occurrence of negative dialysis effects.

Figure 23:
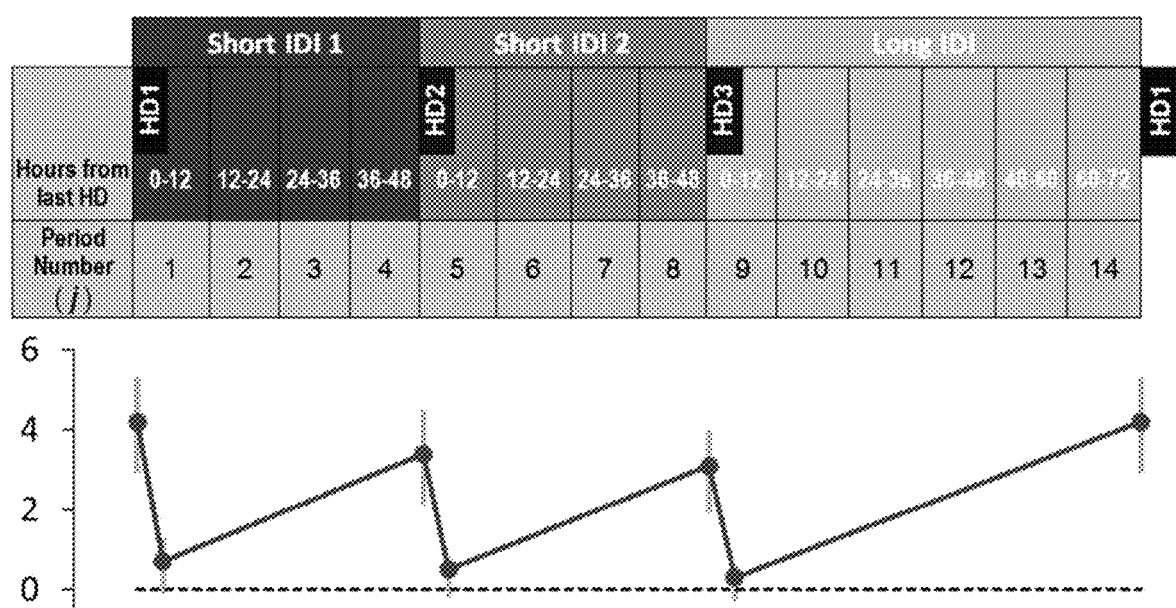
FIG. 23 is a sample display showing the percentage over dry weight of a subject over the course of multiple dialysis sessions.

In any embodiment of the first, second, third, fourth, fifth and sixth aspects of the invention, an output can be generated showing a medical parameter with regards to dialysis treatment over the course of weeks, months, or years. The data can be compiled to show the average effects of dialysis on a medical parameter. An example, showing the percentage over dry weight for a patient with respect to dialysis sessions is shown in FIG. 23. In FIG. 23 the percent over dry weight is shown in 12 hour periods, with dialysis occurring at periods 1, 5, and 9. As is shown in FIG. 23, the % over dry weight for the patient was generally at or near 0% immediately following dialysis, shown in period numbers 1, 5, and 9. After each dialysis session, the percent over dry weight increases, reaching a maximum of between 2 and 4 percent just prior to the next dialysis session during the short interdialytic windows. The percent over dry weight increased to above 4% after the longer dialytic window, as shown in period number 14. The data presented in FIG. 23 shows the health care providers how effectively the dialysis works to keep the patient near the dry weight over the course of a longer period of time. Heart rate variability is significantly linked to the patient's percent over dry weight. Higher excess fluid levels are associated with reductions in heart rate variability.

Figure 24:
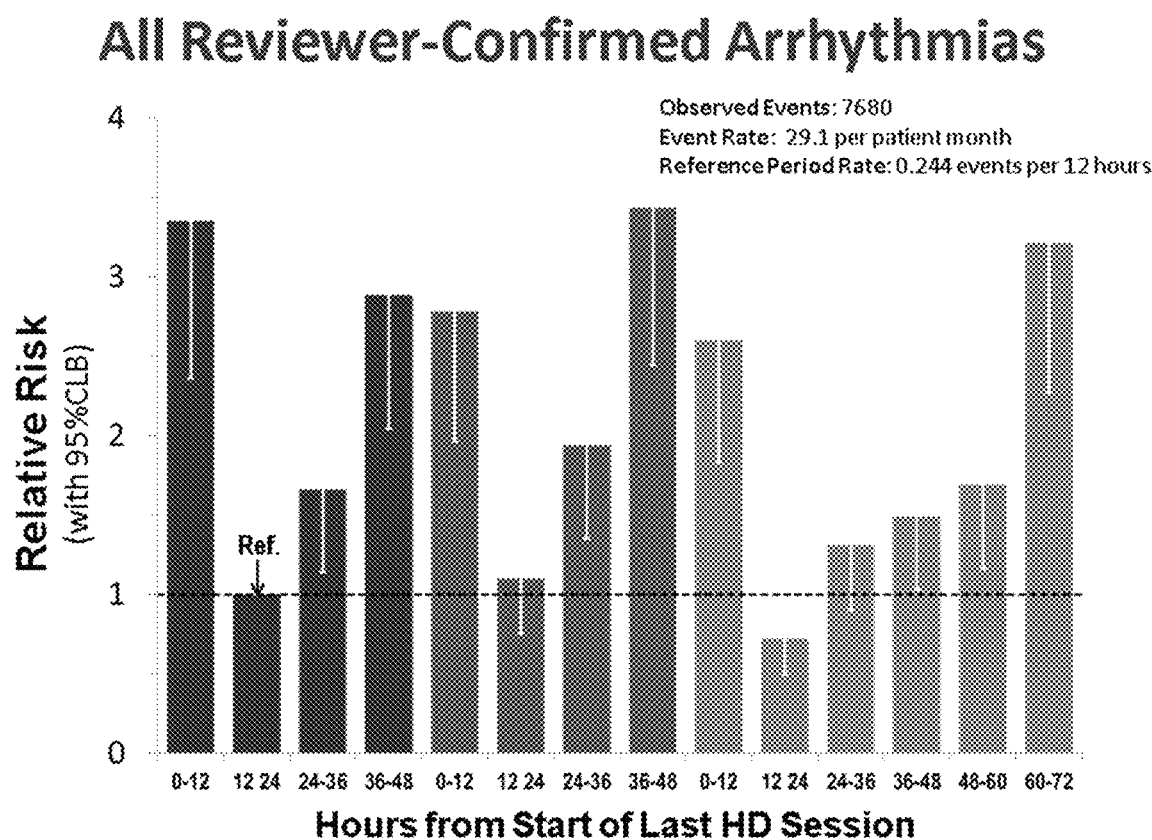
FIG. 24 is a sample display showing the relative risk of arrhythmia with respect to the timing of dialysis sessions.

In any embodiment of the first, second, third, fourth, fifth and sixth aspects of the invention, the data presented can be used to generate risk factors for a patient with respect to the timing of dialysis, as shown in FIG. 24. FIG. 24 shows a negative binomial regression model of the relative risk of any review-confirmed arrhythmic episodes during the dialytic week computed across many patients. A similar display could be computed for a single patient once data has been collected for an extended period of time. Each block refers to a twelve hour period with respect to the previous dialysis session. The dependent variable of the negative binomial regression is the number of arrhythmic events the subject experienced during the each period. Clinically significant arrhythmias were defined as bradycardia of ≤40 bpm for ≥6 seconds, asystole of ≥3 seconds, sustained ventricular tachycardia of ≥130 bpm for ≥30 seconds, and symptomatic arrhythmias. The analysis includes all 12 hour periods, regardless of whether the period contained any arrhythmic events. The estimated model includes a fixed event for each of the 14 time periods shown in FIG. 24. Estimates of these period risks were used to calculate the relative risks shown in the figure. The model also includes a full set of patient-specific fixed effects that (1) improve the estimated time period risk effects by controlling for variation across patients in fixed characteristics (age, sec, comorbidity conditions, etc) and (2) allow for the dependence across repeated observations on the same subject. This is critical in obtaining useful standard error and confidence interval estimates for the estimated relative risks.

The white error bars within each of the bars of FIG. 24 indicate the lower bound of a one-sided 95% confidence interval for each relative risk estimate. The interpretation of these estimates is that there is a 95% confidence that the true relative risk for the time interval lies above the lower edge of the white error bars. For periods where the lower edge of the white bar is above the reference, shown by the dashed line, there is a statistically significant (p<0.05) risk of arrhythmia in that period relative to the reference period, which is set as the period starting 12 hours after the first dialysis session of the dialytic week. As is shown in FIG. 24, for most periods with a statistically significant elevated risk, the lower bound of the error bar is significantly above the reference, and that the p-values in this time period would therefore be significantly smaller than the 0.05 level.

As is noted in FIG. 24, the mean arrhythmic event rate for the reference interval is 0.244 events per 12 hours. Multiplying this factor by the relative risk for a time interval provides an estimate of the arrhythmic event rate in that interval.

As can be seen in FIG. 24, the arrhythmic risk is concentrated in the 24 hours centered on the start of each dialysis session. In particular, arrhythmic risk peaked during the 12 hour intervals beginning with each dialysis session. The risk in these time periods is about three times as great as during the reference period. The arrhythmic risk falls sharply after the first 12 hours of the interdialytic window, before rising again towards the end of the window. These results are consistent with the findings of Foley, et al, N Engl J Med. 2011; 365(12):1099-1107, on variation in the risk of CVD related hospitalization and death over the dialytic week in USRDS hemodialysis patients. The results shown in FIG. 24 are also consistent with the results of Bleyer, et al, Kidney international. June 2006; 69:(12)2268-2273 and Genovesi et al, Nephrology, Dialysis, Transplantation 2009; 24(8):2529-2536, on variation in the risk of sudden cardiac death in ESRD patients with time elapsed since the last hemodialysis session, and show that arrhythmias are frequent during dialysis and strongly associated with the dialysis schedule.

One skilled in the art will understand that the choice of 12-hour periods in the graph shown in FIG. 24 can be longer or shorter in any of the first, second, third, fourth, fifth and sixth aspects of the invention. The risk periods used in the current invention are flexible. Further, the choice of the first 12-24 hour interval as the reference can be changed. This period was chosen because the period is near the nadir of the risk for the entire week, but other periods can be chosen as the reference.

The relative risks shown in FIG. 24 allow the health care providers to see if there is a need to change dialysis parameters, such as if the relative risk is highest immediately after dialysis, or schedule extra dialysis sessions, such as if the relative risk is highest immediately before dialysis sessions.

Figure 25:
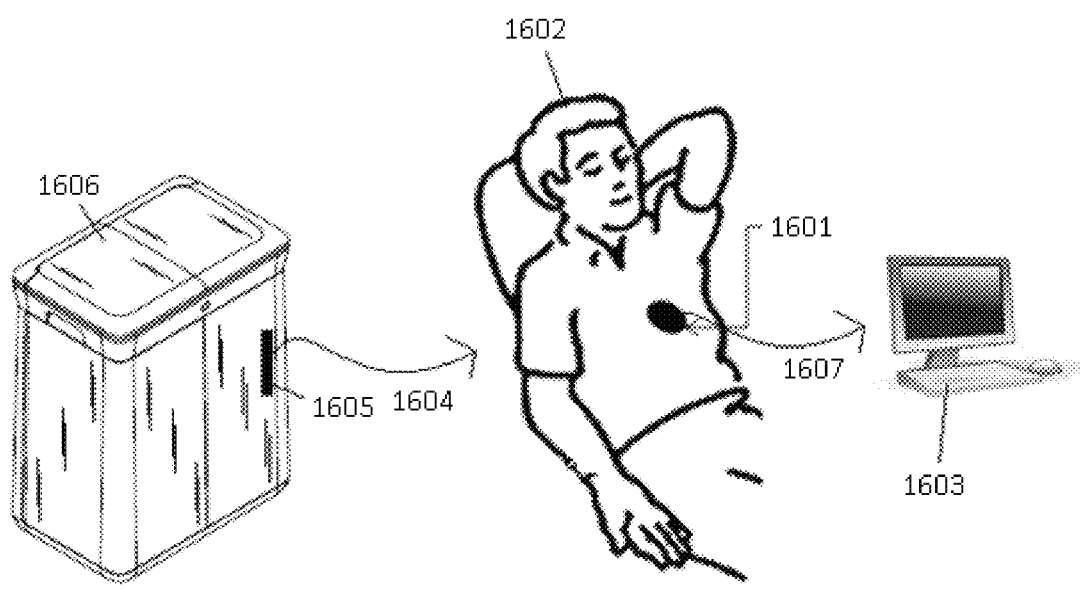
FIG. 25 shows an embodiment of the invention showing the communications between a dialysis machine, a medical device and a processor.

FIG. 25 shows one embodiment of a system that can be used for medical monitoring in accordance with the first, second, third, fourth, fifth and sixth aspects of the invention. In any embodiment of the first, second, third, fourth, fifth and sixth aspects of the invention, an Implantable Medical Device (IMD) 1601 can be implanted in a patient 1602. The IMD can measure impedance and/or ECG measurements. The IMD can be a pacemaker or implantable cardioverter-defibrillator (ICD). In embodiments where sensing is external the patient, a wireless electrode patch and system for measuring the physiological condition of a subject can be used. The electrode patch for ECG monitoring can include related methods for sensing, analyzing and/or transmitting or relaying a physiological signal to a processor or computer configured to receive the data. The wireless electrode patch and system can be lightweight, compact and reusable. The wireless electrode patch can also provide a low, power system for extended battery life and use. The wireless electrode can be applied as a single patch but can be configured as more than one patch.

The IMD 1601 can comprise one or more sensors that can monitor at least one medical parameter as explained herein. The IMD 1601 can be configured to receive a signal alerting the device that a dialysis session has begun, or that a dialysis session is ongoing, such as signal 1604 sent from transmitter 1605 on dialysis machine 1606. A processor, as may be included in computer 1603 in electronic communication with the IMD 1601 through signal 1607 can obtain the medical data from the IMD 1601 and display an output showing both the dialysis sessions for the patient and the monitored medical parameter for the same time period. In any embodiment of the first, second, third, fourth, fifth and sixth aspects of the invention, the IMD 1601 can be configured to transmit the medical information to an electronic health record or other system using signal 1607. The processor can collect the data from the IMD and the dialysis data from a dialysis machine or by manual entry, and synchronize the data while recording the time of the dialysis session. In any embodiment of the first, second, third, fourth, fifth and sixth aspects of the invention, the data collected and synchronized by the processor in computer 1603 can transmit the data to the patient's medical records or any other receiver. In any embodiment of the first, second, third, fourth, fifth and sixth aspects of the invention, the processor can be a part of the dialysis machine 1606, the IMD 1601 or any other component, and need not be inside of an external computer. In any embodiment of the first, second, third, fourth, fifth and sixth aspects of the invention, the IMD 1601 can be configured with a receiver to receive data on the dialysis session or from the patient's electronic medical records. This enables the processor to be configured as part of the IMD 1601. The IMD 1601 can then consolidate the data and send the data to a receiver, programmer, computer, handheld system, or any other system known in the art with the data in consolidated form.

In any embodiment of the first, second, third, fourth, fifth and sixth aspects of the invention, more than one set of data can be provided on a single chart. The processor can synchronize multiple sets of data, such as arrhythmia information, blood solute levels, blood pressure, or others with the dialysis information. This can be sent to the patient's EMD or a handheld device as described herein and provided as one or more charts showing all the information of interest to the user.

In any embodiment of the first, second, third, fourth, fifth and sixth aspects of the invention, the processor can receive the dialysis information directly from a source other than the IMD. For example, a user can manually input the dialysis information into a computer or a patient could enter symptom data into a handheld which synchronizes with the EMR or IMD. In any embodiment of the first, second, third, fourth, fifth and sixth aspects of the invention, the dialysis machine can transmit the dialysis information to the processor through either wired or wireless means.

The IMD 1601 can send and receive data through any standard communication protocol, including Bluetooth Low Energy, radio frequency, cellular or any other type of communication known in the art. In any embodiment of the first, second, third, fourth, fifth and sixth aspects of the invention, the IMD 1601 can be configured so that the IMD 1601 begins to send and receive data as soon as the IMD 1601 is proximity to the dialysis machine 1606 or processor 1603. The IMD 1601 can be configured to detect a magnetic field or triggering radio frequency signal sent by the dialysis machine 1606 or processor 1603. This would enable the IMD to refrain from transmitting information when the IMD 1601 is not within range of a receiver. In any embodiment of the first, second, third, fourth, fifth and sixth aspects of the invention, the IMD 1601 can be configured to automatically record the start of a dialysis session in response to the trigger signal detected from dialysis machine 1606. In any embodiment of the first, second, third, fourth, fifth and sixth aspects of the invention, the communication between the dialysis machine, IMD and processor can be encrypted to protect patient privacy.

Figure 26:
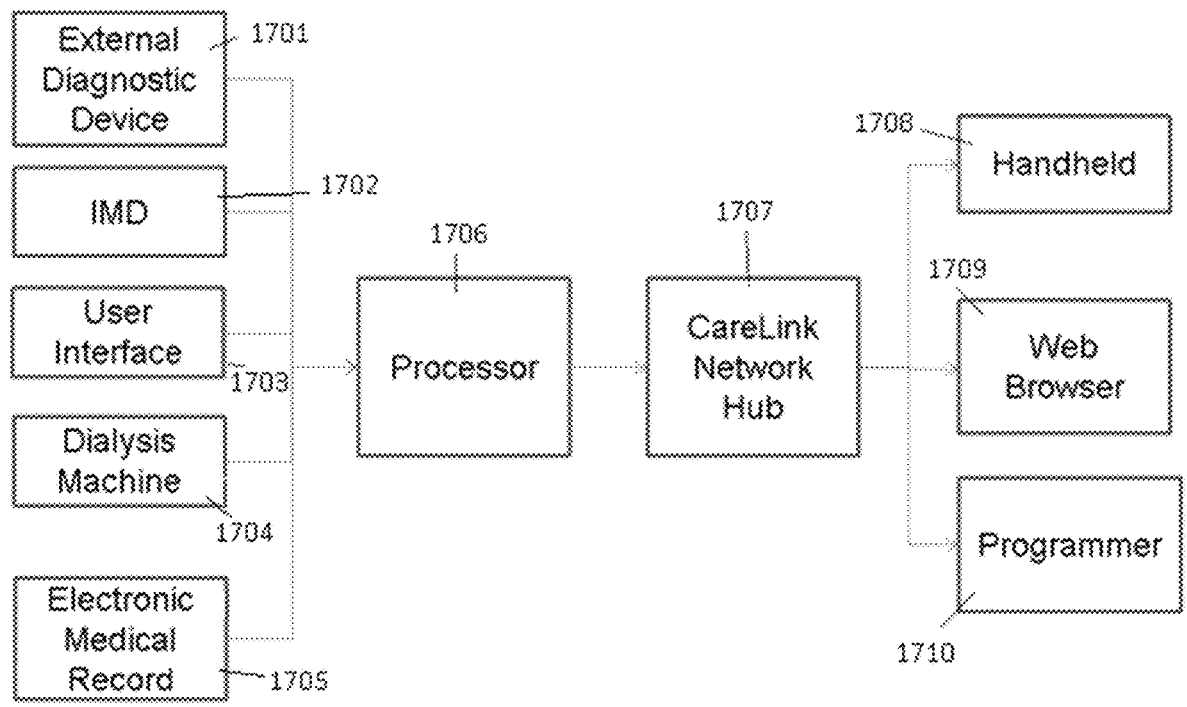
FIG. 26 shows the inputs and outputs according to an embodiment of the invention.

FIG. 26 shows a chart with possible signal transmissions from each of the components of a medical monitoring system. External medical devices 1701, such as EKGs, blood pressure cuffs, hematocrit measurement machines, or other medical devices, can be configured to transmit patient health data to the central processor 1706. An implantable medical device 1702 can transmit data such as impedance, heart rate or arrhythmia information to the processor 1706. Other information, such as how the patient feels can be transmitted by manual entry through user interface 1703. In any embodiment of the first, second, third, fourth, fifth and sixth aspects of the invention, the dialysis information can also be transmitted to the processor by manual entry through user interface 1703. In any embodiment of the first, second, third, fourth, fifth and sixth aspects of the invention, the dialysis information can be directly obtained from a dialysis machine 1704. In any embodiment of the first, second, third, fourth, fifth and sixth aspects of the invention, the timing and prescription of a dialysis session can be obtained from the patient's electronic medical records 1705.

The processor 1706 shown in FIG. 26 can in any embodiment of the first, second, third, fourth, fifth and sixth aspects of the invention can be a part of any of the devices described. The processor 1706 can be integral to the IMD, any external diagnostic device or the dialysis machine. In any embodiment of the first, second, third, fourth, fifth and sixth aspects of the inventions the processor can be in an external computer, such as is shown in FIG. 25.

The processor 1706 of FIG. 26 can be configured to synchronize the inputs received from each of the sources. In this way, the processor 1706 can create an output showing the medical and dialysis parameters of interest simultaneously.

In any embodiment of the first, second, third, fourth, fifth and sixth aspects of the invention, the processor 1706 can be configured to communicate with a network hub 1707, such as the CareLink Network Hub. The network hub 1707 can organize and store the data from the processor 1706 and prepare and transmit the data in the desired output form. In any embodiment, the network hub 1707 can transmit the data to a handheld device 1708, a web browser based application 1709 or to a programmer 1710.

Not all of the sources shown in FIG. 26 are necessary for the first, second, or third inventions. In any embodiment of the first, second, third, fourth, fifth and sixth aspects of the invention, any of the sources can be removed. For example, the dialysis information can be obtained from a dialysis machine 1704, and the system need not be configured to obtain this information from the electronic medical records 1705. Similarly, the user interface 1703 can be eliminated if all parameters of interest can be monitored with sensors.

The network hub 1707 is not necessary for the first, second, or third inventions. In any embodiment of the first, second, third, fourth, fifth and sixth aspects of the invention, the processor 1706 can perform the functions described herein as being performed by the network hub 1707. The output can be transmitted to any device or application capable of receiving the data. Other possible embodiments of the first, second, third, fourth, fifth and sixth aspects of the invention for the output receiver are known in the art and are within the scope of the first, second, third, fourth, fifth and sixth aspects of the invention. In any embodiment of the second, third, and fourth inventions, the output can be sent directly to a receiver on the dialysis machine. The dialysis machine can automatically suggest or implement changes to the dialysis session based on the received data, as explained herein.

One skilled in the art will understand that any IMD capable of sensing and transmitting data concerning patient medical parameters is within the scope of the first, second, third, fourth, fifth and sixth aspects of the invention. In any embodiment of the first, second, third, fourth, fifth and sixth aspects of the invention, medical parameters can be sensed and transmitted by hemodialysis machines, drug delivery devices, ILRs, blood panels, or the system may use a micro-fluidics based ambulatory blood composition monitor, which would allow physicians to see the post-dialysis session physiology (and normalization curves/oscillations) as the body seeks to rebalance post intervention.

In any embodiment of the first, second, third, fourth, fifth and sixth aspects of the invention, the dialysis information can automatically be transmitted to the IMD. A dialysis machine can include a transmitter, and the IMD can include a receiver. The transmitter can transmit a trigger signal, which can automatically be received by the IMD. Upon receipt of the trigger signal, the IMD can automatically record the occurrence and duration of the dialysis session. Non-limiting examples of technology capable of transmitting the trigger signal include radio frequency transmission, Bluetooth, cellular transmission, magnetic fields, and mechanical vibration (e.g. tapping of the device).

In any embodiment of the first, second, third, fourth, fifth and sixth aspects of the invention the trigger signal can be caused by proximity to the dialysis machine. In any embodiment of the first, second, third, fourth, fifth and sixth aspects of the invention, when the patient is within a certain distance of the dialysis machine, the system can assume that the proximity is because the patient is receiving dialysis. In any embodiment of the first, second, third, fourth, fifth and sixth aspects of the invention, the trigger signal can be sent by the dialysis machine when a dialysis session begins and ends. The transmitter need not be on the dialysis machine itself, and can instead be located away from the dialysis machine, but in electronic communication with the dialysis machine. Any system wherein the transmitter can determine if dialysis is occurring is within the scope of the first, second, third, fourth, fifth and sixth aspects of the invention.

In any embodiment of the first, second, third, fourth, fifth and sixth aspects of the invention, the proximity of the patient to the processor can automatically cause the transmission of the medical data to the processor. The transmission of dialysis data to the processor can be caused by the same trigger, or the information can manually be entered by the user.

In any embodiment of the first, second, third, fourth, fifth and sixth aspects of the invention, a user interface can be included in the system to allow the entry of patient reported medical parameters and symptoms. For example, the user can input whether the patient experienced pain or cramping in the period since the last dialysis session. The user can also input the severity of any symptoms experienced by the patient. In any embodiment of the first, second, third, fourth, fifth and sixth aspects of the invention, the approximate timing and severity of the symptoms can be entered, such as shortly after the last dialysis session, or shortly before the current dialysis session. The output shown can include these non-measured symptoms along with the symptoms measured by sensors, which can allow the health care providers to adjust dialysis parameters in order to maximize the patient's quality of life.

Figure 27:
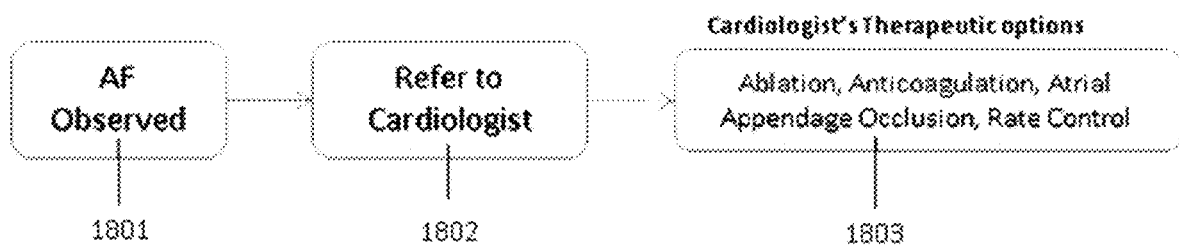
FIG. 27 shows a flow chart depicting the traditional method of dealing with arrhythmia in dialysis patients.

The medical monitoring of the first, second, third, fourth, fifth and sixth aspects of the invention can be adapted to determine the proper course of action in response to medical parameters of the patient. FIG. 27 shows the traditional approach to treating dialysis patients experiencing arrhythmia or atrial fibrillation. If an atrial fibrillation event is observed in a patient at step 1801, the patient or data can be referred to a cardiologist 1802. In response, the cardiologist can recommend ablation, anticoagulation medication, atrial appendage occlusion, or change the rate of ultrafiltration 1803. However, because there is no reliable method to determine if the atrial fibrillation event is due to dialysis factors, the correct course of action is difficult to determine.

Figure 28:
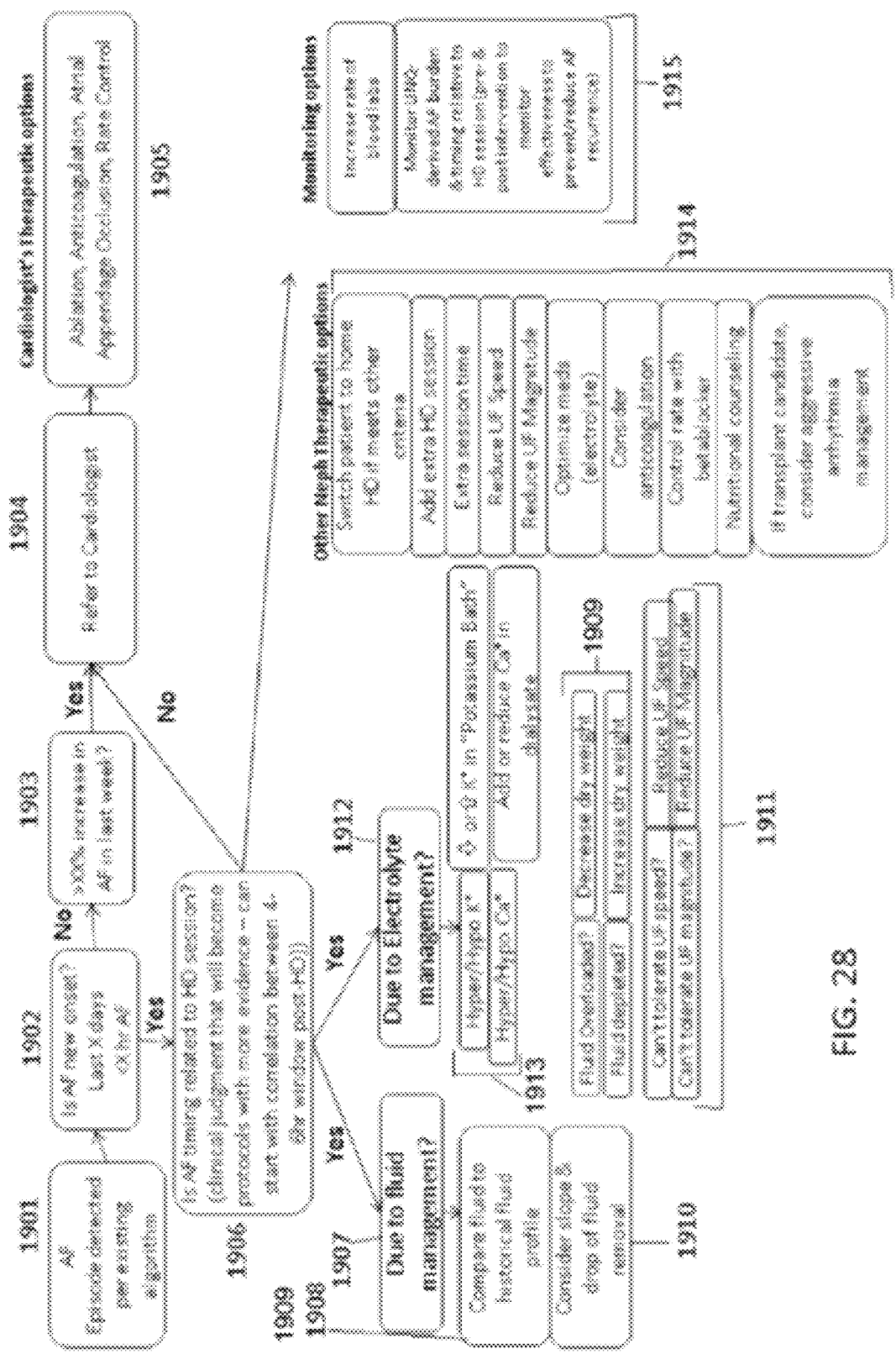
FIG. 28 shows a flow chart depicting a method of dealing with arrhythmias in dialysis patients with the system of the present invention.

FIG. 28 shows how the first, second, third, fourth, fifth and sixth aspects of the invention can result in better accuracy in determining the correct course of action. If the system detects an atrial fibrillation or arrhythmia event in step 1901, the system can determine if the event is a new onset event in step 1902. That is, because the system is monitoring and recording the atrial fibrillation or arrhythmia events, the system can automatically determine if there is an increase in the amount of time spent in atrial fibrillation or arrhythmia events as compared to a previous time window. If the system determines that the detected atrial fibrillation or arrhythmia event is not a new onset event, the system can also determine whether there has been an increase in the amount of atrial fibrillation or arrhythmia during the previous week at step 1903. If there has been an increase, the event can be reported to a cardiologist in step 1904, and the cardiologist can take steps to reduce the occurrence of the events in step 1905. The step of reporting or referring the events to a cardiologist can be accomplished by any means known in the art. In any embodiment of the first, second, third, fourth, fifth and sixth aspects of the invention, the reporting or referring can be accomplished by automatically sending a report to the patient's electronic medical records, to a medical data hub, or to a handheld device.

The system of the first, second, third, fourth, fifth and sixth aspects of the invention can also determine whether the atrial fibrillation or arrhythmia events are related to the occurrence of a dialysis session in step 1906. Whether the atrial fibrillation or arrhythmia event is related to the occurrence of a dialysis session can mean that the arrhythmia or atrial fibrillation is related temporally to the occurrence of the dialysis session or mathematically to any dialysis parameter. The process to determine whether the events are linked to dialysis is described herein. An increase in events before, during, or shortly after dialysis sessions could show that the events are tied to the dialysis. In any embodiment of the first, second, third, fourth, fifth and sixth aspects of the invention, this determination can be made automatically by the medical monitoring system. One skilled in the art will understand that algorithms can be programmed into the medical monitoring system to determine how the timing of the atrial fibrillation or arrhythmia events relate to the timing of dialysis.

If the atrial fibrillation or arrhythmia event is linked to dialysis, the system can also determine whether the event is linked to fluid management in step 1907. Fluid management refers to the fluid levels of the patient, including the pre-dialysis or post-dialysis weight, the change in fluid levels of the patient during a dialysis session or during an interdialytic window, or the rate of fluid level change in the patient. Using the data described above, the system can compare the patient fluid level over a recent time period to the historical fluid level for the patient in step 1908. The system can also determine a correct course of action to take in response to the patient fluid level in step 1909. If the patient fluid level is higher than the historical fluid level for the same patient, the system can lower the patient dry weight. If the patient's fluid level is less than the historical fluid level for the same patient, the system can increase the patient dry weight. The adjustments to patient dry weight can be made automatically by the medical monitoring system, or can be in the form of suggestions to the health care professionals.

The system can also compare the rate and magnitude of the decrease in patient fluid level during dialysis to the historical trend for the patient in step 1910. A rate increase over previous dialysis sessions in fluid level of the patient may indicate that the new onset arrhythmia or atrial fibrillation events are due to the rate of fluid removal. The data from the previous dialysis sessions can be stored in a memory device. In any embodiment of the first, second, third, fourth, fifth and sixth aspects of the invention, the memory device can be a non-transitory memory configured to receive and store the data. An increase in the magnitude of the fluid drop compared to the historical levels for the patient may indicate that the new onset arrhythmia or atrial fibrillation events are due to the magnitude of ultrafiltration. In either case, the system can determine a course of action in step 1911. If the ultrafiltration rate is the cause of the arrhythmia or atrial fibrillation, the system can reduce the ultrafiltration rate. If the ultrafiltration magnitude is the cause of the arrhythmia or atrial fibrillation, the system can reduce the ultrafiltration magnitude. The changes to ultrafiltration described in step 1911 can be made automatically by the medical system, or can be in the form of suggested courses of action to the health care professionals in the form of electronic additions to the patient's electronic medical records, an electronic-mediated communication to a handheld data receiver or hospital data hub, or the suggestions can be transmitted electronically to the health care professionals.

In addition to determining whether the new onset arrhythmia or atrial fibrillation event is due to fluid management in step 1907, the system of the first, second, third, fourth, fifth and sixth aspects of the invention can also determine if the events are due to electrolyte management in step 1912. Electrolyte management refers to the concentration of any electrolyte in the patient's blood or in the fluids used during dialysis. In any embodiment of the first, second, third, fourth, fifth and sixth aspects of the invention, the system can determine whether the events are due to both electrolyte management fluid management. As explained herein, the system can monitor electrolyte or other blood solutes in the patient and determine the effect of dialysis on the concentration of these solutes. If the system determines that there is a significant change in potassium, calcium or other electrolyte levels in the patient due to dialysis, and that these changes correspond to the new onset arrhythmia or atrial fibrillation events in the patient in step 1912, the system can determine possible course of action in step 1913. For example, if the events are linked to increases or decreases in patient potassium level, the system can increase or decrease the concentration of potassium ions in the dialysate as indicated by the term "potassium bath," which describes the dialysate potassium concentration. If the events are linked to increases or decreases in calcium levels, the system can increase or decrease the amount of calcium added to the dialysate. The dialysate concentration of any ion can be adjusted in response to data showing that the new onset arrhythmia or atrial fibrillation events are due to electrolyte management. The changes described in step 1913 can be done automatically by the system, or can take the form of suggestions to the health care professionals in the form of electronic additions to the patient's electronic medical records, an electronic-mediated communication to a handheld data receiver, hospital data hub or medical server, or the suggestions can be transmitted electronically to the health care professionals.

Often, arrhythmia or atrial fibrillation events can be due to both electrolyte and fluid management. As such, the system can determine both of whether there are fluid management factors and whether there are electrolyte management factors. If both electrolyte management and fluid management factors are present, the system can take any of the actions described above, alone or in combination.

In any embodiment of the first, second, third, fourth, fifth and sixth aspects of the invention, the system or user can take other actions in response to dialysis linked arrhythmia or atrial fibrillation events in step 1914. In any embodiment of the first, second, third, fourth, fifth and sixth aspects of the invention, the patient can be switched to home dialysis. If the events are due to a longer interdialytic window, as described herein, the system can add an extra dialysis session. If the patient is not reaching the estimated dry weight, the length of the dialysis session can be increased. This is especially true if the rate of ultrafiltration needs to be decreased. The system can also change the ultrafiltration speed or magnitude. The system can optimize patient medicines or electrolytes. The system can suggest alternative anticoagulation medications. In any embodiment, the system can suggest the use of medications to control heart rate, such as beta blockers. The system can also suggest nutritional counseling or possibly more aggressive arrhythmia management. Examples of drugs that can be delivered or suggested for the patient include Amiodarone (Cordarone, Pacerone), Bepridil Hydrochloride (Vascor), Disopyramide (Norpace), Dofetilide (Tikosyn), Dronedarone (Multaq), Flecainide (Tambocor), Ibutilide (Corvert), Lidocaine (Xylocaine), Procainamide (Procan, Procanbid), Propafenone (Rythmol), Propranolol (Inderal), Quinidine, Sotalol (Betapace), or Tocainide (Tonocarid), or any other drug known in the art. Any of these changes can be made automatically to the dialysis system, be automatically imported electronically into the patient's electronic medical records, an electronic-mediated communication to a handheld data receiver, hospital data hub or medical server, or can be electronically transmitted as suggestions to the health care professionals.

In any embodiment of the first, second, third, fourth, fifth and sixth aspects of the inventions, the system can also adjust monitoring in response to dialysis linked arrhythmias in step 1915. For example, the system can automatically suggest an increase in the rate of blood lab work. In any embodiment of the first, second, third, fourth, fifth and sixth aspects of the invention, the system can continue to monitor the atrial fibrillation or arrhythmia burden and timing with respect to dialysis in order to determine the effectiveness of the interventions described.

One skilled in the art will understand that various combinations and/or modifications and variations can be made in the dialysis system depending upon the specific needs for operation. Moreover, features illustrated or described as being part of an aspect of the invention can be included in the aspect of the invention, either alone or in combination.

We claim:

1. A medical monitoring system, comprising:
    a medical device comprising one or more sensors configured to sense at least one medical parameter;
    an input configured to receive at least one parameter of a dialysis session;
    a processor in electronic communication with the medical device and the input configured to obtain the data from the medical device and the input, and to synchronize the data from the medical device and the input; and
    an output configured to output the at least one medical parameter and the at least one parameter of a dialysis session, wherein the output is configured to display the at least one medical parameter and at least one parameter of a dialysis session simultaneously;
    wherein the system is programmed to determine whether an arrhythmia is due to any one of fluid management, electrolyte management, or both fluid management and electrolyte management.

2. The medical monitoring system of claim 1, wherein the system provides an electronic-mediated communication to a medical server based on whether the arrhythmia is due to fluid management, electrolyte management, or both fluid management and electrolyte management.

3. The medical monitoring system of claim 2, wherein the at least one medical parameter includes arrhythmia information; wherein the arrhythmia information comprises at least one parameter selected from the group consisting of arrhythmia timing, arrhythmia duration, arrhythmia rate, arrhythmia burden, and arrhythmia type.

4. The medical monitoring system of claim 1, wherein the output comprises a chart showing at least one medical parameter and at least one dialysis parameter on the same chart, and wherein the medical device is configured to continuously monitor the at least one medical parameter.

5. The medical monitoring system of claim 1, wherein the medical device is an implantable medical device and wherein the at least one parameter of a dialysis session is selected from the group consisting of an occurrence of dialysis, dialysis initiation time, a dialysis time length, and a dialysis session prescription.

6. The medical monitoring system of claim 1, wherein the output shows the at least one medical parameter for a preset time before a dialysis session, during the dialysis session and for a preset time after the dialysis session.

7. The medical monitoring system of claim 6, wherein a user can select the preset time before the dialysis session and the preset time after the dialysis session.

8. The medical monitoring system of claim 6, wherein the preset period is selected from between: 1 hour-1 year, 1-2 hours, 1 hour — 1 day, 4 hours — 7 days, 1 day — 1 month, 7 days — 30 days, 30 days-6 months, or 4 months — 1 year.

9. The medical monitoring system of claim 1, wherein the output shows the at least one medical parameter for a period of time including multiple dialysis sessions and wherein the input is configured to automatically receive the at least one parameter of a dialysis session.

10. The medical monitoring system of claim 9, wherein the input is configured to receive the at least one parameter of a dialysis session from a dialysis machine or a device in communication with a dialysis machine.

11. The medical monitoring system of claim 1, further comprising an interface, wherein the interface is configured to allow for input of at least one parameter of a dialysis session.

12. The medical monitoring system of claim 1, wherein the processor is further programmed to use an algorithm to determine a total hazard estimate of a ventricular arrhythmia based on the at least one medical parameter, wherein the algorithm, for each of the at least one medical parameters, calculates an individual hazard estimate given by $y_1(t)=h_1(t) \circledR x_1(t)$, wherein $h_1(t)=k_1 e^{k2t}$, t is time, $y_1(t)$ is the individual hazard estimate at time t, $k_1$ and $k_2$ are constants for the given parameter, $x_1(t)$ is the medical parameter at time t, and $\circledR$ is a convolution operator; and wherein the total hazard estimate is either a linear or nonlinear summation of individual hazard estimates.

13. The medical monitoring system of claim 12, wherein the algorithm utilizes an adaptive filter to alter each of the constants periodically.

14. The medical monitoring system of claim 1, wherein the processor is further configured to receive fluid management data and electrolyte management data, and the system comprises a transmitter configured to provide an electronic-mediated communication to a medical server to adjust the frequency of measurements of the at least one or more medical parameters in response to the fluid or electrolyte management data.

15. The medical monitoring system of claim 1, wherein the system is programmed to determine whether the arrhythmia is due to fluid management by one or both of:
    comparing a fluid level of a patient to a fluid level of the patient before, during or after previous dialysis sessions, wherein the previous dialysis sessions did not result in arrhythmia; and
    comparing the rate and magnitude of fluid level drop during a dialysis session within a set time period of the arrhythmia to a rate and magnitude of fluid level drop during a previous dialysis session of the patient, wherein the previous dialysis session did not result in arrhythmia.

16. The medical monitoring system of claim 1, wherein the processor is programmed to adjust a measurement frequency of the at least one medical parameter based on any one or more of: an occurrence of arrhythmia, patient fluid level, post-dialysis weight, pre-dialysis weight, or a time duration of arrhythmia.

17. The medical monitoring system of claim 1, wherein the processor provides an electronic-mediated communication to a medical server to adjust monitoring; and wherein the at least one medical parameter is selected from the group consisting of arrhythmia information, heart rate, fluid level, blood ion levels, and blood pressure, post-dialysis weight, and pre-dialysis weight.

18. The medical monitoring system of claim 17, wherein the at least one medical parameter includes arrhythmia information; wherein the arrhythmia information comprises at least one parameter selected from the group consisting of arrhythmia timing, arrhythmia duration, arrhythmia rate, arrhythmia burden, and arrhythmia type.

19. The medical monitoring system of claim 1, wherein, if the system determines that an arrhythmia is due to fluid management, the system determines a new ultrafiltration rate or ultrafiltration magnitude for a patient.

20. The medical monitoring system of claim 1, wherein, if the system determines that an arrhythmia is due to electrolyte management, the system determines a new concentration of one or more electrolytes in a dialysate for a patient.

* * * * *